(12) United States Patent
Sathyanarayanan et al.

(10) Patent No.: US 10,626,176 B2
(45) Date of Patent: Apr. 21, 2020

(54) METHODS OF TREATING CONDITIONS WITH ANTIBODIES THAT BIND B7-H4

(71) Applicant: JOUNCE THERAPEUTICS, INC., Cambridge, MA (US)

(72) Inventors: Sriram Sathyanarayanan, Lexington, MA (US); Tatiana Novobrantseva, Wellesley, MA (US); Virna Cortez-Retamozo, Cambridge, MA (US)

(73) Assignee: JOUNCE THERAPEUTICS, INC., Cambridge, MA (US)

( * ) Notice: Subject to any disclaimer, the term of this patent is extended or adjusted under 35 U.S.C. 154(b) by 307 days.

(21) Appl. No.: 15/522,061

(22) PCT Filed: Oct. 30, 2015

(86) PCT No.: PCT/US2015/058244
§ 371 (c)(1),
(2) Date: Apr. 26, 2017

(87) PCT Pub. No.: WO2016/070001
PCT Pub. Date: May 6, 2016

(65) Prior Publication Data
US 2017/0334999 A1 Nov. 23, 2017

Related U.S. Application Data

(60) Provisional application No. 62/073,823, filed on Oct. 31, 2014.

(51) Int. Cl.
| | | |
|---|---|---|
| *C07K 16/28* | (2006.01) | |
| *A61K 39/395* | (2006.01) | |
| *C07K 16/30* | (2006.01) | |
| *A61K 47/68* | (2017.01) | |
| *A61K 39/00* | (2006.01) | |

(52) U.S. Cl.
CPC ...... *C07K 16/2827* (2013.01); *A61K 39/3955* (2013.01); *A61K 47/6849* (2017.08); *A61K 47/6851* (2017.08); *C07K 16/3015* (2013.01); *C07K 16/3023* (2013.01); *C07K 16/3046* (2013.01); *C07K 16/3069* (2013.01); *A61K 2039/505* (2013.01); *C07K 2317/21* (2013.01); *C07K 2317/33* (2013.01); *C07K 2317/565* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,500,362 A | 3/1996 | Robinson et al. |
| 5,750,373 A | 5/1998 | Garrard et al. |
| 5,770,429 A | 6/1998 | Lonberg et al. |
| 5,821,337 A | 10/1998 | Carter et al. |
| 6,075,181 A | 6/2000 | Kucherlapati et al. |
| 6,150,584 A | 11/2000 | Kucherlapati et al. |
| 6,194,551 B1 | 2/2001 | Idusogie et al. |
| 6,602,684 B1 | 8/2003 | Umana et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas et al. |
| 7,189,826 B2 | 3/2007 | Rodman |
| 7,527,791 B2 | 5/2009 | Adams et al. |
| 7,923,538 B2 | 4/2011 | Shitara et al. |
| 7,994,290 B2 | 8/2011 | Shitara et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0079574 A1 | 4/2005 | Bond |
| 2005/0119455 A1 | 6/2005 | Fuh et al. |
| 2005/0123546 A1 | 6/2005 | Umana et al. |
| 2005/0266000 A1 | 12/2005 | Bond et al. |
| 2006/0270045 A1 | 11/2006 | Cregg et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2009/0002360 A1 | 1/2009 | Chen et al. |

(Continued)

FOREIGN PATENT DOCUMENTS

| | | |
|---|---|---|
| WO | WO 1987/04462 | 7/1987 |
| WO | WO 1997/30087 | 8/1997 |

(Continued)

OTHER PUBLICATIONS

Merriam-Webster Dictionary, accessed at https://www.merriam-webster.com/dictionary/provide on Jun. 26, 2019; 1 page.*
Baca et el., Antibody humanization using monovalent phage display, *Journal of Biological Chemistry*, vol. 272, pp. 10678-10684, Apr. 18, 1997.
Boerner et al., Production of antigen-specific human monoclonal antibodies from in vitro-primed human splenocytes, *Journal of Immunology*, vol. 147 pp. 86-95, Jul. 1, 1991.
Chen, Y. C. et. al., Expression of the novel co-stimulatory molecule B7-H4 by renal tubular epithelial cells, Kidney International, vol. 70, pp. 2092-2099, Dec. 2006.
Choi, I.H. et. al., Genomic Organization and Expression Analysis of B7-H4, an immune inhibitory molecule of the B7 family, Journal of Immunology, vol. 171, pp. 4650-4654, Nov. 2003.
Chothia et al., Canonical structures for the hypervariable regions of immunoglobulins, *Journal of Molecular Biology*, vol. 196, pp. 901-917, Aug. 1987.

(Continued)

*Primary Examiner* — Ilia I Ouspenski
(74) *Attorney, Agent, or Firm* — Knobbe, Martens, Olson & Bear, LLP

(57) ABSTRACT

Provided herein are embodiments relating to therapeutic applications of B7-H4 antibodies.

2 Claims, 27 Drawing Sheets

Specification includes a Sequence Listing.

(56) References Cited

U.S. PATENT DOCUMENTS

| | | | | |
|---|---|---|---|---|
| 2009/0074660 | A1* | 3/2009 | Korman | C07K 16/30 |
| | | | | 424/1.49 |
| 2010/0203056 | A1* | 8/2010 | Irving | A61K 31/7068 |
| | | | | 424/139.1 |
| 2011/0085970 | A1 | 4/2011 | Terrett et al. | |
| 2012/0282637 | A1 | 11/2012 | Huber et al. | |
| 2013/0251736 | A1* | 9/2013 | Kwon | C07K 16/2827 |
| | | | | 424/172.1 |
| 2014/0037551 | A1* | 2/2014 | Zang | C07K 16/2827 |
| | | | | 424/9.2 |
| 2015/0315275 | A1* | 11/2015 | Langermann | C07K 16/2827 |
| | | | | 424/133.1 |

FOREIGN PATENT DOCUMENTS

| | | |
|---|---|---|
| WO | WO 1998/58964 | 12/1998 |
| WO | WO 1999/10494 | 5/1999 |
| WO | WO 1999/22764 | 5/1999 |
| WO | WO 1999/51642 | 10/1999 |
| WO | WO 20000/61739 | 10/1999 |
| WO | WO 2001/29246 | 4/2001 |
| WO | WO 2002/031140 | 4/2002 |
| WO | WO 2003/084570 | 10/2003 |
| WO | WO 2003/085107 | 10/2003 |
| WO | WO 2003/085119 | 10/2003 |
| WO | WO 2003/011878 | 11/2003 |
| WO | WO 2004/092219 | 2/2005 |
| WO | WO 2005/035586 | 4/2005 |
| WO | WO 2005/035778 | 4/2005 |
| WO | WO 2004/056312 | 5/2005 |
| WO | WO 2005/053742 | 6/2005 |
| WO | WO 2006/006693 | 1/2006 |
| WO | WO 2006/003179 | 5/2006 |
| WO | WO 2006/104677 A2 | 10/2006 |
| WO | WO 2006/104677 A3 | 10/2006 |
| WO | WO 2008/077546 | 7/2008 |
| WO | WO 2009/073553 A1 | 6/2009 |
| WO | WO 2011/055968 | 9/2011 |
| WO | WO 2014/159835 | 10/2014 |
| WO | WO 2014/165422 | 10/2014 |

OTHER PUBLICATIONS

Clynes et al., Fc receptors are required in passive and active immunity to melanoma, *Proceedings of the National Academy of Sciences*, vol. 95, pp. 652-656 Oct. 1998.

Collins, M. et al., The B7 family of immune-regulatory ligands, Genome Biology, vol. 6, pp. 223.1-223.7, May 31, 2005.

Crispen, P.L. et. al., Predicting disease progression after nephrectomy for localized renal cell carcinoma: The utility of prognostic models and molecular biomarkers, Cancer, vol. 113, pp. 450-460, Aug. 2008.

Dangaj, D, et al. Novel Recombinant Human B7-H4 Antibodies Overcome Tumoral Immune Escape to Potentiate T-Cell Anti-Tumor Responses, American Associate for Cancer Research, vol. 73, No. 15, pp. 4820-4829, (2013).

Fellouse et al., Synthetic antibodies from a four-amino-acid code: A dominant role for tyrosine in antigen recognition, *Proceedings of the National Academy of Sciences*, vol. 101, No. 34, pp. 12467-12472, Aug. 2004.

Galon, et al., Cancer classification using the Immunoscore: a worldwide task force, Journal of Translational Medicine, Oct. 2012.

Garon et al,, Pembrolizumab for the treatment of non-small-cell lung cancer, New England Journal of Medicine, vol. 372, pp. 2018-2028, May 2015.

Greene et al., Covalent dimerization of CD28/CTLA-4 and oligomerization of CD80/CD86 regulate T cell costimulatory interactions, Journal of Biological Chemistry, vol. 271, pp. 26762-26771, Oct. 1996.

Griffiths et al., Human anti-self antibodies with specificity from phase display libraries, The *EMBO Journal*, vol. 12, pp. 725-734, Feb. 1993.

Han Q et al., Multidimensional analysis of the frequencies and rates of cytokine secretion from single cells by quantitative microengraving, Lab Chip, vol. 10, Iss. 11, pp. 1391-1400, Jun. 2010.

He, C. et al., Clin. and Develop. Immunol. (2011) 1-8 (Article ID 695834).

Hofmeyer, K.A. et al., The Contrasting role of B7-H3, Proceedings of the National Academy of Sciences, vol. 105(30), pp. 10277-10278, Jul. 29, 2008.

Idusogie et al., Mapping of the C1q binding site on rituxan, a chimeric antibody with a human IgG1 Fc, *Journal of Immunology*, vol. 164, pp. 4178-4184, 2000.

Ikemizu, S. et al., Structure and dimerization of a soluble form if B7-1, Immunity vol. 12, pp. 51-60, Jan. 2000.

International Search Report and Written Opinion dated Mar. 4, 2016 in International Patent Application No. PCT/US2015/058244.

International Preliminary Report on Patentability dated May 2, 2017 in International Patent Application No. PCT/US2015/058244.

Jeon, H, et al. Structure and Cancer Immunotherapy of the B7 family Member B7X, Cell Reports, vol. 9, pp. 1-10, (2014).

Korman, A.J. et al. Adv. Immunol. (2007) 90:297-339.

Krambeck et al., B7-H4 expression in renal cell carcinoma and tumor vasculature: Associations with cancer progression and survival. Jun. 23, 2006. Proc Natl Acad Sci U.S.A vol. 103 Issue 27, pp. 10392-10396.

Kryczek, I. et al., Cancer Research. (2007) 67(18): 8900-8905.

Kryczek, I. et al., J. Exp. Med. (2006) 203(4): 871-881.

Leong, S., et al. An Anti-B7-H4 Antibody-Drug Conjugate for the Treatment of Breast Cancer, Research & Early Development, pp. 1717-1729, (2014).

Loke, P. et al. Emerging Mechanisms of Immune Regulation: The Extended B7 Family and Regulatory T-cells. Arthritis Res. Ther. (2004) 6:208-214).

Messina, et al, Scientific Reports, 2012.

Padlan, (1991) *Mol. Immunol*. 28:489-498.

Partial European Search Report dated May 4, 2018 in European Patent Application No. 15854010.4.

Petkova et al. *International Immunology* 18(12):1759-1769 (2006).

Queen et al., (1989) *Proc. Natl Acad. Sci. USA* 86: 10029-10033.

Rosok et al., (1996) *J. Biol. Chem*. 271 :22611-22618).

Shaffer, D., et al., Dissecting the Tumor Micro-Enviornment in Triple Negative Breast Cancer Identifies a Mutually Exclusive Expression Patter n of the Immune Co-Inhibitory Molecules B7-H4 nad PD-L1.

Sheets, M. et al., Efficent Construction of a Large Nonimmune Phage Antibody Library: The Production of High-Affinity Human single-Chain Antibodies to Protein Antigens, Proc. Natl. Acad. Sci. (USA) 95:6157-6162, (1998).

Taube, J. et al., Association of of PD-1, PD-1 Ligands, and other Features of the Tumor Immune Microenvironment with Response to Anti-PD1 Therapy, Clinical Cancer Res, (2014).

Thompson, R.H., et. al. Serum-Soluble B7x Is Elevated in Renal Cell Carcinoma Patentis and is Associated with Advanced Stage, Cancer Res 68:6054-6058, (2008).

Wang, L. et al., VISTA, a novel mouse Ig superfamily ligand that negatively regulates T cell responses, Journal of Experimental Medicine, vol. 208(3), pp. 577-592, Mar. 7, 2011.

Wang, H et al. Chronic Medical Conditions and Risk of Sepsis. Plos One. 7(1):1-10, (2012).

Zang, X. et al., The B7 Family and Cancer Therapy: Costimulation and Coinhabitation, Clinical Cancer Research, vol. 13(18), pp. 5271-5279, Sep. 15, 2007.

Zang, X. et. al. B7-H3 and B7X Are Highly Expressed in Human Prostate Cancer and Associated with Disease Spread and Poor Outcome PNAS (2007) 104:19458-19463.

Zang,X. B7x: A widely expressed B7 family member that inhibits T-cell activation. PNAS (2003)100(18):10388-10392.

Zhang, L., et al. The Costimulatory Molecule B7-H4 Promote Tumor Progression and Cell Proliferation Through Translocationing into Nucleus., Oncogne, vol. 32, pp. 5347-5358, (2013.

Zhang, N., et al. Preparation and Characterization of Monoclonal Antibody Against Human B7-H4 Molecule, Monoclonal Antibodies, vol. 33, No. 4, pp. 270-274 (2004).

(56) References Cited

OTHER PUBLICATIONS

Zhao, R. et al., HHLA2 is a member of the B7 family and inhibits human CD4 and CD8 T-cell function, Proceedings of the National Academy of Sciences, vol. 220(24), pp. 9879-9884, May 28, 2013.
Communication pursuant to Article 94(3) EPS, dated Sep. 3, 2019, for European Patent Application No. 15 854 010.4.

* cited by examiner

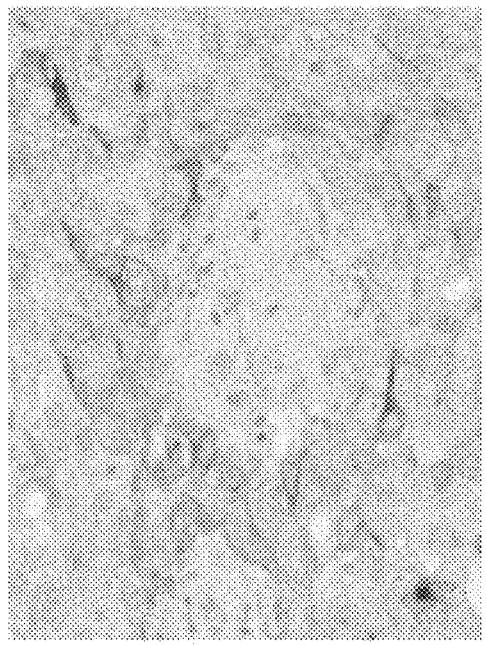
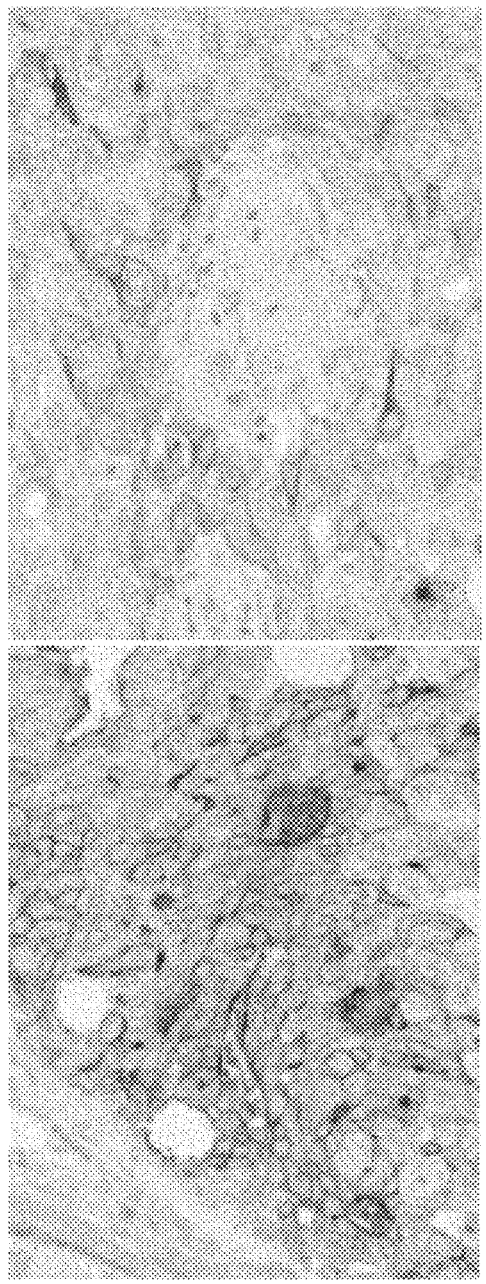
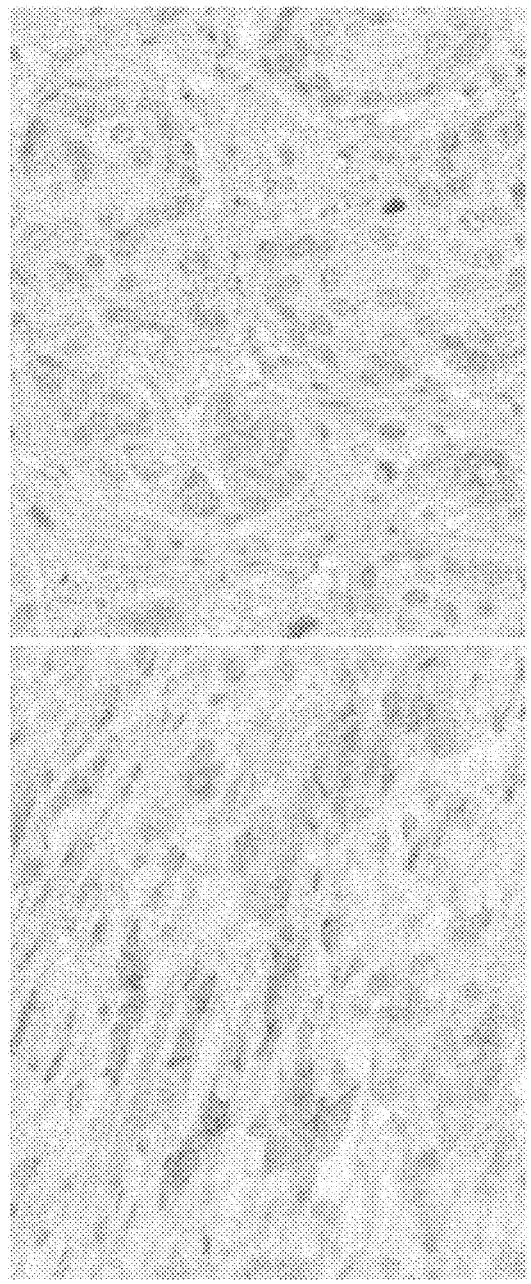
FIG. 3

FIG. 4
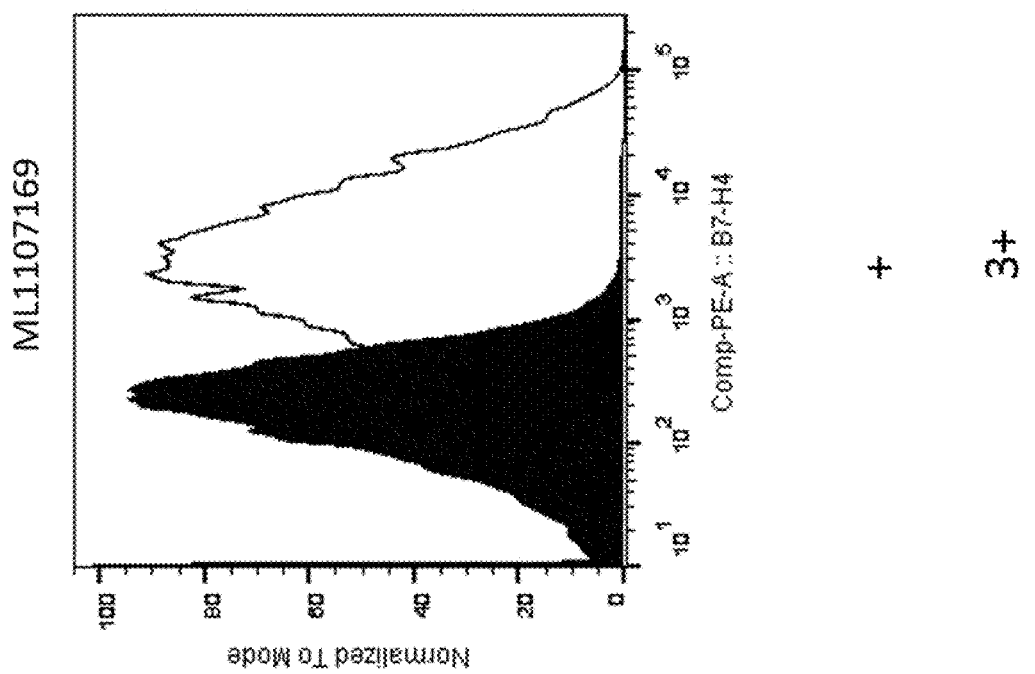
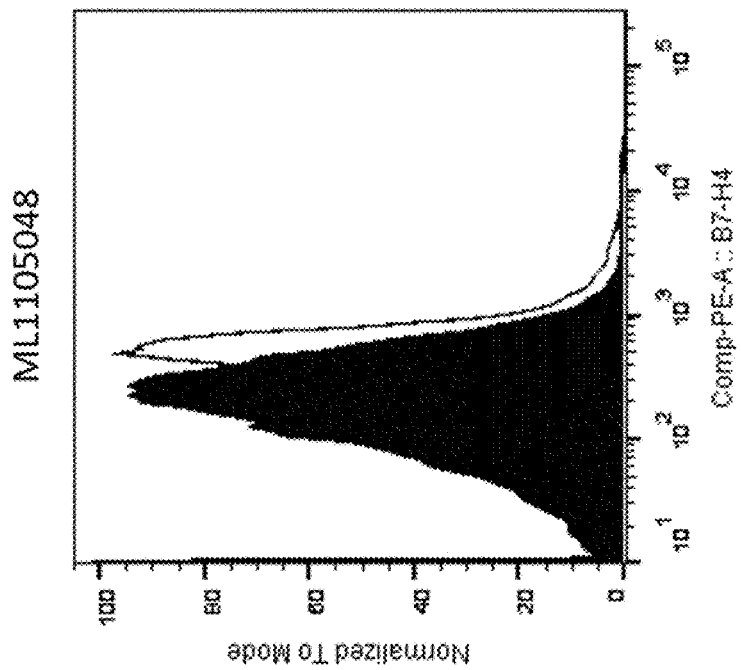

FIG. 6
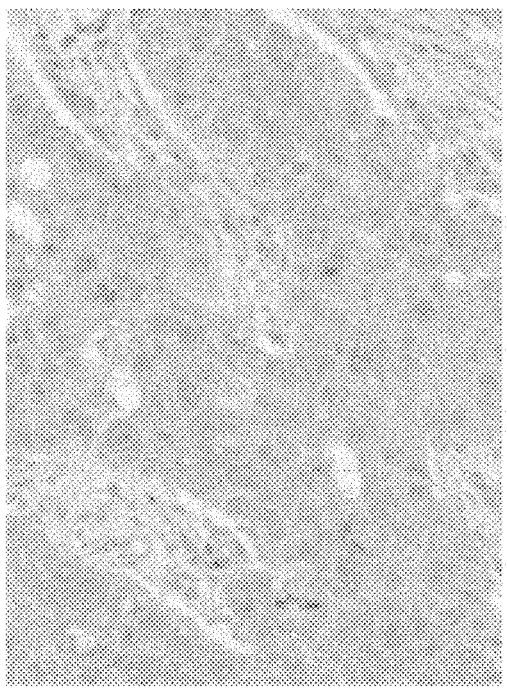
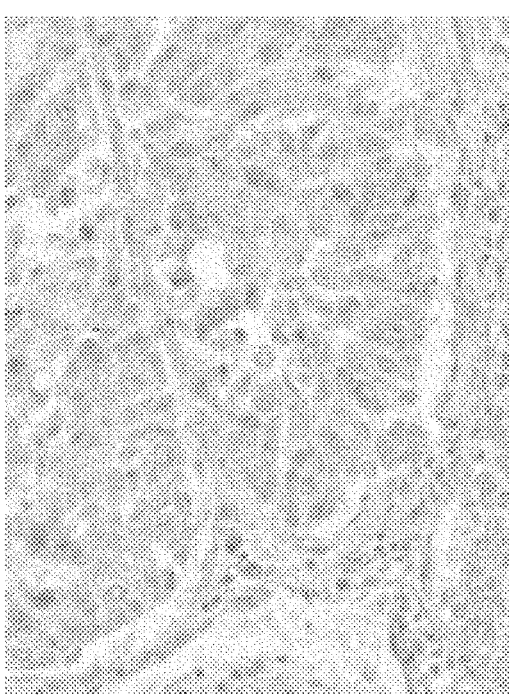
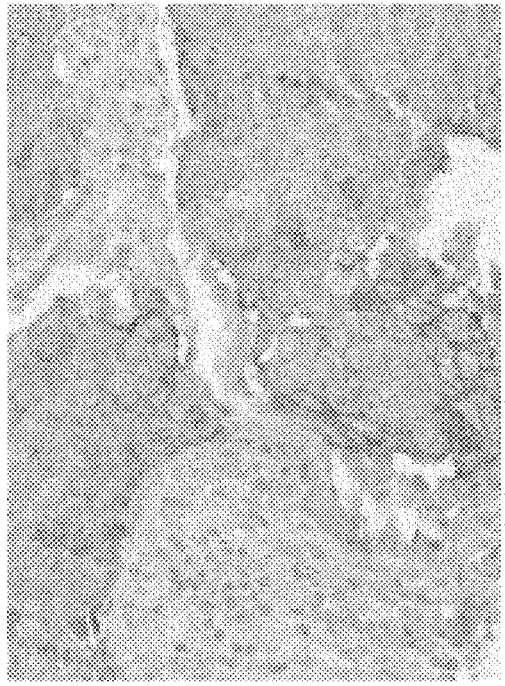
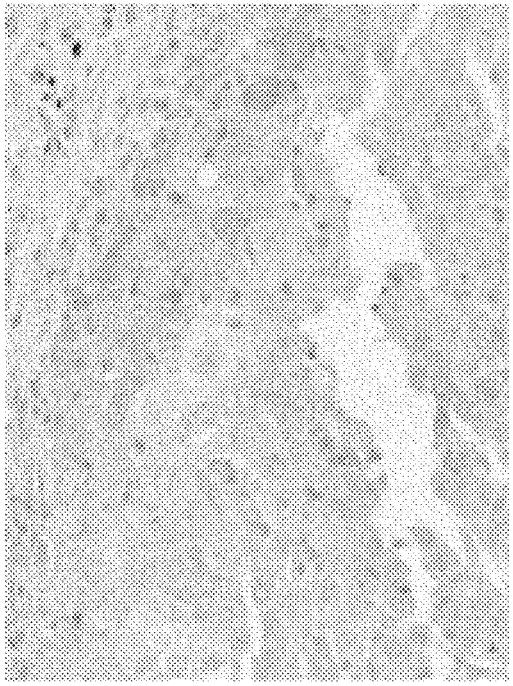

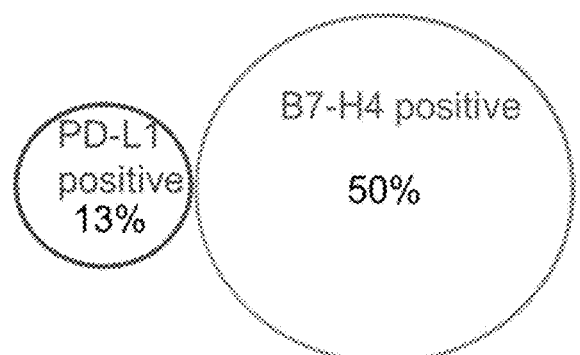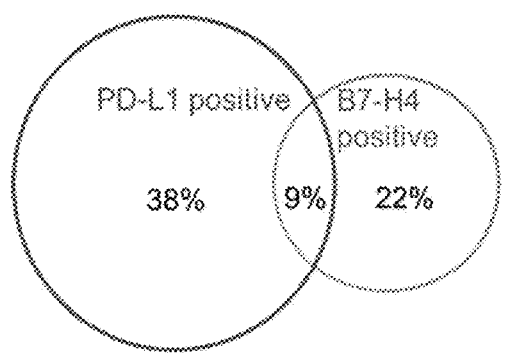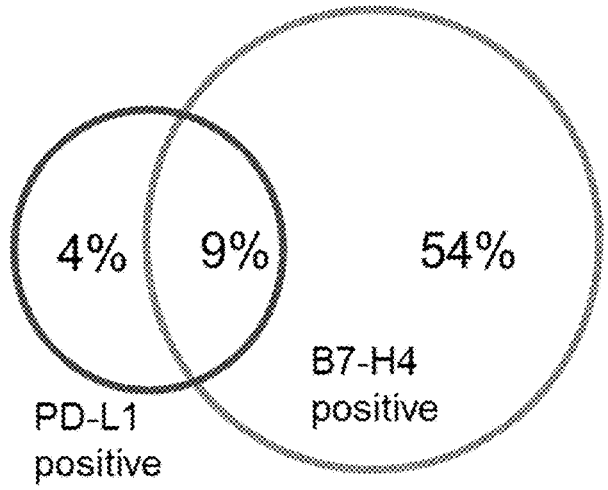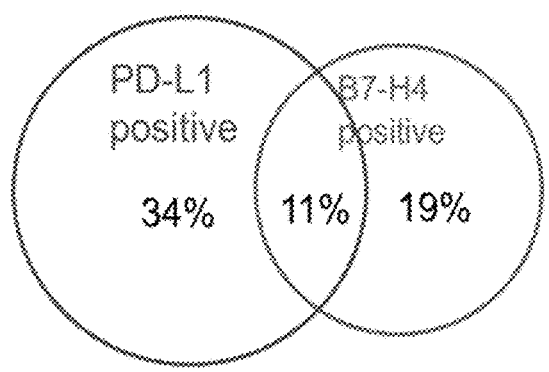
FIG. 7

FIGURE 10A

Human B7-H4 Isoform 1 (UniProt: Q7Z7D3-1):

SEQ ID NO: 1

```
         10         20         30         40         50         60
MASLGQILFW SIISIIIILA GAIALIIGFG ISGRHSITVT TVASAGNIGE DGILSCTFEP 70         80         90        100        110        120
DIKLSDIVIQ WLKEGVLGLV HEFKEGKDEL SEQDEMFRGR TAVFADQVIV GNASLRLKNV 130        140        150        160        170        180
QLTDAGTYKC YIITSKGKGN ANLEYKTGAF SMPEVNVDYN ASSETLRCEA PRWFPQPTVV 190        200        210        220        230        240
WASQVDQGAN FSEVSNTSFE LNSENVTMKV VSVLYNVTIN NTYSCMIEND IAKATGDIKV 250        260        270        280
TESEIKRRSH LQLLNSKASL CVSSFFAISW ALLPLSPYLM LK
```

Human B7-H4 isoform 1 polynucleotide sequence (GenBank: NM 024626.3)

```
acactatttta aggccaatac acgggagctg ttgtgagtc accaaggaag gcagcggcag
ctccactcag ccagtaccca gatacgctgg gaaccttccc cagccatggc ttccctgggg
cagatcctct tctggagcat aattagcatc atcattattc tggctggagc aattgcactc
atcattggct ttggtatttc agggagacac tccatcacag tcactactgt cgcctcagct
gggaacattg gggaggatgg aatcctgagc tgcactttg aacctgacat caaactttct
gatatcgtga tacaatggct gaaggaaggt gttttaggct tggtccatga gttcaaagaa
ggcaaagatg agctgtcgga gcaggatgaa atgttcagag ccggacagc agtgtttgct
gatcaagtga tagttggcaa tgcctctttg cggctgaaaa acgtgcaact cacagatgct
ggcacctaca atgttatat catcacttct aaaggcaagg ggaatgctaa ccttgagtat
aaaactggag ccttcagcat gccggaagtg aatgtggact ataatgccag ctcagagacc
ttgcggtgtg aggctcccg atggttcccc cagcccacag tggtctgggc atcccaagtt
gaccagggag ccaacttctc ggaagtctcc aataccagct ttgagctgaa ctctgagaat
gtgaccatga aggttgtgtc tgtgctctac aatgttacga tcaacaacac atactcctgt
atgattgaaa atgacattgc caaagcaaca gggatatca aagtgacaga atcggagatc
aaaaggcgga gtcacctaca gctgctaaac tcaaaggctt ctctgtgtgt ctcttctttc
tttgccatca gctgggcact tctgcctctc agcccttacc tgatgctaaa ataatgtgcc
tcggccacaa aaaagcatgc aaagtcattg ttacaacagg gatctacaga actatttcac
caccagatat gacctagttt tatatttctg ggaggaaatg aattcatatc tagaagtctg
gagtgagcaa acaagagcaa gaaacaaaaa gaagccaaaa gcagaaggct ccaatatgaa
caagataaat ctatcttcaa agacatatta gaagttggga aaataattca tgtgaactag
acaagtgtgt taagagtgat aagtaaaatg cacgtggaga caagtgcatc cccagatctc
agggacctcc cctgcctgt cacctgggga gtgagaggac aggatagtgc atgttctttg
```

```
tctctgaatt tttagttata tgtgctgtaa tgttgctctg aggaagcccc tggaaagtct
atcccaacat atccacatct tatattccac aaattaagct gtagtatgta ccctaagacg
ctgctaattg actgccactt cgcaactcag gggcggctgc attttagtaa tgggtcaaat
gattcacttt ttatgatgct tccaaaggtg ccttggcttc tcttcccaac tgacaaatgc
caaagttgag aaaaatgatc ataattttag cataaacaga gcagtcggcg acaccgattt
tataaataaa ctgagcacct tcttttaaa caaacaaatg cgggtttatt tctcagatga
tgttcatccg tgaatggtcc agggaaggac ctttcacctt gtctatatgg cattatgtca
tcacaagctc tgaggcttct cctttccatc ctgcgtggac agctaagacc tcagttttca
gagcagtggg actcagctgg ggtgatttcg cccccatct ccggggaat gtctgaagac
aattttggtt acctcaatga gggagtggag gaggatacag tgctactacc aactagtgga
tagaggccag ggatgctgct caacctccta ccatgtacag gacgtctccc cattacaact
acccaatccg aagtgtcaac tgtgtcaggg ctaagaaacc ctggttttga gtagaaaagg
gcctggaaag aggggagcca acaaatctgt ctgcttcctc acattagtca ttggcaaata
agcattctgt ctctttggct gctgcctcag cacagagagc cagaactcta ggataacatc
tctcagtgaa cagagttgac aaggcctatg ggaaatgcct gatgggatta tcttcagctt
gttgagcttc taagtttctt tcccttcatt ctaccctgca agccaagttc tgtaagagaa
atgcctgagt tctagctcag gttttcttac tctgaattta gatctccaga ccctgcctgg
ccacaattca aattaaggca acaaacatat accttccatg aagcacacac agactttga
aagcaaggac aatgactgct tgaattgagg ccttgaggaa tgaagctttg aaggaaaaga
atactttgtt tccagccccc ttcccacact cttcatgtgt cttcctggac cttggagcca cggtgactgt attacatgtt gttatagaaa actgatttta gagttctgat cgttcaagag aatgattaaa tatacatttc ctacaccaaa aaaaaaaaaa aa    SEQ ID NO: 7
```

Human B7-H4 Isoform 2 (UniProt: Q7Z7D3-2):

SEQ ID NO: 2

```
         10         20         30         40         50         60
MASLGQILFW SIISIIIILA GAIALIIGFG ISAFSMPEVN VDYNASSETL RCEAPRWFPQ 70         80         90        100        110        120
PTVVWASQVD QGANFSEVSN TSFELNSENV TMKVVSVLYN VTINNTYSCM IENDIAKATG 130        140        150        160
DIKVTESEIK RRSHLQLLNS KASLCVSSFF AISWALLPLS PYLMLK
```

Human B7-H4 isoform 2 polynucleotide sequence encoding SEQ ID NO:4
(EMBL: AAZ17406.1)

```
atggcttccc tggggcagat cctcttctgg agcataatta gcatcatcat tattctggct
ggagcaattg cactcatcat tggctttggt atttcagcct tcagcatgcc ggaagtgaat
gtggactata atgccagctc agagaccttg cggtgtgagg ctccccgatg gttccccag
cccacagtgg tctgggcatc ccaagttgac cagggagcca acttctcgga agtctccaat
accagctttg agctgaactc tgagaatgtg accatgaagg ttgtgtctgt gctctacaat
gttacgatca acaacacata ctcctgtatg attgaaaatg acattgccaa agcaacaggg
gatatcaaag tgacagaatc ggagatcaaa aggcggagtc acctacagct gctaaactca
aaggcttctc tgtgtgtctc ttctttcttt gccatcagct gggcacttct gcctctcagc
ccttacctga tgctaaaata a
```

SEQ ID NO: 8

FIGURE 10C

Human B7-H4 Isoform 3 (UniProt: Q7Z7D3-3):

SEQ ID NO: 3

```
          10         20         30         40         50         60
MASLGQILFW SIISIIIILA GAIALIIGFG ISEVSVWLSA MKGWCRSSKA SLSIDLCFLN 70         80
FRETLHHSHY CRLSWEHWGG WNPELHF
```

Human B7-H4 isoform 3 polynucleotide sequence encoding SEQ ID NO:6
(EMBL: AAS13400.1)

```
ggtgagtcac caaggaaggc agcggcagct ccactcagcc agtacccaga tacgctggga
accttcccca gccatggctt ccctggggca gatcctcttc tggagcataa ttagcatcat
cattattctg gctggagcaa ttgcactcat cattggcttt ggtatttcag aagtctctgt
ctggctttca gcaatgaagg gttggtgtag aagttccaag gcttccctta gcattgatct
ttgcttcctg aacttcaggg agacactcca tcacagtcac tactgtcgcc tcagctggga
acattgggga ggatggaatc cagagctgca ctttgaacc tgacatcaaa ctttctgata
tcgtgataca atggctgaag gaaggtgttt taggcttggt ccatgagttc aaagaaggca
aagatgagct gtcggagcag gatgaaatgt tcagaggccg gacagcagtg tttgctgatc
aagtgatagt tggcaatgcc tctttgcggc tgaaaaacgt gcaactcaca gatgctggca
cctacaaatg ttatatcatc acttctaaag
```

SEQ ID NO: 9

FIGURE 10D

Human B7-H4 Isoform 4 (UniProt: Q7Z7D3-4):

SEQ ID NO: 4

```
          10         20         30         40         50
 60
MFRGRTAVFA DQVIVGNASL RLKNVQLTDA GTYKCYIITS KGKGNANLEY
KTGAFSMPEV 70         80         90        100        110
120
NVDYNASSET LRCEAPRWFP QPTVVWASQV DQGANFSEVS NTSFELNSEN
VTMKVVSVLY 130        140        150        160        170
180
NVTINNTYSC MIENDIAKAT GDIKVTESEI KRRSHLQLLN SKASLCVSSF
FAISWALLPL

SPYLMLK
```

Human B7-H4 isoform 4 polynucleotide sequence encoding (EMBL: BAH13967.1)

```
ctggtaatct gtggcgtaac aagacctcca ggtgattctc tgtattagca gccgctctgt
gctccctgat tcctccagaa aagcacaagg atttaatcca gatagatata aatttcacct
gggatcattt atcattccac attcttcttt aagaaatgtg ctaaagagcc acagatgggt
cttgatgaaa acaaggaaa agccatgaag ttctacagc ataattagca tcatcattat
tctggctgga gcaattgcac tcatcattgg ctttggtatt tcagggagac actccatcac
agtcactact gtcgcctcag ctggaacat tggggaggat ggaatcctga gctgcacttt
tgaacctgac atcaaacttt ctgatatcgt gatacaatgg ctgaaggaag gtgttttagg
cttggtccat gagttcaaag aaggcaaaga tgagctgtcg gagcaggatg aaatgttcag
aggccggaca gcagtgtttg ctgatcaagt gatagttggc aatgcctctt gcggctgaa
aaacgtgcaa ctcacagatg ctggcaccta caaatgttat atcatcactt ctaaaggcaa
ggggaatgct aaccttgagt ataaactgg agccttcagc atgccggaag tgaatgtgga
ctataatgcc agctcagaga ccttgcggtg tgaggctccc cgatggttcc cccagcccac
agtggtctgg gcatcccaag ttgaccaggg agccaacttc tcggaagtct ccaataccag
ctttgagctg aactctgaga atgtgaccat gaaggttgtg tctgtgctct acaatgttac
gatcaacaac acatactcct gtatgattga aatgacatt gccaaagcaa cagggatat
caaagtgaca gaatcggaga tcaaaggcg gagtcaccta cagctgctaa actcaaaggc
ttctctgtgt gtctcttctt tctttgccat cagctgggca cttctgcctc tcagcccttg
cctgatgcta aaataatgtg ccttggccac aaaaaagcat gcaaagtcat tgttacaaca
```

```
gggatctaca gaactatttc accaccagat atgacctagt tttatatttc tgggaggaaa
tgaattcata tctagaagtc tggagtgagc aaacaagagc aagaaacaaa aagaagccaa
aagcagaagg ctccaatatg aacaagataa atctatcttc aaagacatat tagaagttgg
gaaaataatt catgtgaact agacaagtgt gttaagagtg ataagtaaaa tgcacgtgga
gacaagtgca tccccagatc tcagggacct cccctgcct gtcacctggg gagtgagagg
acaggatagt gcatgttctt tgtctctgaa tttttagtt atatgtgctg taatgttgct         ct
```

SEQ ID NO: 10

Murine B7-H4 (UniProt: Q7TSP5)

SEQ ID NO: 5

```
         10         20         30         40         50
 60
MASLGQIIFW SIINIIIILA GAIALIIGFG ISGKHFITVT TFTSAGNIGE
DGTLSCTFEP 70         80         90        100        110
120
DIKLNGIVIQ WLKEGIKGLV HEFKEGKDDL SQQHEMFRGR TAVFADQVVV
GNASLRLKNV 130        140        150        160        170
180
QLTDAGTYTC YIRTSKGKGN ANLEYKTGAF SMPEINVDYN ASSESLRCEA
PRWFPQPTVA 190        200        210        220        230
240
WASQVDQGAN FSEVSNTSFE LNSENVTMKV VSVLYNVTIN NTYSCMIEND
IAKATGDIKV 250        260        270        280
TDSEVKRRSQ LQLLNSGPSP CVFSSAFVAG WALLSLSCCL MLR
```

Murine B7-H4 polynucleotide sequence (GenBank: BC032925)

```
caaaatctgg ccccacacac agcaggactg tgggaaggaa ctccctctcc atggcttcct
tggggcagat catcttttgg agtattatta acatcatcat catcctggct ggggccatcg
tggctttggc atttcaggca agcacttcat cacggtcacg accttcacct cagctggaaa
cattggagag gacgggaccc tgagctgcac ttttgaacct gacatcaaac tcaacggcat
cgtcatccag tggctgaaag aaggcatcaa aggtttggtc cacgagttca agaaggcaa
agacgacctc tcacagcagc atgagatgtt cagaggccgc acagcagtgt ttgctgatca
ggtggtagtt ggcaatgctt ccctgagact gaaaaacgtg cagctcacgg atgctggcac
ctacacatgt tacatccgct cctcaaaagg caaggggaat gcaaaccttg agtataagac
cggagcctc agtatgccag ataaatgt ggactataat gccagttcag agagtttacg
ctgcgaggct cctcgtggt tccccagcc cacagtggcc tgggcatctc aagttgacca
aggagccaac ttctcagaag tctccaacac cagctttgag ttgaactctg agaatgtgac
catgaaggtc gtatctgtgc tctacaatgt cacaatcaac aacacatact cctgtatgat
```

```
tgaaaacgac attgccaaag ccaccgggga catcaaagtg acagattcag aggtcaaaag
gcggagtcag ctgcagttgc tgaactctgg gccttccccg tgtgtttctt cttctgcctt
tgtggctggc tgggcactcc tatctctctc ctgttgcctg atgctaagat gagggccct
ggctacacaa aagcatgcaa cgttgctggt ccaacagaat cccggagaac tacagaaata
ttttcctcaa gacatgacct agttttatat ttctagaaga agatgaaatc atgtctagaa
gtctggagag agcagacagg aacaagatgt ggaaggaaaa caaaagtaac ccacagacac
ccccgatcgg aacaagatgg acctagaaaa taattcaacc aaactagagt atactaagtg
tgctgttaca atgtgtgtag ggtaggtgtc ctcccacatc tcagggcct ccctggtcc
accagctcct gagttaggat gggctgttat gatgtcactc tgaaggttcc tggatggttc
ctactgccat atactcattt tatattcagc acattaaacc atagtgaatg ctaaaaaaaa
aaaaaaaaaa aaa
```

SEQ ID NO: 11

FIGURE 10E Cont.

mAb 11

| | CDR1 (H31-H35) | CDR2 (H50-H65) | CDR3 (H95-H102) |
|---|---|---|---|
| VH | GYWMH (SEQ ID NO: 12) | TIFPGNSDTNYNQKFKG (SEQ ID NO: 13) | GLRTWLDY (SEQ ID NO: 14) |
| | CDR1 (L24-L34) | CDR2 (L50-L56) | CDR3 (L89-L97) |
| VL | LASQTIGTWLA (SEQ ID NO: 15) | AATSLAD (SEQ ID NO: 16) | QQFYTTPWT (SEQ ID NO: 17) |

VH (SEQ ID NO: 18)

EVQLQQSGTVLARPGASVEMSCKTSGYTFTGYWMHWVKQRPGQGLEWIGTIFPGNSDTNYNQKFKGKAKLTAVTSANTAYMD
LSSLSNDDSAVYYCTMGLRTWLDYWGQGTLVTVSA

VL (SEQ ID NO: 19)

DIQMTQSPASQSASLGESVTITCLASQTIGTWLAWYQQKPGKSPQLLIYAATSLADGVPSRFSGSASGTKFSFKISSLQAEDFVSYYC
QQFYTTPWTFGGGTNLEIK

FIG. 11C mAb 18

VH

| CDR1 (H31-H35) | CDR2 (H50-H65) | CDR3 (H95-H102) |
|---|---|---|
| TYNMH | AIYPANGDTSYNQKFKG | CGFYDDYDWYFDV |
| (SEQ ID NO: 20) | (SEQ ID NO: 21) | (SEQ ID NO: 22) |

VL

| CDR1 (L24-L34) | CDR2 (L50-L56) | CDR3 (L89-L97) |
|---|---|---|
| RSSQSLVYSNGNTHLH | KVSNRFS | CQSTHVPYT |
| (SEQ ID NO: 23) | (SEQ ID NO: 24) | (SEQ ID NO: 25) |

VH (SEQ ID NO: 26)

QAYLQQSGAELVRPGASVKMSCKASGHTFTTYNMHWVKQTPRQGLEWIGAIYPANGDTSYNQKFKGKATLTVDESSSTAYMQL
SSLTSEDSAVYLCARCGFYDDYDWYFDVWGTGTTVTVSS

VL (SEQ ID NO: 27)

DVVMTQTPLSLPVSLGDQASISCRSSQSLVYSNGNTHLHWYLQKPGQSPKLLIYKVSNRFSGVPDRFSGSGSGTDFTLKISRVEAED
LGVYFCCQSTHVPYTFGGGTKLEIK

FIG. 11D mAb 37

VH

| CDR1 (H31-H35) | CDR2 (H50-H65) | CDR3 (H95-H102) |
|---|---|---|
| NFGVH | VIWSGGSTDYNALFIS | NRVGRLLDS |
| (SEQ ID NO: 28) | (SEQ ID NO: 29) | (SEQ ID NO: 30) |

VL

| CDR1 (L24-L34) | CDR2 (L50-L56) | CDR3 (L89-L97) |
|---|---|---|
| KASQNVDTVVA | SASRRYI | QQYSTNPT |
| (SEQ ID NO: 31) | (SEQ ID NO: 32) | (SEQ ID NO: 33) |

VH (SEQ ID NO: 34)

QVQLKQSGPGLVQPSQSLSITCTVSGFSLANFGVHWVRQSPGKGLEWLGVIWSGGSTDYNALFISRLSISKDISKSQVFFKMNSLQ
ADDTAIYYCVRNRVGRLLDSWGQGTTLTVSS

VL (SEQ ID NO: 35)

DIVMTQSQKVMSTTVGDRVTITCKASQNVDTVVAWYQQKPGQSPKLLIHSASRRYIGVPDRFTGSGSGTDFTLTINNVQSEDLAD
YFCQQYSTNPTFGAGTMLELK

FIG. 11E mAb 43

| VH | CDR1 (H31-H35)<br>DFTIH<br>(SEQ ID NO: 36) | CDR2 (H50-H65)<br>YIYPGNDNTKYNEKFKG<br>(SEQ ID NO: 37) | CDR3 (H95-H102)<br>NGNYDY<br>(SEQ ID NO: 38) |
|---|---|---|---|
| VL | CDR1 (L24-L34)<br>RSSQSLVHSDGNTYLH<br>(SEQ ID NO: 39) | CDR2 (L50-L56)<br>KVSNRFS<br>(SEQ ID NO: 40) | CDR3 (L89-L97)<br>SQSTHVPLT<br>(SEQ ID NO: 41) |

VH (SEQ ID NO: 42)

QVQLQQSDAELVTPGASVKISCKVSGYIFTDFTIHWMKQRPEQGLEWIGYIYPGNDNTKYNEKFKGKATLTADKSSSTANMQLNS
LTSEDSAVYFCARNGNYDYWGQGTTLTVSS

VL (SEQ ID NO: 43)

DVVMTQTPLSLPVSLGDQASISCRSSQSLVHSDGNTYLHWNLQRPGQSPKLLIYKVSNRFSGVPDRFSGSGSGTDFTLKINRVEAE
DLGVYFCSQSTHVPLTFGAGTKLELK

FIG. 11F

SEQUENCE LISTING

<160> NUMBER OF SEQ ID NOS: 43

<210> SEQ ID NO 1
<211> LENGTH: 282
<212> TYPE: PRT
<213> ORGANISM: Homo sapiens

<400> SEQUENCE: 1

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280
```

<210> SEQ ID NO 2
<211> LENGTH: 166
<212> TYPE: PRT
<213> ORGANISM: Homo sapiens

<400> SEQUENCE: 2

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Ala Phe Ser Met Pro Glu Val Asn Val Asp Tyr Asn Ala Ser Ser Glu
```

```
                    35                  40                  45
Thr Leu Arg Cys Glu Ala Pro Arg Trp Phe Pro Gln Pro Thr Val Val
 50                  55                  60
Trp Ala Ser Gln Val Asp Gln Gly Ala Asn Phe Ser Glu Val Ser Asn
 65                  70                  75                  80
Thr Ser Phe Glu Leu Asn Ser Glu Asn Val Thr Met Lys Val Val Ser
                     85                  90                  95
Val Leu Tyr Asn Val Thr Ile Asn Asn Thr Tyr Ser Cys Met Ile Glu
                    100                 105                 110
Asn Asp Ile Ala Lys Ala Thr Gly Asp Ile Lys Val Thr Glu Ser Glu
                    115                 120                 125
Ile Lys Arg Arg Ser His Leu Gln Leu Leu Asn Ser Lys Ala Ser Leu
130                 135                 140
Cys Val Ser Ser Phe Phe Ala Ile Ser Trp Ala Leu Leu Pro Leu Ser
145                 150                 155                 160
Pro Tyr Leu Met Leu Lys
                165

<210> SEQ ID NO 3
<211> LENGTH: 87
<212> TYPE: PRT
<213> ORGANISM: Homo sapiens

<400> SEQUENCE: 3

Met Ala Ser Leu Gly Gln Ile Leu Phe Trp Ser Ile Ser Ile Ile
  1               5                  10                  15
Ile Ile Leu Ala Gly Ala Ile Ala Leu Ile Ile Gly Phe Gly Ile Ser
                 20                  25                  30
Glu Val Ser Val Trp Leu Ser Ala Met Lys Gly Trp Cys Arg Ser Ser
                 35                  40                  45
Lys Ala Ser Leu Ser Ile Asp Leu Cys Phe Leu Asn Phe Arg Glu Thr
 50                  55                  60
Leu His His Ser His Tyr Cys Arg Leu Ser Trp Glu His Trp Gly Gly
 65                  70                  75                  80
Trp Asn Pro Glu Leu His Phe
                 85

<210> SEQ ID NO 4
<211> LENGTH: 187
<212> TYPE: PRT
<213> ORGANISM: Homo sapiens

<400> SEQUENCE: 4

Met Phe Arg Gly Arg Thr Ala Val Phe Ala Asp Gln Val Ile Val Gly
  1               5                  10                  15
Asn Ala Ser Leu Arg Leu Lys Asn Val Gln Leu Thr Asp Ala Gly Thr
                 20                  25                  30
Tyr Lys Cys Tyr Ile Ile Thr Ser Lys Gly Lys Gly Asn Ala Asn Leu
                 35                  40                  45
Glu Tyr Lys Thr Gly Ala Phe Ser Met Pro Glu Val Asn Val Asp Tyr
 50                  55                  60
Asn Ala Ser Ser Glu Thr Leu Arg Cys Glu Ala Pro Arg Trp Phe Pro
 65                  70                  75                  80
Gln Pro Thr Val Val Trp Ala Ser Gln Val Asp Gln Gly Ala Asn Phe
                 85                  90                  95
Ser Glu Val Ser Asn Thr Ser Phe Glu Leu Asn Ser Glu Asn Val Thr
```

```
                100             105             110
Met Lys Val Val Ser Val Leu Tyr Asn Val Thr Ile Asn Asn Thr Tyr
            115                 120                 125

Ser Cys Met Ile Glu Asn Asp Ile Ala Lys Ala Thr Gly Asp Ile Lys
    130                 135                 140

Val Thr Glu Ser Glu Ile Lys Arg Arg Ser His Leu Gln Leu Leu Asn
145                 150                 155                 160

Ser Lys Ala Ser Leu Cys Val Ser Ser Phe Ala Ile Ser Trp Ala
                165                 170                 175

Leu Leu Pro Leu Ser Pro Tyr Leu Met Leu Lys
                180                 185

<210> SEQ ID NO 5
<211> LENGTH: 283
<212> TYPE: PRT
<213> ORGANISM: Homo sapiens

<400> SEQUENCE: 5

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
                20                  25                  30

Gly Lys His Phe Ile Thr Val Thr Thr Phe Thr Ser Ala Gly Asn Ile
            35                  40                  45

Gly Glu Asp Gly Thr Leu Ser Cys Thr Phe Glu Pro Asp Ile Lys Leu
        50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Val Ala Gly Trp Ala
            260                 265                 270

Leu Leu Ser Leu Ser Cys Cys Leu Met Leu Arg
        275                 280
```

<210> SEQ ID NO 6
<211> LENGTH: 8
<212> TYPE: PRT
<213> ORGANISM: Artificial Sequence
<220> FEATURE:
<223> OTHER INFORMATION: OVA-peptide

<400> SEQUENCE: 6

Ser Ile Ile Asn Phe Glu Lys Leu
1               5

<210> SEQ ID NO 7
<211> LENGTH: 2622
<212> TYPE: DNA
<213> ORGANISM: Homo sapiens

<400> SEQUENCE: 7

```
acactattta aggccaatac acgggagctg gttgtgagtc accaaggaag gcagcggcag      60
ctccactcag ccagtaccca gatacgctgg gaaccttccc cagccatggc ttccctgggg     120
cagatcctct tctggagcat aattagcatc atcattattc tggctggagc aattgcactc     180
atcattggct ttggtatttc agggagacac tccatcacag tcactactgt cgcctcagct     240
gggaacattg gggaggatgg aatcctgagc tgcactttg aacctgacat caaactttct     300
gatatcgtga taatggct gaaggaaggt gttttaggct tggtccatga gttcaaagaa      360
ggcaaagatg agctgtcgga gcaggatgaa atgttcagag gccggacagc agtgtttgct     420
gatcaagtga tagttggcaa tgcctctttg cggctgaaaa acgtgcaact cacagatgct     480
ggcacctaca atgttatat catcacttct aaaggcaagg ggaatgctaa ccttgagtat     540
aaaactggag ccttcagcat gccggaagtg aatgtggact ataatgccag ctcagagacc     600
ttgcggtgtg aggctccccg atggttcccc cagcccacag tggtctgggc atcccaagtt     660
gaccagggag ccaacttctc ggaagtctcc aataccagc ttgagctgaa ctctgagaat     720
gtgaccatga aggttgtgtc tgtgctctac aatgttacga tcaacaacac atactcctgt     780
atgattgaaa atgacattgc caaagcaaca ggggatatca agtgacaga tcggagatc      840 aaaaggcgga gtcacctaca gctgctaaac tcaaaggctt ctctgtgtgt ctcttctttc     900
tttgccatca gctgggcact ctgcctctc agcccttacc tgatgctaaa ataatgtgcc     960
tcggccacaa aaaagcatgc aaagtcattg ttacaacagg gatctacaga actatttcac    1020
caccagatat gacctagttt tatatttctg ggaggaaatg aattcatatc tagaagtctg    1080
gagtgagcaa acaagagcaa gaaacaaaaa gaagccaaaa gcagaaggct ccaatatgaa    1140
caagataaat ctatcttcaa agacatatta gaagttggga aaataattca tgtgaactag    1200
acaagtgtgt taagagtgat aagtaaaatg cacgtggaga caagtgcatc cccagatctc    1260
agggacctcc ccctgcctgt cacctgggga gtgagaggac aggatagtgc atgttctttg    1320
tctctgaatt tttagttata tgtgctgtaa tgttgctctg aggaagcccc tggaaagtct    1380
atcccaacat atccacatct tatattccac aaattaagct gtagtatgta ccctaagacg    1440
ctgctaattg actgccactt cgcaactcag gggcggctgc attttagtaa tgggtcaaat    1500
gattcacttt ttatgatgct tccaaaggtg ccttggcttc cttcccaac tgacaaatgc     1560 caaagttgag aaaaatgatc ataatttag cataaacaga gcagtcggcg acaccgattt     1620
tataaataaa ctgagcacct tcttttaaa caaacaaatg cgggtttatt tctcagatga    1680
tgttcatccg tgaatggtcc agggaaggac ctttcacctt gtctatatgg cattatgtca    1740
```

| | |
|---|---:|
| tcacaagctc tgaggcttct cctttccatc ctgcgtggac agctaagacc tcagttttca | 1800 |
| gagcagtggg actcagctgg ggtgatttcg cccccccatct ccgggggaat gtctgaagac | 1860 |
| aattttggtt acctcaatga gggagtggag gaggatacag tgctactacc aactagtgga | 1920 |
| tagaggccag ggatgctgct caacctccta ccatgtacag gacgtctccc cattacaact | 1980 |
| acccaatccg aagtgtcaac tgtgtcaggg ctaagaaacc ctggttttga gtagaaaagg | 2040 |
| gcctggaaag aggggagcca acaaatctgt ctgcttcctc acattagtca ttggcaaata | 2100 |
| agcattctgt ctcttggct gctgcctcag cacagagagc cagaactcta ggataacatc | 2160 |
| tctcagtgaa cagagttgac aaggcctatg ggaaatgcct gatgggatta tcttcagctt | 2220 |
| gttgagcttc taagtttctt tcccttcatt ctaccctgca agccaagttc tgtaagagaa | 2280 |
| atgcctgagt tctagctcag gttttcttac tctgaattta gatctccaga ccctgcctgg | 2340 |
| ccacaattca aattaaggca acaaacatat accttccatg aagcacacac agacttttga | 2400 |
| aagcaaggac aatgactgct tgaattgagg ccttgaggaa tgaagctttg aaggaaaaga | 2460 |
| atactttgtt tccagccccc ttcccacact cttcatgtgt cttcctggac cttggagcca | 2520 |
| cggtgactgt attacatgtt gttatagaaa actgatttta gagttctgat cgttcaagag | 2580 |
| aatgattaaa tatacatttc ctacaccaaa aaaaaaaaaa aa | 2622 |

<210> SEQ ID NO 8
<211> LENGTH: 501
<212> TYPE: DNA
<213> ORGANISM: Homo sapiens

<400> SEQUENCE: 8

| | |
|---|---:|
| atggcttccc tggggcagat cctcttctgg agcataatta gcatcatcat tattctggct | 60 |
| ggagcaattg cactcatcat tggctttggt atttcagcct tcagcatgcc ggaagtgaat | 120 |
| gtggactata atgccagctc agagaccttg cggtgtgagg ctccccgatg gttcccccag | 180 |
| cccacagtgg tctgggcatc ccaagttgac caggagccaa acttctcgga agtctccaat | 240 |
| accagctttg agctgaactc tgagaatgtg accatgaagg ttgtgtctgt gctctacaat | 300 |
| gttacgatca caacacata ctcctgtatg attgaaaatg acattgccaa agcaacaggg | 360 |
| gatatcaaag tgacagaatc ggagatcaaa aggcggagtc acctacagct gctaaactca | 420 |
| aaggcttctc tgtgtgtctc ttcttcttt gccatcagct gggcacttct gcctctcagc | 480 |
| ccttacctga tgctaaaata a | 501 |

<210> SEQ ID NO 9
<211> LENGTH: 570
<212> TYPE: DNA
<213> ORGANISM: Homo sapiens

<400> SEQUENCE: 9

| | |
|---|---:|
| ggtgagtcac caaggaaggc agcggcagct ccactcagcc agtacccaga tacgctggga | 60 |
| accttcccca gccatggctt ccctggggca gatcctcttc tggagcataa ttagcatcat | 120 |
| cattattctg gctggagcaa ttgcactcat cattggcttt ggtatttcag aagtctctgt | 180 |
| ctggctttca gcaatgaagg gttggtgtag aagttccaag gcttccctta gcattgatct | 240 |
| tgcttcctg aacttcaggg agacactcca tcacagtcac tactgtcgcc tcagctggga | 300 |
| acattgggga ggatggaatc cagagctgca cttttgaacc tgacatcaaa ctttctgata | 360 |
| tcgtgataca atggctgaag gaaggtgttt taggcttggt ccatgagttc aaagaaggca | 420 |
| aagatgagct gtcggagcag gatgaaatgt tcagaggccg gacagcagtg tttgctgatc | 480 | aagtgatagt tggcaatgcc tctttgcggc tgaaaaacgt gcaactcaca gatgctggca    540 cctacaaatg ttatatcatc acttctaaag                                     570

<210> SEQ ID NO 10
<211> LENGTH: 1442
<212> TYPE: DNA
<213> ORGANISM: Homo sapiens

<400> SEQUENCE: 10
ctggtaatct gtggcgtaac aagacctcca ggtgattctc tgtattagca gccgctctgt     60
gctccctgat tcctccagaa aagcacaagg atttaatcca gatagatata aatttcacct    120
gggatcattt atcattccac attcttcttt aagaaatgtg ctaaagagcc acagatgggt    180
cttgatgaaa acaaaggaaa agccatgaag tttctacagc ataattagca tcatcattat    240
tctggctgga gcaattgcac tcatcattgg ctttggtatt tcagggagac actccatcac    300
agtcactact gtcgcctcag ctgggaacat tggggaggat ggaatcctga gctgcacttt    360
tgaacctgac atcaaacttt ctgatatcgt gatacaatgg ctgaaggaag gtgttttagg    420
cttggtccat gagttcaaag aaggcaaaga tgagctgtcg gagcaggatg aaatgttcag    480
aggccggaca gcagtgtttg ctgatcaagt gatagttggc aatgcctctt gcggctgaa     540 aaacgtgcaa ctcacagatg ctggcaccta caaatgttat atcatcactt ctaaaggcaa    600
ggggaatgct aaccttgagt ataaaactgg agccttcagc atgccggaag tgaatgtgga    660
ctataatgcc agctcagaga ccttgcggtg tgaggctccc cgatggttcc cccagcccac    720
agtggtctgg gcatcccaag ttgaccaggg agccaacttc tcggaagtct ccaataccag    780
ctttgagctg aactctgaga atgtgaccat gaaggttgtg tctgtgctct acaatgttac    840
gatcaacaac acatactcct gtatgattga aaatgacatt gccaaagcaa caggggatat    900
caaagtgaca gaatcggaga tcaaaaggcg gagtcaccta cagctgctaa actcaaaggc    960
ttctctgtgt gtctcttctt tctttgccat cagctgggca cttctgcctc tcagcccttc    1020
cctgatgcta aaataatgtg ccttggccac aaaaaagcat gcaaagtcat tgttacaaca    1080
gggatctaca gaactatttc accaccagat atgaccagtt tttatatttc tgggaggaaa    1140
tgaattcata tctagaagtc tggagtgagc aaacaagagc aagaaacaaa aagaagccaa    1200
aagcagaagg ctccaaatatg aacaagataa atctatcttc aaagacatat tagaagttgg    1260
gaaaataatt catgtgaact agacaagtgt gttaagagtg ataagtaaaa tgcacgtgga    1320
gacaagtgca tccccagatc tcagggacct ccccctgcct gtcacctggg gagtgagagg    1380
acaggatagt gcatgttctt tgtctctgaa ttttttagtt atatgtgctg taatgttgct    1440
ct                                                                   1442

<210> SEQ ID NO 11
<211> LENGTH: 1333
<212> TYPE: DNA
<213> ORGANISM: Homo sapiens

<400> SEQUENCE: 11
caaaatctgg ccccacacac agcaggactg tgggaaggaa ctccctctcc atggcttcct     60
tggggcagat catcttttgg agtattatta acatcatcat catcctggct ggggccatcg    120
tggctttggc atttcaggca agcacttcat cacggtcacg accttcacct cagctggaaa    180
cattggagag gacgggaccc tgagctgcac ttttgaacct gacatcaaac tcaacggcat    240

```
cgtcatccag tggctgaaag aaggcatcaa aggtttggtc cacgagttca agaaggcaa      300 agacgacctc tcacagcagc atgagatgtt cagaggccgc acagcagtgt ttgctgatca      360
ggtggtagtt ggcaatgctt ccctgagact gaaaaacgtg cagctcacgg atgctggcac      420
ctacacatgt tacatccgct cctcaaaagg caagggaat  gcaaaccttg agtataagac      480
cggagccttc agtatgccag agataaatgt ggactataat gccagttcag agagtttacg      540
ctgcgaggct cctcggtggt tcccccagcc cacagtggcc tgggcatctc aagttgacca      600
aggagccaac ttctcagaag tctccaacac cagctttgag ttgaactctg agaatgtgac      660
catgaaggtc gtatctgtgc tctacaatgt cacaatcaac aacacatact cctgtatgat      720
tgaaaacgac attgccaaag ccaccgggga catcaaagtg acagattcag aggtcaaaag      780
gcggagtcag ctgcagttgc tgaactctgg gccttccccg tgtgtttctt cttctgcctt      840
tgtggctggc tgggcactcc tatctctctc ctgttgcctg atgctaagat gaggggccct      900
ggctacacaa aagcatgcaa cgttgctggt ccaacagaat cccggagaac tacagaaata      960 tttcctcaa  gacatgacct agtttatat  ttctagaaga gatgaaatc  atgtctagaa     1020 gtctggagag agcagacagg aacaagatgt ggaaggaaaa caaaagtaac ccacagacac     1080
ccccgatcgg aacaagatgg acctagaaaa taattcaacc aaactagagt atactaagtg     1140
tgctgttaca atgtgtgtag ggtaggtgtc ctcccacatc tcaggggcct cccctggtcc     1200
accagctcct gagttaggat gggctgttat gatgtcactc tgaaggttcc tggatggttc     1260
ctactgccat atactcattt tatattcagc acattaaacc atagtgaatg ctaaaaaaaa     1320
aaaaaaaaaa aaa                                                        1333
```

<210> SEQ ID NO 12
<211> LENGTH: 5
<212> TYPE: PRT
<213> ORGANISM: Mus musculus

<400> SEQUENCE: 12

Gly Tyr Trp Met His
1               5

<210> SEQ ID NO 13
<211> LENGTH: 17
<212> TYPE: PRT
<213> ORGANISM: Mus musculus

<400> SEQUENCE: 13

Thr Ile Phe Pro Gly Asn Ser Asp Thr Asn Tyr Asn Gln Lys Phe Lys
1               5                   10                  15

Gly

<210> SEQ ID NO 14
<211> LENGTH: 8
<212> TYPE: PRT
<213> ORGANISM: Mus musculus

<400> SEQUENCE: 14

Gly Leu Arg Thr Trp Leu Asp Tyr
1               5

<210> SEQ ID NO 15
<211> LENGTH: 11
<212> TYPE: PRT
<213> ORGANISM: Mus musculus

<400> SEQUENCE: 15

Leu Ala Ser Gln Thr Ile Gly Thr Trp Leu Ala
1               5                   10

<210> SEQ ID NO 16
<211> LENGTH: 7
<212> TYPE: PRT
<213> ORGANISM: Mus musculus

<400> SEQUENCE: 16

Ala Ala Thr Ser Leu Ala Asp
1               5

<210> SEQ ID NO 17
<211> LENGTH: 9
<212> TYPE: PRT
<213> ORGANISM: Mus musculus

<400> SEQUENCE: 17

Gln Gln Phe Tyr Thr Thr Pro Trp Thr
1               5

<210> SEQ ID NO 18
<211> LENGTH: 117
<212> TYPE: PRT
<213> ORGANISM: Mus musculus

<400> SEQUENCE: 18

Glu Val Gln Leu Gln Gln Ser Gly Thr Val Leu Ala Arg Pro Gly Ala
1               5                   10                  15

Ser Val Glu Met Ser Cys Lys Thr Ser Gly Tyr Thr Phe Thr Gly Tyr
                20                  25                  30

Trp Met His Trp Val Lys Gln Arg Pro Gly Gln Gly Leu Glu Trp Ile
            35                  40                  45

Gly Thr Ile Phe Pro Gly Asn Ser Asp Thr Asn Tyr Asn Gln Lys Phe
        50                  55                  60

Lys Gly Lys Ala Lys Leu Thr Ala Val Thr Ser Ala Asn Thr Ala Tyr
65                  70                  75                  80

Met Asp Leu Ser Ser Leu Ser Asn Asp Ser Ala Val Tyr Tyr Cys
                85                  90                  95

Thr Met Gly Leu Arg Thr Trp Leu Asp Tyr Trp Gly Gln Gly Thr Leu
                100                 105                 110

Val Thr Val Ser Ala
            115

<210> SEQ ID NO 19
<211> LENGTH: 107
<212> TYPE: PRT
<213> ORGANISM: Mus musculus

<400> SEQUENCE: 19

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
                20                  25                  30

Leu Ala Trp Tyr Gln Gln Lys Pro Gly Lys Ser Pro Gln Leu Leu Ile
            35                  40                  45

Tyr Ala Ala Thr Ser Leu Ala Asp Gly Val Pro Ser Arg Phe Ser Gly
        50                  55                  60

-continued

```
Ser Ala Ser Gly Thr Lys Phe Ser Phe Lys Ile Ser Ser Leu Gln Ala
 65                  70                  75                  80

Glu Asp Phe Val Ser Tyr Tyr Cys Gln Gln Phe Tyr Thr Thr Pro Trp
                 85                  90                  95

Thr Phe Gly Gly Gly Thr Asn Leu Glu Ile Lys
                100                 105

<210> SEQ ID NO 20
<211> LENGTH: 5
<212> TYPE: PRT
<213> ORGANISM: Mus musculus

<400> SEQUENCE: 20

Thr Tyr Asn Met His
1               5

<210> SEQ ID NO 21
<211> LENGTH: 17
<212> TYPE: PRT
<213> ORGANISM: Mus musculus

<400> SEQUENCE: 21

Ala Ile Tyr Pro Ala Asn Gly Asp Thr Ser Tyr Asn Gln Lys Phe Lys
1               5                   10                  15

Gly

<210> SEQ ID NO 22
<211> LENGTH: 14
<212> TYPE: PRT
<213> ORGANISM: Mus musculus

<400> SEQUENCE: 22

Cys Gly Phe Tyr Asp Asp Tyr Tyr Asp Trp Tyr Phe Asp Val
1               5                   10

<210> SEQ ID NO 23
<211> LENGTH: 16
<212> TYPE: PRT
<213> ORGANISM: Mus musculus

<400> SEQUENCE: 23

Arg Ser Ser Gln Ser Leu Val Tyr Ser Asn Gly Asn Thr His Leu His
1               5                   10                  15

<210> SEQ ID NO 24
<211> LENGTH: 7
<212> TYPE: PRT
<213> ORGANISM: Mus musculus

<400> SEQUENCE: 24

Lys Val Ser Asn Arg Phe Ser
1               5

<210> SEQ ID NO 25
<211> LENGTH: 9
<212> TYPE: PRT
<213> ORGANISM: Mus musculus

<400> SEQUENCE: 25

Cys Gln Ser Thr His Val Pro Tyr Thr
1               5

<210> SEQ ID NO 26
```

<211> LENGTH: 123
<212> TYPE: PRT
<213> ORGANISM: Mus musculus

<400> SEQUENCE: 26

Gln Ala Tyr Leu Gln Gln Ser Gly Ala Glu Leu Val Arg Pro Gly Ala
1               5                   10                  15

Ser Val Lys Met Ser Cys Lys Ala Ser Gly His Thr Phe Thr Thr Tyr
            20                  25                  30

Asn Met His Trp Val Lys Gln Thr Pro Arg Gln Gly Leu Glu Trp Ile
        35                  40                  45

Gly Ala Ile Tyr Pro Ala Asn Gly Asp Thr Ser Tyr Asn Gln Lys Phe
    50                  55                  60

Lys Gly Lys Ala Thr Leu Thr Val Asp Glu Ser Ser Ser Thr Ala Tyr
65                  70                  75                  80

Met Gln Leu Ser Ser Leu Thr Ser Glu Asp Ser Ala Val Tyr Leu Cys
                85                  90                  95

Ala Arg Cys Gly Phe Tyr Asp Asp Tyr Tyr Asp Trp Tyr Phe Asp Val
            100                 105                 110

Trp Gly Thr Gly Thr Thr Val Thr Val Ser Ser
        115                 120

<210> SEQ ID NO 27
<211> LENGTH: 112
<212> TYPE: PRT
<213> ORGANISM: Mus musculus

<400> SEQUENCE: 27

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asn Gly Asn Thr His Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Cys Gln Ser
                85                  90                  95

Thr His Val Pro Tyr Thr Phe Gly Gly Gly Thr Lys Leu Glu Ile Lys
            100                 105                 110

<210> SEQ ID NO 28
<211> LENGTH: 5
<212> TYPE: PRT
<213> ORGANISM: Mus musculus

<400> SEQUENCE: 28

Asn Phe Gly Val His
1               5

<210> SEQ ID NO 29
<211> LENGTH: 16
<212> TYPE: PRT
<213> ORGANISM: Mus musculus

<400> SEQUENCE: 29

Val Ile Trp Ser Gly Gly Ser Thr Asp Tyr Asn Ala Leu Phe Ile Ser

-continued

```
1               5                   10                  15

<210> SEQ ID NO 30
<211> LENGTH: 9
<212> TYPE: PRT
<213> ORGANISM: Mus musculus

<400> SEQUENCE: 30

Asn Arg Val Gly Arg Leu Leu Asp Ser
1               5

<210> SEQ ID NO 31
<211> LENGTH: 11
<212> TYPE: PRT
<213> ORGANISM: Mus musculus

<400> SEQUENCE: 31

Lys Ala Ser Gln Asn Val Asp Thr Val Val Ala
1               5                   10

<210> SEQ ID NO 32
<211> LENGTH: 7
<212> TYPE: PRT
<213> ORGANISM: Mus musculus

<400> SEQUENCE: 32

Ser Ala Ser Arg Arg Tyr Ile
1               5

<210> SEQ ID NO 33
<211> LENGTH: 8
<212> TYPE: PRT
<213> ORGANISM: Mus musculus

<400> SEQUENCE: 33

Gln Gln Tyr Ser Thr Asn Pro Thr
1               5

<210> SEQ ID NO 34
<211> LENGTH: 117
<212> TYPE: PRT
<213> ORGANISM: Mus musculus

<400> SEQUENCE: 34

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ala Asn Phe
                20                  25                  30

Gly Val His Trp Val Arg Gln Ser Pro Gly Lys Gly Leu Glu Trp Leu
            35                  40                  45

Gly Val Ile Trp Ser Gly Gly Ser Thr Asp Tyr Asn Ala Leu Phe Ile
        50                  55                  60

Ser Arg Leu Ser Ile Ser Lys Asp Ile Ser Lys Ser Gln Val Phe Phe
65                  70                  75                  80

Lys Met Asn Ser Leu Gln Ala Asp Asp Thr Ala Ile Tyr Tyr Cys Val
                85                  90                  95

Arg Asn Arg Val Gly Arg Leu Leu Asp Ser Trp Gly Gln Gly Thr Thr
            100                 105                 110

Leu Thr Val Ser Ser
        115
```

```
<210> SEQ ID NO 35
<211> LENGTH: 106
<212> TYPE: PRT
<213> ORGANISM: Mus musculus

<400> SEQUENCE: 35

Asp Ile Val Met Thr Gln Ser Gln Lys Val Met Ser Thr Thr Val Gly
1               5                   10                  15

Asp Arg Val Thr Ile Thr Cys Lys Ala Ser Gln Asn Val Asp Thr Val
            20                  25                  30

Val Ala Trp Tyr Gln Gln Lys Pro Gly Gln Ser Pro Lys Leu Leu Ile
        35                  40                  45

His Ser Ala Ser Arg Arg Tyr Ile Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Ser Thr Asn Pro Thr
                85                  90                  95

Phe Gly Ala Gly Thr Met Leu Glu Leu Lys
            100                 105

<210> SEQ ID NO 36
<211> LENGTH: 5
<212> TYPE: PRT
<213> ORGANISM: Mus musculus

<400> SEQUENCE: 36

Asp Phe Thr Ile His
1               5

<210> SEQ ID NO 37
<211> LENGTH: 17
<212> TYPE: PRT
<213> ORGANISM: Mus musculus

<400> SEQUENCE: 37

Tyr Ile Tyr Pro Gly Asn Asp Asn Thr Lys Tyr Asn Glu Lys Phe Lys
1               5                   10                  15

Gly

<210> SEQ ID NO 38
<211> LENGTH: 6
<212> TYPE: PRT
<213> ORGANISM: Mus musculus

<400> SEQUENCE: 38

Asn Gly Asn Tyr Asp Tyr
1               5

<210> SEQ ID NO 39
<211> LENGTH: 16
<212> TYPE: PRT
<213> ORGANISM: Mus musculus

<400> SEQUENCE: 39

Arg Ser Ser Gln Ser Leu Val His Ser Asp Gly Asn Thr Tyr Leu His
1               5                   10                  15

<210> SEQ ID NO 40
<211> LENGTH: 7
<212> TYPE: PRT
<213> ORGANISM: Mus musculus
```

```
<400> SEQUENCE: 40

Lys Val Ser Asn Arg Phe Ser
1               5

<210> SEQ ID NO 41
<211> LENGTH: 9
<212> TYPE: PRT
<213> ORGANISM: Mus musculus

<400> SEQUENCE: 41

Ser Gln Ser Thr His Val Pro Leu Thr
1               5

<210> SEQ ID NO 42
<211> LENGTH: 115
<212> TYPE: PRT
<213> ORGANISM: Mus musculus

<400> SEQUENCE: 42

Gln Val Gln Leu Gln Gln Ser Asp Ala Glu Leu Val Thr Pro Gly Ala
1               5                   10                  15

Ser Val Lys Ile Ser Cys Lys Val Ser Gly Tyr Ile Phe Thr Asp Phe
                20                  25                  30

Thr Ile His Trp Met Lys Gln Arg Pro Glu Gln Gly Leu Glu Trp Ile
            35                  40                  45

Gly Tyr Ile Tyr Pro Gly Asn Asp Asn Thr Lys Tyr Asn Glu Lys Phe
        50                  55                  60

Lys Gly Lys Ala Thr Leu Thr Ala Asp Lys Ser Ser Thr Ala Asn
65                  70                  75                  80

Met Gln Leu Asn Ser Leu Thr Ser Glu Asp Ser Ala Val Tyr Phe Cys
                85                  90                  95

Ala Arg Asn Gly Asn Tyr Asp Tyr Trp Gly Gln Gly Thr Thr Leu Thr
                100                 105                 110

Val Ser Ser
        115

<210> SEQ ID NO 43
<211> LENGTH: 112
<212> TYPE: PRT
<213> ORGANISM: Mus musculus

<400> SEQUENCE: 43

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asp Gly Asn Thr Tyr Leu His Trp Asn Leu Gln Arg Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
                100                 105                 110
```

METHODS OF TREATING CONDITIONS WITH ANTIBODIES THAT BIND B7-H4

REFERENCE TO SEQUENCE LISTING

The present application is being filed along with a Sequence Listing in electronic format. The Sequence Listing is provided as a file entitled JOUTH002NP.TXT, created Apr. 20, 2017, which is 29,011 bytes in size. The information in the electronic format of the Sequence Listing is incorporated herein by reference in its entirety.

FIELD OF THE INVENTION

Provided herein are embodiments relating to therapeutic applications of B7-H4 antibodies.

BACKGROUND

According to the World Health Organization, cancer is a global pandemic that causes nearly 7 million deaths each year worldwide. That number is expected to reach 10 million by the year 2020. Traditionally, cancer is treated using a variety of modalities including surgery, radiation therapy, and chemotherapy. The choice of treatment depends upon the type, location, and dissemination of the cancer. However, these modalities have proven to be relatively ineffective.

B7-1 and B7-2 belong to the B7 Superfamily To date, there are ten known members of the B7 superfamily: B7.1 (CD80), B7.2 (CD86), the inducible co-stimulator ligand (ICOS-L/B7-H2), the programmed death-1 ligand (PD-L1/B7-H1), the programmed death-2 ligand (PD-L2/B7-DC), B7-H3 (CD276), B7-H4 (B7x/B7-S1), B7-H5 (Vista), natural killer cell cytotoxicity receptor 3 ligand (NCR3-LG1/B7-H6), and HERV-H LTR-associating protein 2 (HHLA2/B7-H7) all of which regulate T-cell activation and tolerance. See Greenwald, R. J. et al. The B7 family revisited. Ann. Rev. Immunol. (2005) 23:515-548; Korman, A. J. et al. Adv. Immunol. (2007) 90:297-339; Zang, X. et al. Clin Cancer Res (2007) 13(18):5271-5279; Agarwal, A. et al. Curr. Opin. Organ Transplant. (2008) 13:366-372; Wang, L. et al. J. Exp. Med. (2011) 208(3):577-592; and Zhao, R. et al., HHLA2 is a member of the B7 family and inhibits human CD4 and CD8 T-cell function, PNAS (2013).

B7 superfamily members also belong to the immunoglobulin superfamily and contain an immunoglobulin-V-like (IgV) and an immunoglobulin-C-like (IgC) domain. See Sharpe, A. H. et al., The B7-CD28 Superfamily, Nature Rev. Immunol. (2002) 2:116-126. The IgV and IgC domains of B7 superfamily members are each encoded by single exons, with additional exons encoding leader sequences, transmembrane and cytoplasmic domains. The cytoplasmic domains are short, ranging in length from 19 to 62 amino-acid residues and can be encoded by multiple exons. See Collins, M. et al., Genome Biol. (2005) 6:223.1-223.7. Members of the B7 family are predicted to form back-to-back, non-covalent homodimers at the cell surface, and such dimers have been reported for B7-1 (CD80) and B7-2 (CD86). See Greene, J. L. J. Biol. Chem. (1996) 271:26762-26771; Ikemizu, S. et al. Immunity (2000) 12:51-60; and Greenwald R. J. Annu. Rev. Immunol. (2005) 23:515-548. Further, alternative spliced forms have been observed for various B7 members, including PD-L2, ICOS and B7-H3. See He, X-H. Acta Biochimica et Biophysica Sinica (2004), 36(4):284-289; Hofmeyer, K. A. PNAS (2008) 105(30):10277-10278; and Carreno, B. M. Annu. Rev. Immunol. (2002) 20:29-53.

B7-H4 (also known as B7x or B7S1) is a type I transmembrane protein belonging to the B7 superfamily B7-H4 is hypothesized to be a regulator of antitumor responses, and exploited by tumors to evade immune clearance. The mechanism(s) of action of B7-H4 signaling in T and B-cell activation, and the role of B7-H4 in modulating anti-tumor immune responses is still being unraveled.

SUMMARY OF SOME EMBODIMENTS

In some embodiments, provided herein are methods of treating a cancer. The method comprises providing a B7-H4 antibody in a therapeutically effective amount to a cancer in a subject, where the cancer is as least one of: a) not responsive to a PD-1 therapy, b) expresses a low level PD-L1, c) also receiving a therapeutically effective amount of a PD-1 therapy, or d) no longer responsive to a PD-1 therapy.

In some embodiments, provided herein are methods that comprise administering a B7-H4 antibody to a subject that has a cancer that expresses a high level of B7-H4 and a low level of PD-L1. The B7-H4 antibody reduces B7-H4 activity in the subject.

In some embodiments, provided herein are methods where the subject does not adequately respond to a PD-1 therapy. The method comprises reducing B7-H4 activity in a subject by administering a B7-H4 antibody to the subject.

In some embodiments, provided herein are methods that comprise administering to a subject having a cancer a B7-H4 antibody that reduces B7-H4 activity where the cancer expresses B7-H4 at a high level, the cancer expresses PD-L1 at a high level, and the subject does not (or no longer) respond(s) to a PD-1 therapy.

In some embodiments, provided herein are methods for administering a B7-H4 antibody to a cancer, where the cancer expresses B7-H4 at a high level, and either a) expresses PD-L1 at a low level or b) PD-L1 is present and the cancer is not (or is no longer) responsive to a PD-1 therapy.

In some embodiments, provided herein are methods of administering a B7-H4 antibody to a tissue, where the tissue expresses B7-H4 at a high level. An amount of the B7-H4 antibody is sufficient to reduce B7-H4 activity in the tissue and the tissue does not express PD-L1 at a high level.

In some embodiments, provided herein are methods that comprise providing a subject receiving PD-1 therapy and administering a therapeutically effective amount of a B7-H4 antibody to the subject.

In some embodiments, provided herein are methods that comprise administering to a subject a therapeutically effective amount of a B7-H4 antibody and administering to the subject a therapeutically effective amount of a PD-1 antibody.

In some embodiments, any of the methods provided herein can be performed by an antagonist B7-H4 antibody.

In some embodiments, a method of treating a cancer, is provided and comprises providing a B7-H4 antibody in a therapeutically effective amount to a cancer in a subject, wherein a) the cancer is not responsive to a PD-1 therapy, b) the cancer expresses a low level PD-L1, c) the cancer is also receiving a therapeutically effective amount of a PD-1 therapy, or d) the cancer is no longer responsive to a PD-1 therapy.

In some embodiments, a composition is provided comprising a B7H4 ADCC antibody or a B7H4 antibody conjugated to a therapeutically effective drug; and a PD-1 antibody.

In some embodiments, a method of treating a cancer is provided comprising providing a B7-H4 antibody in a therapeutically effective amount to a cancer in a subject, wherein: a) the cancer is not responsive to a PD-1 therapy, b) the cancer expresses a low level PD-L1, or c) the cancer is also receiving a therapeutically effective amount of a PD-1 therapy.

BRIEF DESCRIPTION OF THE DRAWINGS

FIG. 2A shows a lack of correlation between B7-H4 and chemokine signature. FIG. 2B shows a correlation between PD-L1 expressions and chemokine signature.

FIG. 3 is a series of panels showing an evaluation of B7-H4 staining intensity in breast cancer. Representative images showing the rage of B7-H4 IHC staining and scoring in breast cancer. In some embodiments, these can be used to determine "high" vs. "low" or "negative", "weak", "moderate", and/or "strong" staining and/or presence/expression of B7-H4.

FIG. 4 is a FACs analysis showing a correlation between B7-H4 IHC and B7-H4 flow cytometry in ovarian cancer samples.

FIG. 6 is a series of panels showing representative images for PD-L1 staining in NSCLC. In some embodiments, these can be used to determine "high" vs. "low" or "negative", "weak", "moderate", and/or "strong" staining and/or presence and/or expression of PD-L1.

FIG. 7 shows a series of depictions of PD-L1 and B7-H4 staining in breast, HNSCC, ovarian, and lung cancer samples. The total number of samples from each tumor type included in the analysis is indicated. The percentage of samples that are positive for B7-H4 alone or PD-L1 alone are indicated. The samples that were positive for both are indicated by the intersection of the two circles.

FIGS. 10A-10D show the amino acid sequences of four isoforms of human B7-H4, including: isoform 1 (FIG. 10A or SEQ ID NO:1); isoform 2 (FIG. 10B or SEQ ID NO:2); isoform 3 (FIG. 10C or SEQ ID NO:3); and isoform 4 (FIG. 10D or SEQ ID NO:4).

FIG. 10E shows the amino and nucleic acid sequence of murine B7-H4 (SEQ ID NO: 5).

FIG. 11A depicts SKBR3 cells naturally expressing B7-H4 and HER-2. FIG. 11B depicts MX1 cells expressing B7-H4.

FIGS. 11C-11F depict the CDR and heavy and light chain variable sequences of the constructs tested in FIGS. 11A and 11B.

DETAILED DESCRIPTION OF SOME EMBODIMENTS

Figure 1:
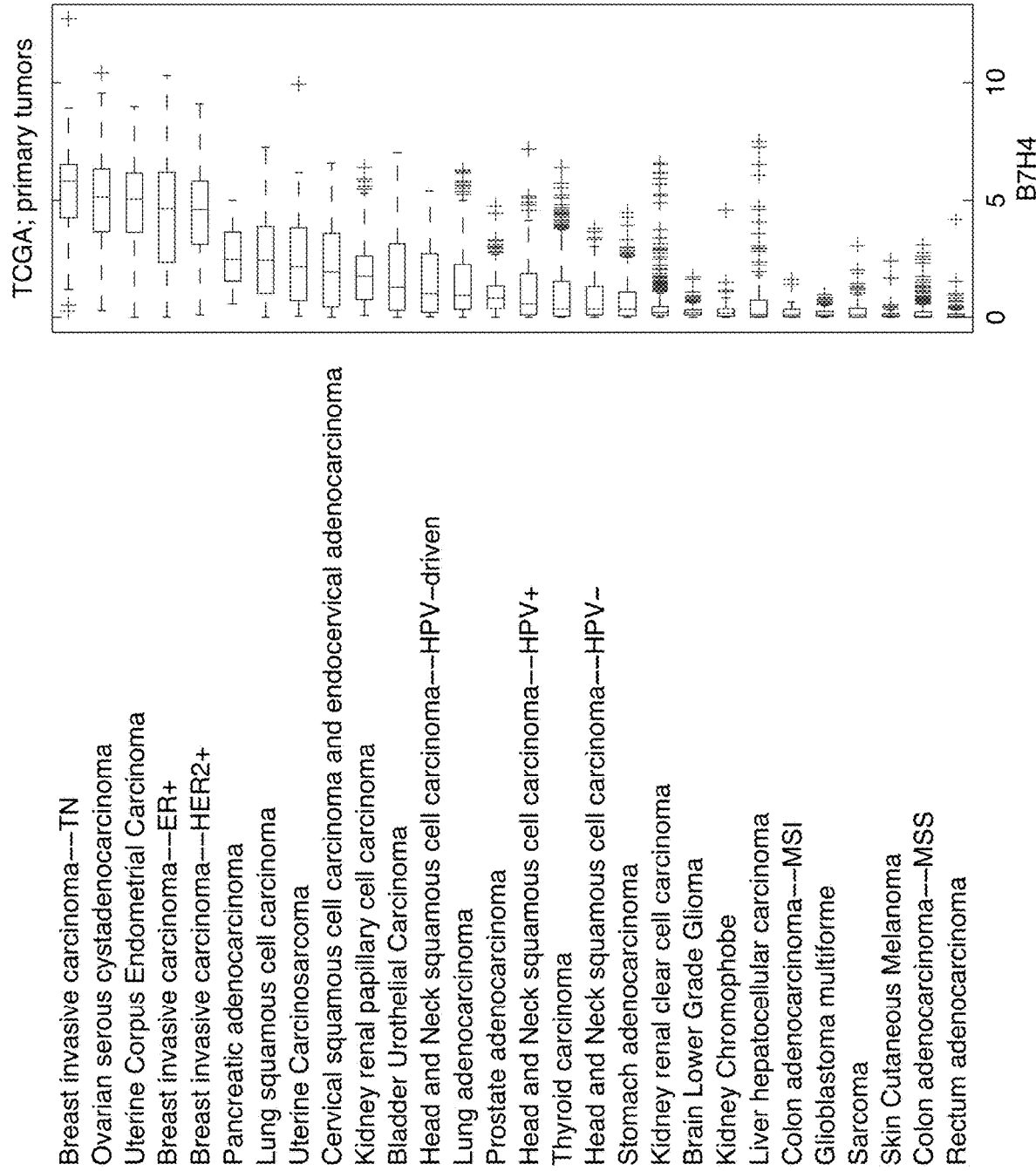
FIG. 1 is a graph showing levels of B7-H4 mRNA across multiple human tumors. Mean intensity and 75% confidence intervals of normalized B7-H4 mRNA levels across various indications are plotted. Samples with intensities outside of the 75% confidence range are indicated (+). All "+" are to the right of the area of the "whiskers".

Embodiments provided herein relate to antibodies to B7-H4 and their use in various methods to determine and/or deliver appropriate cancer therapies. The presence or absence of B7-H4 in a cancer can indicate a specific treatment for the subject. In some embodiments, B7-H4 expression, when combined with a lack of PD-L1 expression, indicates a cancer that can be treated with a B7-H4 antibody (in place of, or in addition, a PD-1 therapy).

In some embodiments, B7-H4 expression in a subject who does not respond to PD-1 related therapies (but does have PD-L1 expression) indicates that the subject has a cancer that can be treated by administering a B7-H4 antibody.

In some embodiments, B7-H4 expression in a subject who no longer responds to PD-1 related therapies (but does have PD-L1 expression) indicates that the subject has a cancer that can be treated by administering a B7-H4 antibody.

In some embodiments, B7-H4 expression in a cancer that also expresses PD-L1 can indicate a cancer that can be treated with a combination of a B7-H4 antibody and a PD-L1 antibody.

The following discussion provides a set of definitions for the terms used herein (and various embodiments), followed by a detailed discussion of the various methods and compositions relating to B7-H4, and concluding with a set of examples.

Definitions and Various Embodiments

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

As is understood by one skilled in the art, reference to "about" a value or parameter herein includes (and describes) embodiments that are directed to that value or parameter per se. For example, description referring to "about X" includes description of "X".

The phrase "reference sample", "reference cell", or "reference tissue", denote a sample with at least one known characteristic that can be used as a comparison to a sample with at least one unknown characteristic. In some embodiments, a reference sample can be used as a positive or negative indicator. A reference sample can be used to establish a level of protein and/or mRNA that is present in, for example, healthy tissue, in contrast to a level of protein and/or mRNA present in the sample with unknown characteristics. In some embodiments, the reference sample comes from the same subject, but is from a different part of the subject than that being tested. In some embodiments, the reference sample is from a tissue area surrounding or adjacent to the cancer. In some embodiments, the reference sample is not from the subject being tested, but is a sample from a subject known to have, or not to have, a disorder in question (for example, a particular cancer or B7-H4 related disorder). In some embodiments, the reference sample is from the same subject, but from a point in time before the subject developed cancer. In some embodiments, the reference sample is from a benign cancer sample (for example, benign breast cancer sample), from the same or a different subject. When a negative reference sample is used for comparison, the level of expression or amount of the molecule in question in the negative reference sample will indicate a level at which one of skill in the art will appreciate, given the present disclosure, that there is no and/or a low level of the molecule. When a positive reference sample is used for comparison, the level of expression or amount of the molecule in question in the positive reference sample will indicate a level at which one of skill in the art will appreciate, given the present disclosure, that there is a level of the molecule.

A sample that expresses a "low level of PD-L1" or expresses "PD-L1 at a low level", denotes that the level of PD-L1 is under the level of expression for a cancer that is normally indicated for treatment with a PD-1 therapy. In some embodiments, a "low level of PD-L1" is one in which less than 1% of the cells in the tumor have membrane staining. In some embodiments a "low level" in regard to PD-L1 is less than 1% staining, for example, 0.9, 0.8, 0.7, 0.6, 0.5, 0.4, 0.3, 0.2, 0.1% or 0% of the cells of the tumor are stained. In some embodiments, the protein expression levels can be measured by chromogenic IHC or immunofluorescence IHC (Aqua scoring). In some embodiments, PD-L1 staining of 5% or less (including tumor and/or immune cells) can indicate that a sample expresses a "low level of PD-L1". In some embodiments, other levels can be used, depending upon the assay, for example, for Merck (22C3) a threshold can be much higher (PS score>50% in viable tumor cells). BMS is currently employing a 5% cut-off and Genentech uses a TC3 (50% tumor cell staining) or IC3 (10% in immune cell staining) Unless indicated otherwise herein, a 5% threshold (beneath 5% is a low level of PD-L1) is preferred herein.

In some embodiments, an "elevated level of PD-L1" or "expresses PD-L1 at an elevated level" denotes the level of PD-L1 that is adequate to indicate to one of skill in the art that the cancer can be treated by a PD-1 therapy. In some embodiments, an "elevated level of PD-L1" is one in which 1% of the cells in the tumor or more have membrane staining. In some embodiments a "high level" in regard to PD-L1 is 1% or more staining, for example, 1, 5, 10, 20, 30, 40, 50, 60, 70, 80, 90, or 100% of the cells of the tumor are stained. In some embodiments, the protein expression levels can be measured by chromogenic IHC, or immunofluorescence IHC (Aqua scoring).

A sample that expresses no PD-L1 can also be said to "express a low level of PD-L1". Thus, no PD-L1 is encompassed within the phrase. A cell that expresses a level of PD-L1 that is indistinguishable from a cell that expresses no PD-L1 is a cell that expresses a "low level of PD-L1". In some embodiments, a low level of PD-L1 is within the background staining levels of non-cancerous cells. In some embodiments, a sample that is PD-L1 "negative" has a low level of PD-L1. In some embodiments, PD-L1 staining is negative when no or less than 1% of the cells have membrane staining for PD-L1. As noted above, this value will vary according to the assay and in some embodiments, low level is less than 5% staining.

In some embodiments, PDL1 staining is positive when 1% or more of the cells have membrane staining for PDL1. In some embodiments, a sample that is PDL1 positive displays at least mild, moderate, and/or strong cell staining (based on membrane expression of PD-L1). As used herein, the term "negative" will encompass (and can be used interchangeably with) "low level" and the term "positive" will encompass (and can be used interchangeably with) mild, moderate, and/or strong levels of staining and/or membrane expression. As used herein, staining is an indicator of protein level. As noted above, this value will vary according to the assay and in some embodiments, a positive level is above 5% staining.

An "elevated level of B7-H4" or "expresses B7-H4 at an elevated level" denotes that the level of B7-H4 is higher than in tissue surrounding the cancer. In some embodiments, an "elevated level of B7-H4" is one in which 5% or more of the cells in the tumor have membrane staining. In some embodiments a "high level" in regard to B7-H4 is 5% or more staining, for example, 5, 10, 20, 30, 40, 50, 60, 70, 80, 90, or 100% of the cells of the tumor are stained. In some embodiments, the protein expression levels can be measured by chromogenic IHC, or immunofluorescence IHC (Aqua scoring).

A "low level of B7-H4" or "expresses B7-H4 at a low level" denotes a level of B7-H4 that is lower than that present in a B7-H4 tumor. In some embodiments, this denotes a level that is less than 5% of the cells have membrane staining. In some embodiments, the expression levels can be measured by IHC. In some embodiments a "low level" in regard to B7-H4 is less than 5% staining, for example, 4.9, 4.5, 4, 3, 2, 1, 0.9, 0.8, 0.7, 0.6, 0.5, 0.4, 0.3, 0.2, 0.1% or less of the cells of the tumor are stained.

A cell that expresses no B7-H4 can also be described as expressing a "low level of B7-H4". Thus, the phrase "expresses a low level of B7-H4) encompasses no B7-H4. A cell that expresses a level of B7-H4 that is indistinguishable from a cell that expresses no B7-H4 is a cell that expresses a "low level of B7-H4". In some embodiments, a low level of B7-H4 is within the background staining levels of non-cancerous cells. In some embodiments, a sample that is B7-H4 "negative" has a low level of B7-H4. In some embodiments, B7-H4 staining is negative when no or less than 5% of the cells have membrane staining for B7-H4.

In some embodiments, B7-H4 staining is positive when 5% or more of the cells have membrane staining for B7-H4. In some embodiments, a sample that is B7-H4 positive displays at least mild, moderate, and/or strong cell staining (based on membrane expression of PD-L1). As used herein, the term "negative" will encompass (and can be used interchangeably with) "low level" and the term "positive" will encompass (and can be used interchangeably with) mild, moderate, and/or strong levels of staining and/or membrane expression. As used herein, staining is an indicator of protein level.

A "PD-1 therapy" encompasses any therapy that modulates PD-1 binding to PD-L1 and/or PD-L2. PD-1 therapies can, for example, directly interact with PD-1 and/or PD-L1. A PD-1 therapy can include a molecule that directly binds to and/or influences the activity of PD-1. A PD-1 therapy can include a molecule that directly binds to and/or influences the activity of PDL1. Thus, an antibody that binds to PD-1 or PDL1 to block the interaction of PD-1 to PDL1 would be characterized as a PD-1 therapeutic. When a desired subtype of PD-1 therapy is intended, it will be designated by the phrase "PD-1 specific" for a therapy involving a molecule that interacts directly with PD-1, or "PDL1 specific" for a molecule that interacts directly with PD-L1, as appropriate. Unless designated otherwise, all disclosure contained herein regarding PD-1 therapy applies to PD-1 therapy generally, as well as PD-1 specific and/or PDL1 specific therapies. Examples of PD-1 therapy include Nivolumab (BMS-936558, MDX-1106, ONO-4538); Pidilizumab, Lambrolizumab/pembrolizumab (KEYTRUDA, MK-3475); durvalumab; RG-7446; MSB-0010718C; AMP-224; BMS-936559 (an anti-PDL1 antibody); AMP-514; MDX-1105; ANB-011; anti-LAG-3/PD-1; anti-PD-1 Ab (CoStim); anti-PD-1 Ab (Kadmon Pharm.); anti-PD-1 Ab (Immunovo); anti-TIM-3/PD-1 Ab (AnaptysBio); anti-PDL1 Ab (CoStim/Novartis); MEDI-4736 (an anti-PDL1 antibody, Medimmune/AstraZeneca); RG7446/MPDL3280A (an anti-PDL1 antibody, Genentech/Roche); KD-033, PD-1 antagonist (Agenus); STI-A1010; STI-A1110; TSR-042; and other antibodies that are directed against programmed death-1 (PD-1) or programmed death ligand 1 (PD-L1).

The terms "benefit", "clinical benefit", "responsiveness", and "therapeutic responsiveness" as used herein in the context of benefiting from or responding to administration of a therapeutic agent, can be measured by assessing various endpoints, e.g., inhibition, to some extent, of disease progression, including slowing down and complete arrest; reduction in the number of disease episodes and/or symptoms; reduction in lesion size; inhibition (that is, reduction, slowing down or complete stopping) of disease cell infiltration into adjacent peripheral organs and/or tissues; inhibition (that is, reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, for example, progression-free survival; increased overall survival; higher response rate; and/or decreased mortality at a given point of time following treatment. A subject or cancer that is "non-responsive" or "fails to respond" is one that has failed to meet the above noted requirements to be "responsive".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"B7-H4" as used herein, refers to a protein that is expressed on the surface of antigen-presenting cells and interacts with ligands on T lymphocytes. The protein is also known as V-set domain-containing T-cell activation inhibitor 1, B7-H4, B7S1, B7X, B7h.5, PRO1291, and VCTN1. The protein belongs to the B7 family and is encoded by the VTCN1 gene. B7-H4 is a type I transmembrane protein belonging to the B7 superfamily. It has a signal peptide in the N-terminus, an extracellular domain with IgV- and IgC-like domains, seven sites for N-linked glycosylation, and a hydrophobic/transmembrane region. See Zang, X. B7x: A widely expressed B7 family member that inhibits T-cell activation. PNAS (2003) 100(18):10388-10392. B7-H4 has also been shown to be membrane-bound via glycosyl phosphatidylinositol (GPI)-linkages, making it unique among other known members of the B7 family. See Prasad, D. V. et. al., Immunity (2003). 18(6): 863-873; Zang, X. et. al., PNAS (2003) 100:10388-10392; Choi, I. H. et. al., J Immunol. (2003) 171:4650-4654 and Salceda, S. et. al., Exp. Cell Res. (2005) 306:128-141. FIG. 10E depicts am exemplary amino acid and nucleic acid sequences of B7-H4.

B7-H4 is expressed on the surface of antigen-presenting cells (including on B-cells upon infection with Epstein-Barr Virus), and interacts with ligands/receptors on T lymphocytes to regulate (e.g. inhibit) immune responses. B7-H4 mRNA is widely expressed in the periphery, including in cells of brain, heart, kidney, testes, lung, liver, pancreas, prostate, placenta, uterus, skin, muscle, intestine, stomach, and ovary, although limited protein expression has been observed in these tissues. See Collins, M. et al. The B7 Family Of Immune-Regulatory Ligands, Genome Biol. (2005) 6:223.1-223.7; and He, C. et al., Clin. and Develop. Immunol. (2011) 1-8 (Article ID 695834). In contrast, B7-H4 proteins are expressed in a variety of cancers including cancers of ovary, esophagus, kidney, stomach, liver, lung, colon, pancreas, breast, prostate and melanoma. See He, C. et al., Clin. and Develop. Immunol. (2011) 1-8 (Article ID 695834). Kryczek, I. et al., J. Exp. Med. (2006) 203(4): 871-881; and Kryczek, I. et al., Cancer Research. (2007) 67(18): 8900-8905.

B7-H4 mRNA is widely expressed in both murine and human peripheral tissues. By contrast, B7-H4 protein expression is generally absent in most somatic tissues, except in human epithelial cells of the female genital tract, kidney, lung, and pancreas, and in mice hematopoietic cells. See Yi, K. H. et. al., Immunological Reviews (2009) 229: 145-151; Sica, G. L. Immunity (2003) 18:849-861; Prasad, D. V. et. al. Immunity (2003) 18:863-873; Choi, I. H. et. al. J. Immunol. (2003) 171:4650-4654.

B7-H4 has been shown to have inhibitory roles in a variety of diseases, including cancer and autoimmune diseases. B7-H4 is not only generally expressed in the cytoplasm, on the membrane, in the serum, and/or ascites in a variety of cancers, including ovary, uterus, breast, pancreas, bladder, prostate, renal, brain, and gastric (see Yu, N. et. al., Inflammation (2013) (PMID: 23605559); Chen, Y. C. et. al., Kidney Int. (2006) 70:2092-2099; Tringler, B. et. al., Gynecol Oncol (2006) 100:44-52; Miyatake, T. et. al., Gynecol Oncol (2007) 106:119-127; Mugler, K. C. et. al. Appl Immunohistochem Mol Morphol (2007) 15:363-370; Awadallah, N. S. et. al. Pancreas (2008) 36:200-206; Liakou, C. I. et. al., Cancer Immun (2007) 7:10; Zang, X. et. al. PNAS (2007) 104:19458-19463; Krambeck, A. E. et. al. PNAS (2006) 103:10391-10396; Crispen, P. L. et. al. Cancer (2008) 113:450-460; Yao, Y. et. al. J Neurooncol. 89:121-129; Jiang, J. et. al., Cancer Immunol Immunother (2010) 59:1707-1714 and Arigami, T. et. al., J Surg Oncol (2010) 102:748-752), but also B7-H4 expression in these cancers his prognostic of worse clinical outcomes. Further soluble B7-H4 is associated with cancer progression. See Thompson, R. H., et. al. Cancer Res (2008) 68:6054-6058.

B7-H4 is not expressed on resting B or T-cells, monocytes, or dendritic cells, but B7-H4 expression can be induced on professional antigen presenting cells (APC) such as dendritic cells, monocytes and macrophages by cytokines such as IL-6 and IL-10. B7-H4 expression can be decreased following GM-CSH and/or IL-4 exposure. Interestingly, B7-H4 expression on tumor cells is unaffected by IL-6, IL-10, GM-CSH and/or IL-4. See Prasad, D. V. R. et. al., Immunity (2003) 18(6): 863-873. Sica, G. L. et al., Immunity (2003) 18(6):849-861; Kryczek, I. et al., J. Exp. Med. (2006) 203(4): 871-881; and Kryczek, I. et al., Cancer Research. (2007) 67(18): 8900-8905; He, C. et al., Clin. and Develop. Immunol. (2011) 1-8 (Article ID 695834). Accordingly it is hypothesized that the signaling pathways that control B7-H4 in APC and tumor cells are different, and that signaling cascade(s) ensuing following B7-H4 receptor-ligand interaction may also be different between APC and tumor cells. The receptor(s) that bind B7-H4 have not been fully characterized. Early work suggests one such receptor would need to be rapidly and transiently up-regulated on T-cells after activation (Loke, P. et al. Emerging Mechanisms Of Immune Regulation: The Extended B7 Family And Regulatory T-cells. Arthritis Res. Ther. (2004) 6:208-214).

B7-H4 inhibits TCR/CD28 signaling events, including phosphorylation of mitogen-activated protein kinases (MAPK), Extracellular signal-regulated kinases (ERK), p38 MAPK, AKT or Protein kinase B (PKB), and c-Jun N-terminal kinases (JNK), resulting in reduced IL-2 production and proliferation, as well as expression of early activation markers such as CD69. See Wang, X. Plos One (2012) 7(1):1-10.

Although B7-H4 is not expressed on resting B-cells, its expression is induced on B-cells following infection with Epstein-Barr virus. This induced B7-H4 expression leads to increased levels of intracellular reactive oxygen species (ROS), expression of Fas ligand, and Fas-mediated, and caspase-dependent apoptosis in association with increased release of cytochrome c, apoptosis-inducing factor (AIF), and EndoG from the mitochondria. See He, C. et. al., Clin. and Develop. Immunol. (2011) (Article ID 695834) and Song, H. et al. Cancer Letters, (2008) 266(2):227-237.

Human B7-H4 is believed to be approximately 282 amino acids long with residues 1-21 encoding a signal peptide; residues 22-259 encoding the B7-H4 extracellular domain; residues 260-280 encoding a transmembrane domain; and residues 281-282 encoding the intracellular portion of B7-H4 (all residue numbers refer to SEQ ID NO: for Q7Z7D3 (Uniprot)). Within the extracellular domain, it is believed that residues 35-146 encode an Ig-like V-type 1 domain; and residues 153-241 encode an Ig-like V-type 2 domain. See 79679 (Entrez); ENSG00000134258 (Ensemble); Q7Z7D3 (UniProt); and NM_024626.3 (human RNA sequence) and NP_078902.2 (human polypeptide sequence) (NCBI), each of which is herein incorporated by reference in its entirety for all purposes. The gene is believed to be located at chromosome 1 (117.69-117.75 Mb). Four isoforms or alternatively spliced forms of the human B7-H4 have been reported: Isoform 1 (FIG. 10A, SEQ ID NO: 1, Q7Z7D3-1), Isoform 2 (FIG. 10B, SEQ ID NO:2, Q7Z7D3-2), Isoform 3 (FIG. 10C, SEQ ID NO: 3, Q7Z7D3-3) and Isoform 4 (FIG. 10D, SEQ ID NO: 4, Q7Z7D3-4).

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a B7-H4 epitope is an antibody that binds this epitope with greater affinity, avidity, more readily, and/or with greater duration than it binds to other B7-H4 epitopes or non-B7-H4 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, "substantially pure" refers to material which is at least 50% pure (that is, free from contaminants), for example, at least 90% pure, at least 95% pure, yet more preferably, at least 98% pure, and most preferably, at least 99% pure.

As used herein, the term "epitope" refers to a site on a target molecule (for example, an antigen, such as a protein, nucleic acid, carbohydrate or lipid) to which an antigen-binding molecule (for example, an antibody, antibody fragment, or scaffold protein containing antibody binding regions) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some embodiments, an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between an antibody residue and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antibody. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antibody specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antibody specific to the epitope binds. It is noted that, in some embodiments, not every one of the residues within the linear epitope need be directly bound (or involved in a bond) with the antibody. In some embodiments, linear epitopes can be from immunizations with a peptide that effectively consisted of the sequence of the linear epitope, or from structural sections of a protein that are relatively isolated from the remainder of the protein (such that the antibody can interact, at least primarily), just with that sequence section.

The term "antibody" herein is used in the broadest sense and encompasses various antibody structures, including but not limited to monoclonal antibodies, polyclonal antibodies, multispecific antibodies (for example, bispecific (such as Bi-specific T-cell engagers) and trispecific antibodies), and antibody fragments so long as they exhibit the desired antigen-binding activity.

The term antibody includes, but is not limited to, fragments that are capable of binding to an antigen, such as Fv, single-chain Fv (scFv), Fab, Fab', di-scFv, sdAb (single domain antibody) and (Fab')$_2$ (including a chemically linked F(ab')$_2$). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. The term antibody also includes, but is not limited to, chimeric antibodies, humanized antibodies, and antibodies of various species such as mouse, human, cynomolgus monkey, etc. Furthermore, for all antibody constructs provided herein, variants having the sequences from other organisms are also contemplated. Thus, if a human version of an antibody is disclosed, one of skill in the art will appreciate how to transform the human sequence based antibody into a mouse, rat, cat, dog, horse, etc. sequence. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, human scFv or a mouse scFv). This denotes the sequences of at least part of the non-CDR regions, rather than the source of the construct.

The term "monoclonal antibody" refers to an antibody of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, and/or the contact definition. Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991)). The AbM definition can include, for example, CDRs (CDR-L1, CDR-L2, CDR-L3, CDR-H1, CDR-H2, and CDR-H3) at amino acid residues 24-34 of L1, 50-56 of L2, 89-97 of L3, H26-H35B of H1, 50-58 of H2, and 95-102 of H3. The Contact definition can include, for example, CDRs (CDR-L1, CDR-L2, CDR-L3, CDR-H1, CDR-H2, and CDR-H3) at amino acid residues 30-36 of L1, 46-55 of L2, 89-96 of L3, 30-35 of H1, 47-58 of H2, and 93-101 of H3. The Chothia definition can include, for example, CDRs (CDR-L1, CDR-L2, CDR-L3, CDR-H1, CDR-H2, and CDR-H3) at amino acid residues 24-34 of L1, 50-56 of L2, 89-97 of L3, 26-32 . . . 34 of H1, 52-56 of H2, and 95-102 of H3. CDRs can also be provided as shown in any one or more of the accompanying figures. With the exception of CDR1 in $V_H$, CDRs generally comprise the amino acid residues that form the hypervariable loops. The various CDRs within an antibody can be designated by their appropriate number and chain type, including, without limitation as: a) CDR-L1, CDR-L2, CDR-L3, CDR-H1, CDR-H2, and CDR-H3; b) CDRL1, CDRL2, CDRL3, CDRH1, CDRH2, and CDRH3; c) LCDR-1, LCDR-2, LCDR-3, HCDR-1, HCDR-2, and HCDR-3; or d) LCDR1, LCDR2, LCDR3, HCDR1, HCDR2, and HCDR3; etc. The term "CDR" is used herein to also encompass HVR or a "hyper variable region", including hypervariable loops. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).)

The term "heavy chain variable region" as used herein refers to a region comprising at least three heavy chain CDRs. In some embodiments, the heavy chain variable region includes the three CDRs and at least FR2 and 1-R3. In some embodiments, the heavy chain variable region includes at least heavy chain HCDR1, framework (FR) 2, HCDR2, FR3, and HCDR3. In some embodiments, a heavy chain variable region also comprises at least a portion of an FR1 and/or at least a portion of an FR4.

The term "heavy chain constant region" as used herein refers to a region comprising at least three heavy chain constant domains, $C_H1$, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an a constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" as used herein refers to a region comprising at least three light chain CDRs. In some embodiments, the light chain variable region includes the three CDRs and at least FR2 and FR3. In some embodiments, the light chain variable region includes at least light chain LVR1, framework (FR) 2, LVR2, FR3, and LVR3. For example, a light chain variable region may comprise light chain CDR1, framework (FR) 2, CDR2, FR3, and CDR3. In some embodiments, a light chain variable region also comprises at least a portion of an FR1 and/or at least a portion of an FR4.

The term "light chain constant region" as used herein refers to a region comprising a light chain constant domain, $C_L$. Nonlimiting exemplary light chain constant regions include λ and κ. Of course, non-function-altering deletions and alterations within the domains are encompassed within the scope of the term "light chain constant region," unless designated otherwise.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

An "acceptor human framework" for the purposes herein is a framework comprising the amino acid sequence of a light chain variable domain ($V_L$) framework or a heavy chain variable domain ($V_H$) framework derived from a human immunoglobulin framework or a human consensus framework, as defined below. An acceptor human framework derived from a human immunoglobulin framework or a human consensus framework can comprise the same amino acid sequence thereof, or it can contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Affinity" refers to the strength of the sum total of noncovalent interactions between a single binding site of a molecule (for example, an antibody) and its binding partner (for example, an antigen). The affinity of a molecule X for its partner Y can generally be represented by the dissociation constant ($K_d$). Affinity can be measured by common methods known in the art (such as, for example, ELISA $K_D$, KinExA and/or surface plasmon resonance devices (such as a BIAcore® device), including those described herein.

The term "$K_D$", as used herein, refers to the equilibrium dissociation constant of an antibody-antigen interaction.

In some embodiments, the "$K_D$," "$K_d$," "Kd" or "Kd value" of the antibody is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µL/minute to achieve approximately 10 response units (RU) of coupled protein. Following the injection of antigen, 1 M ethanolamine is injected to block unreacted groups. For kinetics measurements, serial dilutions of polypeptide, for example, full length antibody, are injected in PBS with 0.05% TWEEN-20™ surfactant (PBST) at 25° C. at a flow rate of approximately 25 µL/min Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_d$) is calculated as the ratio $k_{off}/k_{on}$. See, for example, Chen et al., J. Mol. Biol. 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

In some embodiments, the difference between said two values (for example, $K_d$ values) is substantially the same, for example, less than about 50%, less than about 40%, less than about 30%, less than about 20%, and/or less than about 10% as a function of the reference/comparator value.

In some embodiments, the difference between said two values (for example, $K_d$ values) is substantially different, for example, greater than about 10%, greater than about 20%, greater than about 30%, greater than about 40%, and/or greater than about 50% as a function of the value for the reference/comparator molecule.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) Ann. Biol. Clin. 51:19-26.

The term "$k_{on}$", as used herein, refers to the rate constant for association of an antibody to an antigen. Specifically, the rate constants ($k_{on}$ and $k_{off}$) and equilibrium dissociation constants are measured using Fab antibody fragments (that is, univalent) and B7-H4. "$K_{on}$", "$k_{on}$", "association rate constant", or "ka", are used interchangeably herein. The value indicates the binding rate of a binding protein to its target antigen or the rate of complex formation between an antibody and antigen, shown by the equation: Antibody ("Ab")+Antigen ("Ag")→Ab–Ag.

The term "$k_{off}$", as used herein, refers to the rate constant for dissociation of an antibody from the antibody/antigen complex. $k_{off}$ is also denoted as "$K_{off}$" or the "dissociation rate constant". This value indicates the dissociation rate of an antibody from its target antigen or separation of Ab–Ag complex over time into free antibody and antigen as shown by the equation: Ab+Ag←Ab–Ag.

The term "biological activity" as used herein, includes any biological effect of B7-H4. In certain embodiments, B7-H4 activity includes the ability of B7-H4 to interact or bind to a receptor. In certain embodiments, biological activity of B7-H4 includes any biological activity resulting from B7-H4 signaling.

An agonist B7-H4 antibody is one that increases and/or activates a biological activity of the B7-H4 protein. In some embodiments, the agonist antibody binds to an antigen and increases its biologically activity by at least about 20%, 40%, 60%, 80%, 85% or more.

An "antagonist" or "neutralizing" B7-H4 antibody is one that decreases and/or inactivates a biological activity of the B7-H4 protein. In some embodiments, the neutralizing antibody binds to an antigen and reduces its biologically activity by at least about 20%, 40%, 60%, 80%, 85% 90%, 95%, 99% or more.

An "affinity matured" antibody refers to an antibody with one or more alterations in one or more CDRs compared to a parent antibody which does not possess such alterations, such alterations resulting in an improvement in the affinity of the antibody for antigen.

A "chimeric antibody" as used herein refers to an antibody in which a portion of the heavy and/or light chain is derived from a particular source or species, while at least a part of the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species. The chimeric construct can also be a functional fragment, as noted above.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an antibody fragment, such as Fab, an scFv, a (Fab')$_2$, etc. The term humanized also denotes forms of non-human (for example, murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence of non-human immunoglobulin. Humanized antibodies can include human immunoglobulins (recipient antibody) in which residues from a complementary determining region (CDR) of the recipient are substituted by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody can comprise residues that are found neither in the recipient antibody nor in the imported CDR or framework sequences, but are included to further refine and optimize antibody performance. In general, the humanized antibody can comprise substantially all of at least one, and typically two, variable domains, in which all or substantially all of the CDR regions correspond to those of a non-human immunoglobulin and all or substantially all of the FR regions are those of a human immunoglobulin consensus sequence. In some embodiments, the humanized antibody can also comprise at least a portion of an immunoglobulin constant region or domain (Fc), typically that of a human immunoglobulin. Other forms of humanized antibodies have one or more CDRs (CDR L1, CDR L2, CDR L3, CDR H1, CDR H2, and/or CDR H3) which are altered with respect to the original antibody, which are also termed one or more CDRs "derived from" one or more CDRs from the original antibody. As will be appreciated, a humanized sequence can be identified by its primary sequence and does not necessarily denote the process by which the antibody was created.

An "CDR-grafted antibody" as used herein refers to a humanized antibody in which one or more complementarity determining regions (CDRs) of a first (non-human) species have been grafted onto the framework regions (FRs) of a second (human) species.

A "human antibody" as used herein encompasses antibodies produced in humans, antibodies produced in non-human animals that comprise human immunoglobulin genes, such as XenoMouse® mice, and antibodies selected using in vitro methods, such as phage display (Vaughan et al., 1996, Nature Biotechnology, 14:309-314; Sheets et al., 1998, Proc. Natl. Acad. Sci. (USA) 95:6157-6162; Hoogenboom and Winter, 1991, J. Mol. Biol., 227:381; Marks et al., 1991, J. Mol. Biol., 222:581), wherein the antibody repertoire is based on a human immunoglobulin sequence. The term "human antibody" denotes the genus of sequences that are human sequences. Thus, the term is not designating the process by which the antibody was created, but the genus of sequences that are relevant.

A "functional Fc region" possesses an "effector function" of a native sequence Fc region. Exemplary "effector functions" include Fc receptor binding; C1q binding; CDC; ADCC; phagocytosis; down regulation of cell surface receptors (for example B-cell receptor; BCR), etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, for example, Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, for example, Ghetie and Ward, *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

"Effector functions" refer to biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (for example B-cell receptor); and B-cell activation.

"Human effector cells" are leukocytes which express one or more FcRs and perform effector functions. In some embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T-cells, and neutrophils. The effector cells may be isolated from a native source, for example, from blood.

"Antibody-dependent T-cell-mediated cytotoxicity" and "ADCC" refers to a form of cytotoxicity in which secreted Ig bound onto Fc receptors (FcRs) present on certain cytotoxic cells (for example NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 or 6,737,056 (Presta), may be performed. Useful effector cells for such assays include PBMC and NK cells. Alternatively, or additionally, ADCC activity of the molecule of interest may be assessed in vivo, for example, in an animal model such as that disclosed in Clynes et al. *Proc. Natl. Acad. Sci. (USA)* 95:652-656 (1998). Additional polypeptide variants with altered Fc region amino acid sequences (polypeptides with a variant Fc region) and increased or decreased ADCC activity are described, for example, in U.S. Pat. Nos. 7,923,538, and 7,994,290. An "ADCC antibody" is an antibody that provides for antibody-dependent T-cell-mediated cytotoxicity, for example, the IgG1 antibodues presented in FIG. 11A.

"Complement dependent cytotoxicity" and "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, for example, as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, for example, in U.S. Pat. No. 6,194,551 B1, U.S. Pat. Nos. 7,923,538, 7,994,290 and WO 1999/51642. See also, for example, Idusogie et al., *J. Immunol.* 164: 4178-4184 (2000).

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, for example through Van der Waals forces, or by using a leucine zipper. In the present invention, conjugation particularly refers to the linkage of a therapeutic or diagnostic agent to a polypeptide that is part of an antibody.

The term "antibody drug conjugate" or "ADC" denotes an antibody that is conjugated to a compound or a drug. In some embodiments, the antibody is conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (e.g., a radioconjugate). In some embodiments, the one or more toxin can include, but is not limited to, a calicheamicin, maytansinoids, dolastatins, aurostatins, a trichothecene, and CC1065, and the derivatives of these toxins that have toxin activity. Suitable cytotoxic agents include, but are not limited to, an auristatin including dovaline-valine-dolaisoleunine-dolaproine-phenylalanine (MMAF) and monomethyl auristatin E (MMAE) as well as ester forms of MMAE, a DNA minor groove binding agent, a DNA minor groove alkylating agent, an enediyne, a lexitropsin, a duocarmycin, a taxane, including paclitaxel and docetaxel, a puromycin, a dolastatin, a maytansinoid, and a vinca alkaloid. Specific cytotoxic agents include topotecan, morpholino-doxorubicin, rhizoxin, cyanomorpholino-doxorubicin, dolastatin-10, echinomycin, combretatstatin, chalicheamicin, maytansine, DM-1, DM-4, netropsin. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. Antitubulin agent include dimethylvaline-valine-dolaisoleuine-dolaproine-phenylalanine-p-ph-enylenediamine (AFP), MMAF, MMAE, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, DM-4 or eleutherobin.

A polypeptide variant with "altered" FcR binding affinity or ADCC activity is one which has either enhanced or diminished FcR binding activity and/or ADCC activity compared to a parent polypeptide or to a polypeptide comprising a native sequence Fc region. The polypeptide variant which "displays increased binding" to an FcR binds at least one FcR with better affinity than the parent polypeptide. The polypeptide variant which "displays decreased binding" to an FcR, binds at least one FcR with lower affinity than a parent polypeptide. Such variants which display decreased binding to an FcR may possess little or no appreciable binding to an FcR, for example, 0-20% binding to the FcR compared to a native sequence IgG Fc region.

The polypeptide variant which "mediates antibody-dependent cell-mediated cytotoxicity (ADCC) in the presence of human effector cells more effectively" than a parent antibody is one which in vitro or in vivo is more effective at mediating ADCC, when the amounts of polypeptide variant and parent antibody used in the assay are essentially the same. Generally, such variants will be identified using the in vitro ADCC assay as herein disclosed, but other assays or methods for determining ADCC activity, for example in an animal model etc., are contemplated.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

The phrase "substantially different," as used herein, denotes a sufficiently high degree of difference between two numeric values such that one of skill in the art would consider the difference between the two values to be of statistical significance within the context of the biological characteristic measured by said values. In some embodiments, the two substantially different numeric values differ by greater than about any one of 10%, 20%, 25%, 30%, 35%, 40%, 45%, 50%, 60%, 70%, 80%, 90%, or 100%.

The phrase "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 20%, 25%, 30%, 35%, 40%, 45%, 50%, 60%, 70%, 80%, 90%, or 100% compared to the reference value.

The term "leader sequence" refers to a sequence of amino acid residues located at the N-terminus of a polypeptide that facilitates secretion of a polypeptide from a mammalian cell. A leader sequence can be cleaved upon export of the polypeptide from the mammalian cell, forming a mature protein. Leader sequences can be natural or synthetic, and they can be heterologous or homologous to the protein to which they are attached.

A "native sequence" polypeptide comprises a polypeptide having the same amino acid sequence as a polypeptide found in nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (for example, an extracellular domain sequence), naturally occurring variant forms (for example, alternatively spliced forms) and naturally occurring allelic variants of the polypeptide.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 1. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" or "subject" are used interchangeably herein to refer to an animal; for example a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder.

A "disease" or "disorder" as used herein refers to a condition where treatment is needed and/or desired.

The term "tumor cell", "cancer cell", "cancer", "tumor", and/or "neoplasm", unless otherwise designated, are used herein interchangeably and refer to a cell (or cells) exhibiting an uncontrolled growth and/or abnormal increased cell survival and/or inhibition of apoptosis which interferes with the normal functioning of bodily organs and systems. Included in this definition are benign and malignant cancers, polyps, hyperplasia, as well as dormant tumors or micro-metastases. The terms "cancer" and "tumor" encompass solid and hematological/lymphatic cancers and also encompass malignant, pre-malignant, and benign growth, such as dysplasia. Also, included in this definition are cells having abnormal proliferation that is not impeded (e g immune evasion and immune escape mechanisms) by the immune system (e.g. virus infected cells). Exemplary tumor cells include, but are not limited to: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some embodiments, the term cancer can encompass: a lung cancer, a breast cancer, a head and neck cancer, an ovarian cancer, and/or an endometrial cancer. When desired, the difference between a "cancer" and a "cancer cell" can be denoted by the use of the explicit use of the phrase "cancer cell"; however, the term "cancer" will encompass concepts such as the subject having cancer, and multicellular tumors, as well as single cancer cells.

The term "non-tumor cell" as used herein refers to a normal cells or tissue. Exemplary non-tumor cells include, but are not limited to: T-cells, B-cells, natural killer (NK) cells, natural killer T (NKT) cells, dendritic cells, monocytes, macrophages, epithelial cells, fibroblasts, hepatocytes, interstitial kidney cells, fibroblast-like synoviocytes, osteoblasts, and cells located in the breast, skeletal muscle, pancreas, stomach, ovary, small intestines, placenta, uterus, testis, kidney, lung, heart, brain, liver, prostate, colon, lymphoid organs, bone, and bone-derived mesenchymal stem cells. The term "a cell or tissue located in the periphery" as used herein refers to non-tumor cells not located near tumor cells and/or within the tumor microenvironment.

The term "cells or tissue within the tumor microenvironment" as used herein refers to the cells, molecules, extracellular matrix and/or blood vessels that surround and/or feed a tumor cell. Exemplary cells or tissue within the tumor microenvironment include, but are not limited to: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells; macrophages; neutrophils; and other immune cells located proximal to a tumor. Methods for identifying tumor cells, and/or cells/tissues located within the tumor microenvironment are well known in the art, as described herein, below.

As used herein, the term "tolerance" or "tolerance to a tumor" refers to tumor-induced tolerance and/or immune suppression caused by the tumor. In particular immunological tolerance refers to a state of immune unresponsiveness specific to a particular tumor antigen or a set of tumor antigens. The phrase can refer to decreasing the activity of immune cell populations or subpopulations, as measured using a suitable in vitro, cellular, or in vivo assay to determine "change or modulation" of the activity and/or population of immune cells within the tumor and/or tumor microenvironment. In particular, "change or modulation" can mean increasing decreasing a (relevant or intended) biological activity of a target T-cell subpopulation(s), as measured using a suitable in vitro, cellular or in vivo assay (which will usually depend on the target involved), by at least about 5%, at least about 10%, at least about 20%, at least about 25%, at least about 50%, at least about 60%, at least about 70%, at least about 80%, at least about 90%, or more, inclusive, compared to activity of the target in the same assay under the same conditions but without the presence of an agent.

An "increase or decrease" refers to a statistically significant increase or decrease respectively. As will be clear to the skilled person, "modulating" can also involve effecting a change (which can either be an increase or a decrease) in affinity, avidity, specificity and/or selectivity of a target or antigen, for one or more of its ligands, binding partners, partners for association into a homomultimeric or heteromultimeric form, or substrates; effecting a change (which can either be an increase or a decrease) in the sensitivity of the target or antigen for one or more conditions in the medium or surroundings in which the target or antigen is present (such as pH, ion strength, the presence of co-factors, etc.), compared to the same conditions but without the presence of an antibody, bispecific or multispecific polypeptide agent. This can be determined in any suitable manner and/or using any suitable assay known per se or described herein, depending on the target involved.

As used herein, "an immune response" is meant to encompass cellular and/or humoral immune responses that are sufficient to inhibit or prevent onset or ameliorate the symptoms of disease (for example, cancer or cancer metastasis). "An immune response" can encompass aspects of both the innate and adaptive immune systems.

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

"Ameliorating" means a lessening or improvement of one or more symptoms as compared to not administering a B7-H4 antibody. "Ameliorating" also includes shortening or reduction in duration of a symptom.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

The term "control" refers to a composition known to not contain an analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (for example, analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (for example, severity of disease, progression/nonprogression/improvement, etc.). While the present disclosure may provide exemplary predetermined levels, it is well-known that cutoff values may vary depending on the nature of the immunoassay (for example, antibodies employed, etc.). It further is well within the skill of one of ordinary skill in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) may be generally applicable.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes.

The term "sequentially" is used herein to refer to administration of two or more therapeutic agents where the administration of one or more agent(s) continues after discontinuing the administration of one or more other agent(s). For example, administration of the two or more therapeutic agents are administered with a time separation of more than about a specified number of minutes.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached to an antibody or its analyte to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

Methods and Compositions Relating to B7-H4

The interaction between cancer and the immune system is complex and multifaceted. See de Visser et al., Nat. Rev. Cancer (2006) 6:24-37. While many cancer patients appear to develop an anti-tumor immune response, cancers also develop strategies to evade immune detection and destruction. Recently, immunotherapy has been developed for the treatment and prevention of cancer and other disorders Immunotherapy provides the advantage of cell specificity that other treatment modalities lack. As such, methods for enhancing the efficacy of immune based therapies can be clinically beneficial.

A need has been identified for novel anti-B7-H4 antibodies and methods that modulate B7-H4 activity. For example, to allow for the treatment of cancer, the use of B7-H4 antibodies can be especially advantageous in a variety of specific situations, including, when the cancer expresses a low level of PD-L1, when the subject and/or cancer is nonresponsive to PD-1 therapy, and/or in combination with a PD-1 therapy. These, and additional embodiments are outlined below.

Methods of Treating Diseases Using B7-H4 Antibodies

In some embodiments, the method can comprise administering a B7-H4 antibody to a subject. The subject has a cancer that expresses B7-H4 at a high level. The cancer also expresses a low level of PD-L1. The presence of the antibody reduces B7-H4 activity in the subject.

In some embodiments, the subject can be one that did not adequately respond to a PD-1 therapy. The method comprises reducing B7-H4 activity in the subject by administering a B7-H4 antibody to the subject. The B7-H4 antibody can be administered in an amount that is adequate for therapy.

In some embodiments, the method comprises administering to a subject having a cancer a B7-H4 antibody that reduces B7-H4 activity. The cancer expresses B7-H4 at a high level. The cancer expresses PDL1 at a high level, and the subject does not respond to a PD-1 therapy. In some embodiments, the method comprises administering a B7-H4 antibody to a cancer. The cancer expresses B7-H4 at a high level, and either a) expresses PDL1 at a low level orb) PDL1 is present and the cancer is not responsive to a PD-1 therapy.

In some embodiments, the method comprises administering a B7-H4 antibody to a tissue. The tissue expresses B7-H4 at a high level. The amount of the B7-H4 antibody is sufficient to reduce B7-H4 activity in the tissue. The tissue does not express PDL1 at a high level.

In some embodiments, the method comprises providing a subject receiving PD-1 therapy and administering a therapeutically effective amount of a B7-H4 antibody to the subject. In some embodiments, the method comprises administering to a subject a therapeutically effective amount of a B7-H4 antibody and administering to the subject a therapeutically effective amount of a PD-1 antibody. In some embodiments, the method provides a synergistic response, allowing for more than a merely additive benefit over the use of a PD-1 therapy and a B7-H4 antibody. In some embodiments, the combination of therapies allows for lower doses to be used to avoid adverse side-effects. In some embodiments, the combination of therapies allows for therapeutic effects beyond those achievable by simply having one or the other therapeutic approach in play.

In some embodiments, a method of treating a cancer is provided. The method comprises providing a B7-H4 antibody in a therapeutically effective amount to a cancer in a subject. At least one of the following applies to the cancer: the cancer is not responsive to PD-1 therapy, the cancer expresses a low level of PD-L1, and/or the cancer is also receiving a therapeutically effective amount of PD-1 therapy. In some embodiments, the antibody provides effectiveness through an ADCC mechanism. In some embodiments, the antibody provides effectiveness though an ADC mechanism. In some embodiments, the cancer is at least one of breast or ovarian cancer. In some embodiments, the subject is first identified as having at least one of breast or ovarian cancer. In some embodiments, the subject is identified as having a cancer that is not responsive to PD-1 therapy (and/or no longer responsive to PD-1 therapy). In some embodiments, the subject is identified as having a cancer that expresses a low level of PDL1 (for example, by the assay outlined in Example 10 herein). In some embodiments, the subject is identified as having a cancer that no longer responds to PD-1 therapy. In some embodiments, the subject is also receiving a therapeutically effective amount of PD-1 therapy. In some embodiments, the subject receives an antibody that provides a therapeutic benefit by ADCC. In some embodiments, the antibody is an IgG1 antibody. In some embodiments, the antibody is any one or more of the antibodies provided herein. In some embodiments, the antibody has at least one of the CDRs provided in FIGS. 11C-11F. In some embodiments, the antibody has at least three of the CDRs provided in FIGS. 11C-11F. In some embodiments, the antibody has six of the CDRs provided in FIGS. 11C-11F. In some embodiments, the antibody has six of the CDRs provided in FIG. 11C. In some embodiments, the antibody has six of the CDRs provided in FIG. 11D. In some embodiments, the antibody has six of the CDRs provided in FIG. 11E. In some embodiments, the antibody has six of the CDRs provided in FIG. 11F. In some embodiments, the antibody has at least one of the heavy or light chain variable regions provided in FIGS. 11C-11F. In some embodiments, the antibody has the heavy chain and the light chain variable region provided in FIG. 11C. In some embodiments, the antibody has the heavy chain and the light chain variable region provided in FIG. 11D. In some embodiments, the antibody has the heavy chain and the light chain variable region provided in FIG. 11E. In some embodiments, the antibody has the heavy chain and the light chain variable region provided in FIG. 11F.

In some embodiments, the antibody has a sequence that is at least 95% identical to at least one of the heavy or light chain variable regions provided in FIGS. 11C-11F. In some embodiments, the antibody has a sequence that is at least 95% identical to the heavy chain and the light chain variable region provided in FIG. 11C. In some embodiments, the antibody has a sequence that is at least 95% identical to the heavy chain and the light chain variable region provided in FIG. 11D. In some embodiments, the antibody has a sequence that is at least 95% identical to the heavy chain and the light chain variable region provided in FIG. 11E. In some embodiments, the antibody has a sequence that is at least 95% identical to the heavy chain and the light chain variable region provided in FIG. 11F. In some embodiments, any one of these antibodies binds to B7-H4.

In some embodiments, a method of identifying a subject to receive a B7-H4 therapy is provided. The method comprises testing a cancer sample for a high level of expression of B7-H4. The cancer is one or more of triple negative breast cancer, ovarian cancer, uterine cancer, breast cancer (ER+), or breast cancer (HER2+). The method further comprises comparing a level of B7-H4 expression in the cancer sample to a level of B7-H4 expression in healthy tissue to determine if the level of B7-H4 expression in the cancer sample is higher. If the level of B7-H4 expression is higher in the cancer sample, the subject receives a B7-H4 antagonist. In some embodiments, the B7-H4 antagonist is one or more of the antibodies provided herein (for example, having one or more of the CDRs or variable regions in FIGS. 11C-11F).

In some embodiments, a potential subject to be treated and/or sample to be tested can be assayed for the degree of tumor infiltration of immune T-cells. Tumor infiltration of immune T-cells has been associated with greater immune recognition of the tumor and better prognosis (Galon, et al., Journal of Translational Medicine, 2012). In addition, patients with high levels of immune infiltration show a better response to checkpoint therapies such as anti-PD-1 (Taube et al., Clinical Cancer Res, 2014) Immune infiltration in tumor can be measured by staining for CD8 or CD4 or CD3 or other immune cell markers such as CD45RO. The density of immune infiltrates was scored based on a semi-quantitative scale from 0-3 wherein 0=no immune infiltrate; 1="focal" (mostly perivascular in tumor with some intratumoral expression); 2="moderate" (predominantly observed in the tumor area); 3="severe" (dense immune infiltrates in the tumor area). A detailed quantitative method for measurement of immune cells in the tumor has been developed by Gerome Galon. In addition to immunohistochemical detection, methods to detect mRNA gene expression signatures could also be used to measure immune cell infiltration. A 12 gene chemokine gene signature has been shown to identify T-cell infiltration in melanoma patients (Messina, et al, Scientific Reports, 2012).

In some embodiments, any method for measuring the level of PDL1 can be employed. In some embodiments, such method comprises using the PD-L1 IHC 22C3 pharmDx test (Dako Inc., Carpinteria, Calif.), which is a clinically validated and FDA approved test for evaluation of PDL1 expression in NSCLC. This test has been validated to sensitively, specifically, and reproducibly measure PD-L1 levels in the clinical samples. This is currently the only commercially available assay with a clinically relevant scoring system that has been associated with response to anti-PD-1therapy.

PDL1 IHC 22C3 pharmDx is a qualitative immunohistochemical assay using monoclonal mouse anti-PDL1 antibody, (clone 22C3), that can be used in the detection of PDL1 protein in formalin-fixed paraffin-embedded (FFPE) Non-Small Cell Lung Cancer (NSCLC) tissues. The assay can be performed on Autostainer Link 48 system and visualized using the EnVision FLEX system. PDL1 protein expression is qualified using Tumor Proportion Score (TPS), which is the percentage of viable tumor cells showing partial or complete membrane staining. In some embodiments, the specimen is considered PDL1 positive if TPS≥50% of the viable tumor cells exhibit membrane staining at any intensity. PDL1 IHC 22C3 pharmDx is indicated as an aid in identifying NSCLC patients for treatment with KEYTRUDA® (pembrolizumab). Additional details on the scoring system and response to Pembrolizumab are described in the article by Garon et al (N Engl J Med 2015; 372:2018-28). In some embodiments, NSCLC patient specimens can be considered positive for PDL1 expression if Tumor Proportion Score is ≥50% of the of viable tumor cells exhibit membrane staining (partial or complete) at any intensity (i.e. ≥1+). In some embodiments, this can be in specific regard to antibody clone 22C3. As noted above, in some embodiments, a sample is PDL1 positive if it stains at 5% for PDL1 including tumor or immune cells.

Antibodies and compositions comprising antibodies are provided for use in methods of treatment for humans or animals. Methods of treating disease comprising administering B7-H4 antibodies are also provided. Nonlimiting exemplary diseases that can be treated with B7-H4 antibodies include, but are not limited to various forms of cancer.

The B7-H4 antibody can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In some embodiments, an effective dose of a B7-H4 antibody is administered to a subject one or more times. In some embodiments, an effective dose of a B7-H4 antibody is administered to the subject once a month, more than once a month, such as, for example, every two months or every three months. In some embodiments, an effective dose of a B7-H4 antibody is administered less than once a month, such as, for example, every two weeks or every week. An effective dose of a B7-H4 antibody is administered to the subject at least once. In some embodiments, the effective dose of a B7-H4 antibody may be administered multiple times, including for periods of at least a month, at least six months, or at least a year.

In some embodiments, pharmaceutical compositions are administered in an amount effective for treatment of (including prophylaxis of) cancer. The therapeutically effective amount is typically dependent on the weight of the subject being treated, his or her physical or health condition, the extensiveness of the condition to be treated, or the age of the subject being treated. In general, B7-H4 antibodies may be administered in an amount in the range of about 10 µg/kg body weight to about 100 mg/kg body weight per dose. In some embodiments, B7-H4 antibodies may be administered in an amount in the range of about 50 µg/kg body weight to about 5 mg/kg body weight per dose. In some embodiments, B7-H4 antibodies may be administered in an amount in the range of about 100 µg/kg body weight to about 10 mg/kg body weight per dose. In some embodiments, B7-H4 antibodies may be administered in an amount in the range of about 100 µg/kg body weight to about 20 mg/kg body weight per dose. In some embodiments, B7-H4 antibodies may be administered in an amount in the range of about 0.5 mg/kg body weight to about 20 mg/kg body weight per dose. In some embodiments, B7-H4 antibodies may be administered in an amount in the range of about 0.5 mg/kg body weight to about 10 mg/kg body weight per dose. In some embodiments, B7-H4 antibodies may be administered in an amount in the range of about 5 mg/kg body weight or lower, for example less than 4, less than 3, less than 2, or less than 1 mg/kg of the B7-H4 antibody.

In some embodiments, pharmaceutical compositions are administered in an amount effective for treatment of cancer. The therapeutically effective amount is typically dependent on the weight of the subject being treated, his or her physical or health condition, the extensiveness of the condition to be treated, or the age of the subject being treated. In general, B7-H4 antibodies may be administered in an amount in the range of about 10 µg/kg body weight to about 100 mg/kg body weight per dose. In some embodiments, B7-H4 antibodies may be administered in an amount in the range of about 50 µg/kg body weight to about 5 mg/kg body weight per dose. In some embodiments, B7-H4 antibodies may be administered in an amount in the range of about 100 µg/kg body weight to about 10 mg/kg body weight per dose. In some embodiments, B7-H4 antibodies may be administered in an amount in the range of about 100 µg/kg body weight to about 20 mg/kg body weight per dose. In some embodiments, B7-H4 antibodies may be administered in an amount in the range of about 0.5 mg/kg body weight to about 20 mg/kg body weight per dose. In some embodiments, B7-H4 antibodies may be administered in an amount in the range of about 0.5 mg/kg body weight to about 10 mg/kg body weight per dose. In some embodiments, B7-H4 antibodies may be administered in an amount in the range of about 0.5 mg/kg body weight to about 5 mg/kg body weight per dose.

Below is an outline of further embodiments and particulars for performing the above noted methods, as well as further methods. The placement of the embodiments below is to clarify that it is contemplated that any of the embodiments provided herein can be combined with any of the other aspects listed herein.

In some embodiments, the cancer that is treated by the administration of B7-H4 is any cancer. In some embodiments, the cancer is one that expresses B7-H4 at a high level. In some embodiments, this is any amount greater than a negative amount in a staining assay. In some embodiments, this is any amount above a level present in surrounding healthy tissue or corresponding tissue from a healthy subject. In some embodiments, high levels of expression of B7-H4 is defined in comparison to an expression level of B7-H4 in a non-cancer sample. In some embodiments, the cancers to be treated by any of the methods provided herein can be any of those listed in FIG. 1. In some embodiments, the cancers to be treated are those above kidney renal clear cell carcinoma in the list in FIG. 1. In some embodiments, the cancers to be treated are those above kidney chromophobe in the list in FIG. 1. In some embodiments, the cancers to be treated are those in the upper third of the list in FIG. 1. In some embodiments, the cancers to be treated are those in the upper half of the list in FIG. 1. In some embodiments, the higher the cancer is listed in FIG. 1, the greater benefit a B7-H4 antibody can have on the cancer. As noted elsewhere, the cancer can also be one that expresses a low level of PD-L1, does not respond to PD-1 therapy, stops responding to PD-1 therapy. In some embodiments, the cancer can be one that does respond to PD-1 therapy, but receive further benefit from the presence of a B7-H4 antibody.

In some embodiments, the cancer is at least one of a lung cancer, a breast cancer, a head and neck cancer, an ovarian cancer, or an endometrial cancer. In some embodiments, the cancer consists of a lung cancer, a breast cancer, a head and neck cancer, an ovarian cancer, and an endometrial cancer. In some embodiments, the breast cancer is a triple negative cancer, an ER+ cancer or a HER2+ cancer. In some embodiments, the breast cancer is a triple negative cancer. In some embodiments, any of the types of cancers provided herein can be treated with a B7-H4 antibody.

In some embodiments, a "low level" of PDL1 is low relative to a PDL1 level that would indicate that the subject is eligible to receive a PD-1 therapy as a treatment of the cancer. In some embodiments, the "low level" of PDL1 is no expression of PDL1. In some embodiments, the low level of PDL1 is an expression level of a reference sample. In some embodiments, the reference sample is a sample from a normal tissue. In some embodiments, the normal tissue is a tissue that is an adjacent tissue to the cancer in the subject. In some embodiments, the cancer expresses both B7-H4 and PDL1. For example, when assaying for expression via staining, the levels of the protein are above those understood to be "negative" to one of skill in the art for the particular assay. While exemplary assays are provided herein, such as RNA based assays, FACS, and IHC, additional assays, can also be employed, with their appropriate levels of positive and negative results. Any method of detecting the level of a protein in a sample is contemplated. One skilled in the art can select a suitable method depending on the type of sample being analyzed and the identity and number of proteins being detected. Nonlimiting exemplary such methods include immunohistochemistry, ELISA, Western blotting, multiplex analyte detection (using, for example, Luminex technology), mass spectrometry, etc. Similarly, any method of detecting the level of an mRNA in a sample is contemplated. One skilled in the art can select a suitable method depending on the type of sample being analyzed and the identity and number of mRNAs being detected. Nonlimiting exemplary such methods include RT-PCR, quantitative RT-PCR and microarray-based methods, etc.

Figure 8A:
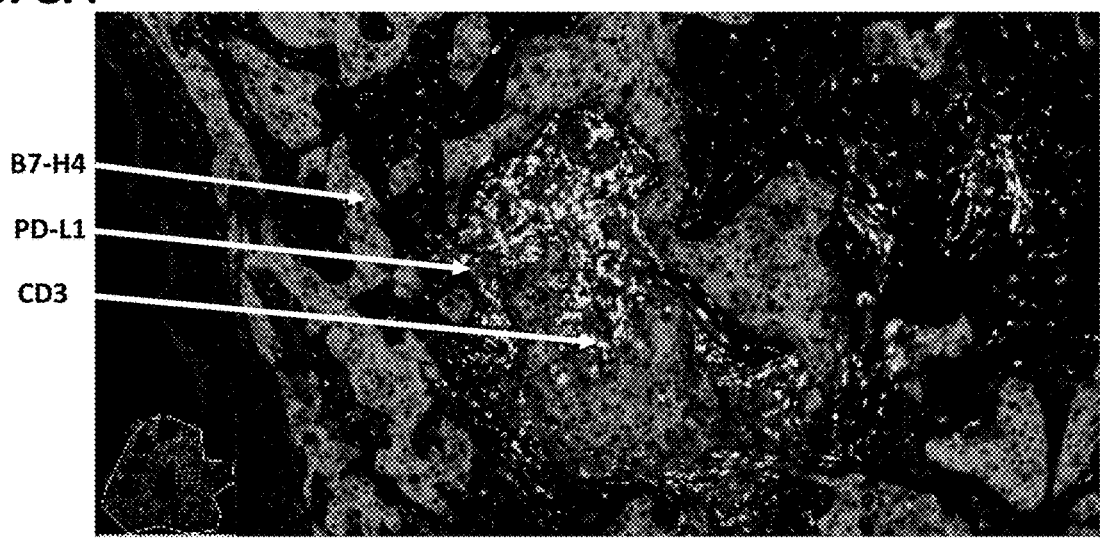
FIGS. 8A and 8B depict a series of images showing the spatial expression of PD-L1, T-cell marker (CD3) and B7-H4 in ovarian cancer.
Figure 8B:
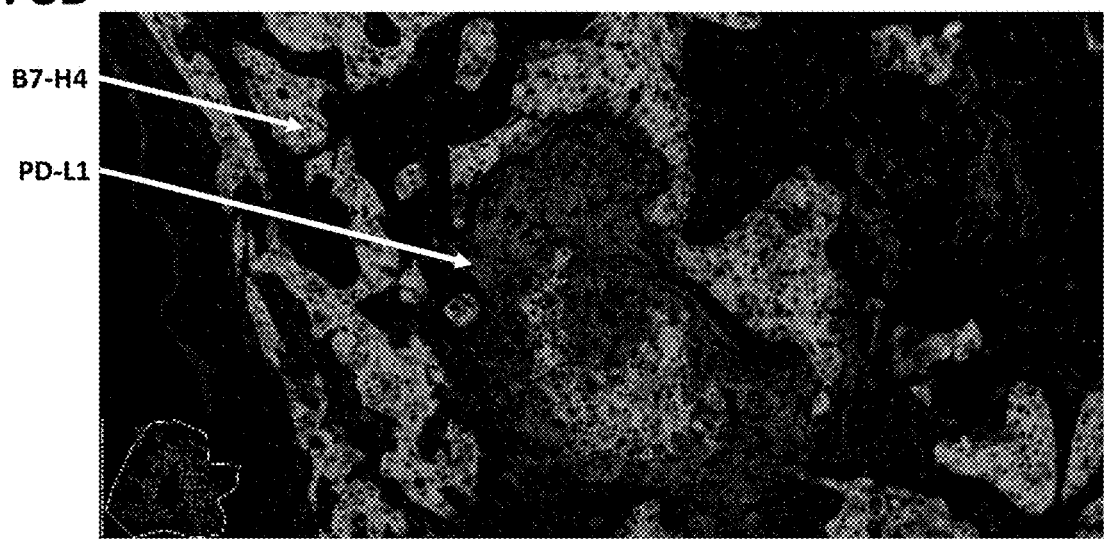

In some embodiments, rather than assaying an entire cancerous area as a whole, one can examine expression levels of B7-H4 and PDL1 on a cell by cell level, for example, as shown in FIGS. 8A and 8B. In some embodiments, B7-H4 is expressed in a different cell from PDL1 expression, and such situations can result in a benefit from the use of a B7-H4 antibody in the treatment of cancer. Thus, in some embodiments, a therapy is provided for cancer in subjects where B7-H4 expression exists (for example, positive staining) in locations where PD-1 expression is low (for example, negative staining).

In some embodiments, B7-H4 is expressed in endothelial cells, wherein the endothelial cells are adjacent to a cell expressing PDL1.

In some embodiments, the subject becomes non-responsive to PD-1 therapy. In some embodiments, both therapeutic approaches can be used on a single patient, but the therapies are administered at different times. In some embodiments, both therapies (a PD-1 therapy and a B7-H4 antibody) are coadministered. In some embodiments, a PD-1 antibody is administered after the B7-H4 antibody is administered. In some embodiments, the two therapies are administered within a single composition.

In some embodiments, inhibition of growth of the cancer is achieved by antibody-dependent cell-mediated cytotoxicity (ADCC). In some embodiments, any of the methods provided herein can further comprise assaying an amount of B7-H4 present in a cancer in the subject. In some embodiments, the subject can be identified as one that has previously received no significant improvement from a PD-1 therapy. In some embodiments, the subject is one that received a detectable level of improvement from the PD-1 therapy, but an additional amount of improvement is beneficial or desired for the subject. Any method of detecting the level of a protein in a sample is contemplated. One skilled in the art can select a suitable method depending on the type of sample being analyzed and the identity and number of proteins being detected. Nonlimiting examples of such methods include immunohistochemistry, ELISA, Western blotting, multiplex analyte detection (using, for example, Luminex technology), mass spectrometry, etc. Similarly, any method of detecting the level of an mRNA in a sample is contemplated. One skilled in the art can select a suitable method depending on the type of sample being analyzed and the identity and number of mRNAs being detected. Nonlimiting exemplary such methods include RT-PCR, quantitative RT-PCR and microarray-based methods, etc.

In some embodiments, the method of treatment described herein can further include administering: radiation therapy, chemotherapy, vaccination, targeted tumor therapy, cancer immunotherapy, cytokine therapy, surgical resection, chromatin modification, ablation, cryotherapy, an antisense agent against a tumor target, a siRNA agent against a tumor target, a microRNA agent against a tumor target or an anti-cancer/tumor agent.

As will be appreciated by one of skill in the art, in some embodiments, any of the herein disclosed methods can be used separately or in combination for treatment of cancer.

In some embodiments, any of the methods provided herein can be performed by an antagonist B7-H4 antibody.

Antibodies to B7-H4

B7-H4 antibodies include, but are not limited to, humanized antibodies, chimeric antibodies, mouse antibodies, human antibodies, and antibodies comprising the heavy chain and/or light chain CDRs discussed herein. In some embodiments, an isolated antibody that binds to B7-H4 is provided. In some embodiments, a B7-H4 antibody modulates B7-H4 activity. In some embodiments, the antibody is one that induces an ADCC response in a subject to receive the antibody. In some embodiments, the antibody is an IgG1 antibody.

In some embodiments, a B7-H4 antibody comprises a heavy chain variable region and a light chain variable region. In some embodiments, a B7-H4 antibody comprises at least one heavy chain comprising a heavy chain variable region and at least a portion of a heavy chain constant region, and at least one light chain comprising a light chain variable region and at least a portion of a light chain constant region. In some embodiments, a B7-H4 antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some embodiments, the heavy chain is the region of the B7-H4 antibody that comprises the three heavy chain CDRs. In some embodiments, the light chain is the region of the B7-H4 antibody that comprises the three light chain CDRs.

In some embodiments, an antibody is a chimeric antibody. Certain chimeric antibodies are described, for example, in U.S. Pat. No. 4,816,567; and Morrison et al., (1984) *Proc. Natl. Acad. Sci. USA,* 81:6851-6855 (1984)). In one example, a chimeric antibody comprises a non-human variable region (for example, a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some embodiments, a chimeric antibody described herein comprises a human IgG4 constant region and a human κ light chain.

As noted above, whether or not effector function is desirable may depend on the particular method of treatment intended for an antibody. Thus, in some embodiments, when effector function is desirable, a chimeric B7-H4 antibody comprising a human IgG1 heavy chain constant region or a human IgG3 heavy chain constant region is selected. In some embodiments, when effector function is not desirable, a chimeric B7-H4 antibody comprising a human IgG4 or IgG2 heavy chain constant region is selected.

In some embodiments, humanized antibodies that bind B7-H4 are provided. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) *Front. Biosci.* 13: 1619-1633, and are further described, for example, in Riechmann et al., (1988) *Nature* 332:323-329; Queen et al., (1989) *Proc. Natl Acad. Sci. USA* 86: 10029-10033; U.S. Pat. Nos. 5,821,337, 7,527,791, 6,982,321, and 7,087,409; Kashmiri et al., (2005) *Methods* 36:25-34; Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260 (describing the "guided selection" approach to FR shuffling).

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of light or heavy chain variable regions (see, for example, Carter et al. (1992) *Proc. Natl. Acad. Sci. USA,* 89:4285; and Presta et al. (1993) *J. Immunol,* 151:2623); human mature (somatically mutated) framework regions or human germline framework regions (see, for example, Almagro and Fransson, (2008) *Front. Biosci.* 13:1619-1633); and framework regions derived from screening FR libraries (see, for example, Baca et al., (1997) *J. Biol. Chem.* 272: 10678-10684 and Rosok et al., (1996) *J. Biol. Chem.* 271:22611-22618).

In some embodiments, a B7-H4 antibody is a human antibody. Human antibodies can be produced using various techniques known in the art. Human antibodies are described generally in van Dijk and van de Winkel, (2001) *Curr. Opin. Pharmacol.* 5:368-374 and Lonberg, (2008) *Curr. Opin. Immunol.* 20:450-459. In some embodiments, the human antibody is not a naturally occurring antibody. In some embodiments, the human antibody is a monoclonal antibody; thus, in some embodiments, each of the human antibodies in a set can bind to the same epitope on the antigen.

Human antibodies can be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, (2005) *Nat. Biotech.* 23: 1117-1125. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, for example, by combining with a different human constant region.

Human antibodies can also be made by hybridoma-based methods. Human myeloma and mouse-human heteromyeloma cell lines for the production of human monoclonal antibodies have been described. (See, for example, Kozbor (1984) *J. Immunol,* 133: 3001; Brodeur et al., *Monoclonal Antibody Production Techniques and Applications,* pp. 51-63 (Marcel Dekker, Inc., New York, 1987); and Boerner et al, (1991) *J. Immunol.,* 147:86). Human antibodies generated via human B-cell hybridoma technology are also described in Li et al., (2006) *Proc. Natl. Acad. Sci. USA,* 103:3557-3562. Additional methods include those described, for example, in U.S. Pat. No. 7,189,826 (describing production of monoclonal human IgM antibodies from hybridoma cell lines) and Ni, (2006) *Xiandai Mianyixue*, 26(4):265-268 (describing human-human hybridomas). Human hybridoma technology (Trioma technology) is also described in Vollmers and Brandlein, (2005) *Histology and Histopathology*, 20(3):927-937 (2005) and Vollmers and Brandlein, (2005) *Methods and Findings in Experimental and Clinical Pharmacology*, 27(3): 185-191.

Human antibodies can also be generated by isolating Fv clone variable domain sequences selected from human-derived phage display libraries. Such variable domain sequences may then be combined with a desired human constant domain. Techniques for selecting human antibodies from antibody libraries are described below.

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, for example, in Hoogenboom et al. in Methods in Molecular Biology 178: 1-37 (O'Brien et al., ed., Human Press, Totowa, N.J., 2001) and further described, for example, in the McCafferty et al, (1990) *Nature* 348:552-554; Clackson et al, (1991) *Nature* 352: 624-628; Marks et al, (1992) *J. Mol. Biol* 222: 581-597; Marks and Bradbury, in *Methods in Molecular Biology* 248: 161-175 (Lo, ed., Human Press, Totowa, N.J., 2003); Sidhu et al, (2004) *J. Mol. Biol.* 338(2): 299-310; Lee et al., (2004) *J. Mol. Biol.* 340(5): 1073-1093; Fellouse, (2004) *Proc. Natl. Acad. Sci. USA* 101(34): 12467-12472; and Lee et al, (2004) *J. Immunol. Methods* 284(1-2): 119-132 and PCT publication WO 99/10494.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., (1994) *Ann. Rev. Immunol.*, 12:433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (for example, from human) to provide a single source of antibodies to a wide range of non-self and also self-antigens without any immunization as described by Griffiths et al., (1993) *EMBO J* 12:725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter (1992), *J. Mol. Biol*, 227:381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

In some embodiments, a human B7-H4 antibody comprises one or more human constant regions. In some embodiments, the human heavy chain constant region is of an isotype selected from IgA, IgG, and IgD. In some embodiments, the human light chain constant region is of an isotype selected from κ and λ. In some embodiments, a human antibody described herein comprises a human IgG constant region. In some embodiments, a human antibody described herein comprises a human IgG4 heavy chain constant region. In some embodiments, a human antibody described herein comprises a human IgG4 constant region and a human κ light chain.

In some embodiments, when effector function is desirable, a human B7-H4 antibody comprising a human IgG1 heavy chain constant region or a human IgG3 heavy chain constant region is selected. In some embodiments, when effector function is not desirable, a human B7-H4 antibody comprising a human IgG4 or IgG2 heavy chain constant region is selected.

As noted herein, the term "human antibody" denotes the genus of possible sequences for the antibody construct, rather than a source of the antibody.

In some embodiments, the antibody can include one or more of the CDRs in at least one of FIGS. 11C-11F. In some embodiments, the antibody can include two or more of the CDRs in at least one of FIGS. 11C-11F. In some embodiments, the antibody can include three or more of the CDRs in at least one of FIGS. 11C-11F. In some embodiments, the antibody can include four or more of the CDRs in at least one of FIGS. 11C-11F. In some embodiments, the antibody can include five or more of the CDRs in at least one of FIGS. 11C-11F. In some embodiments, the antibody can include six of the CDRs in at least one of FIGS. 11C-11F. In some embodiments, the antibody includes the 6 CDRs in FIG. 11C. In some embodiments, the antibody includes the 6 CDRs in FIG. 11D. In some embodiments, the antibody includes the 6 CDRs in FIG. 11E. In some embodiments, the antibody includes the 6 CDRs in FIG. 11F. In some embodiments, the antibody includes at least one of the heavy and/or light chain variable regions in FIGS. 11C-11F. In some embodiments, the antibody includes the heavy and the light chain variable regions in FIG. 11C. In some embodiments, the antibody includes the heavy and the light chain variable regions in FIG. 11D. In some embodiments, the antibody includes the heavy and the light chain variable regions in FIG. 11E. In some embodiments, the antibody includes the heavy and the light chain variable regions in FIG. 11F.

In some embodiments, the antibodies inhibit and/or reduce a tumor intrinsic signal. In some embodiments, the tumor intrinsic signal is one or more signals selected from: a pro-survival signal; an autocrine or paracrine growth signal; a differentiation signal; a STAT-, JAK-, AKT- or PI3K-mediated signal; an anti-apoptotic signal; and a signal promoting and/or necessary for one or more of: tumor invasiveness, metastasis, epithelial-mesenchymal transition, and/or spreading from one tissue or organ to another non-adjacent tissue or organ.

Exemplary Antibody Constant Regions

In some embodiments, an antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, an antibody described herein comprises a human IgG constant region.

Throughout the present specification and claims unless explicitly stated or known to one skilled in the art, the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991). The "EU index as in Kabat" refers to the residue numbering of the human IgG1 EU antibody.

As noted above, whether or not effector function is desirable may depend on the particular method of treatment intended for an antibody. Thus, in some embodiments, when effector function is desirable, a B7-H4 antibody comprising a human IgG1 heavy chain constant region or a human IgG3 heavy chain constant region is selected. In some embodiments, when effector function is not desirable, a B7-H4 antibody comprising a human IgG4 or IgG2 heavy chain constant region is selected.

In some embodiments, an antibody comprises a variant Fc region has at least one amino acid substitution compared to the Fc region of a wild-type IgG or a wild-type antibody. In some embodiments, the variant Fc region has two or more amino acid substitutions in the Fc region of the wild-type antibody. In some embodiments, the variant Fc region has three or more amino acid substitutions in the Fc region of the wild-type antibody. In some embodiments, the variant Fc region has at least one, two or three or more Fc region amino acid substitutions described herein. In some embodiments, the variant Fc region herein will possess at least about 80% homology with a native sequence Fc region and/or with an Fc region of a parent polypeptide. In some embodiments, the variant Fc region herein will possess at least about 90% homology with a native sequence Fc region and/or with an Fc region of a parent polypeptide. In some embodiments, the variant Fc region herein will possess at least about 95% homology with a native sequence Fc region and/or with an Fc region of a parent polypeptide.

In some embodiments, an antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, for example, Wright et al. *TIBTECH* 15:26-32 (1997). The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (for example, complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, that is, between positions 294 and 300, due to minor sequence variations in antibodies. Such fucosylation variants may have improved ADCC function. See, for example, US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, for example, Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, for example, in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, for example, in WO 1997/30087 (Patel et al.); WO 1998/58964 (Raju, S.); and WO 1999/22764 (Raju, S.).

Antibody variants are also provided with amino-terminal leader extensions. For example, one or more amino acid residues of the amino-terminal leader sequence are present at the amino-terminus of any one or more heavy or light chains of an antibody. An exemplary amino-terminal leader extension comprises or consists of three amino acid residues, VHS, present on one or both light chains of an antibody variant.

The in vivo or serum half-life of human FcRn high affinity binding polypeptides can be assayed, for example, in transgenic mice, in humans, or in non-human primates to which the polypeptides with a variant Fc region are administered. See also, for example, Petkova et al. *International Immunology* 18(12):1759-1769 (2006).

In some embodiments, the antibody variant mediates ADCC in the presence of human effector cells more effectively than a parent antibody. In some embodiments, the antibody variant is substantially more effective at mediating ADCC in vitro, when the amounts of polypeptide variant and parent antibody used in the assay are essentially the same. In some embodiments, the antibody variant is substantially more effective at mediating ADCC in vivo, when the amounts of polypeptide variant and parent antibody used in the assay are essentially the same. Generally, such variants will be identified using the in vitro ADCC assay as herein disclosed, but other assays or methods for determining ADCC activity, for example in an animal model etc., are contemplated.

B7-H4 Antibody Expression and Production

Nucleic acid molecules comprising polynucleotides can encode one or more chains of B7-H4 antibodies. In some embodiments, a nucleic acid molecule comprises a polynucleotide that encodes a heavy chain or a light chain of a B7-H4 antibody. In some embodiments, a nucleic acid molecule comprises both a polynucleotide that encodes a heavy chain and a polynucleotide that encodes a light chain, of a B7-H4 antibody. In some embodiments, a first nucleic acid molecule comprises a first polynucleotide that encodes a heavy chain and a second nucleic acid molecule comprises a second polynucleotide that encodes a light chain.

In some embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of a B7-H4 antibody comprises a nucleotide sequence that encodes at least one CDR. In some embodiments, a polynucleotide encoding a heavy chain or light chain of a B7-H4 antibody comprises a nucleotide sequence that encodes at least 3 CDRs. In some embodiments, a polynucleotide encoding a heavy chain or light chain of a B7-H4 antibody comprises a nucleotide sequence that encodes at least 6 CDRs. In some embodiments, a polynucleotide encoding a heavy chain or light chain of a B7-H4 antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

Nucleic acid molecules can be constructed using recombinant DNA techniques conventional in the art. In some embodiments, a nucleic acid molecule is an expression vector that is suitable for expression in a selected host cell.

Vectors

Vectors comprising polynucleotides that encode B7-H4 heavy chains and/or B7-H4 light chains are provided. Vectors comprising polynucleotides that encode B7-H4 heavy chains and/or B7-H4 light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NS0 cells. Exemplary such vectors are described, for example, in Running Deer et al., *Biotechnol. Prog.* 20:880-889 (2004).

Antibodies can be screened to determine, for example, their affinity and specificity of binding to B7-H4, B7-H4 isoforms, tumor-specific B7-H4 polypeptides, post-translationally modified B7-H4 polypeptides, and/or differentially expressed, glycosylated, post-translationally modified and/or spliced B7-H4 polypeptides by using assays known in the art. For example, the assays may include competitive and noncompetitive assays. Assays of interest include enzyme-linked immunosorbent assay (ELISA), radioimmunoassay (RIA), flow cytometry, etc. Binding assays including Biacore or Octet may also be used. For example, binding assays may use purified or semi-purified B7-H4, or alternatively may use cells that express B7-H4, e.g., cells transfected with an expression construct for B7-H4; T-cells that have been stimulated through cross-linking of CD3 and CD28; the addition of irradiated allogeneic cells, etc. As an example of a binding assay, purified B7-H4 may be bound to an insoluble support, e.g., a microtiter plate, magnetic beads, etc. A candidate agent and soluble, labeled B7-H4 ligand are added to the cells, and the unbound components are then washed off. The ability of the candidate agent to compete with the natural ligand for B7-H4 binding may be determined by quantification of bound, labeled ligand.

In some embodiments, the assay of interest is directed to antibodies that block the binding of B7-H4 to its receptor. The antibody will be substantially unreactive with related molecules to B7-H4, such as CD28, other B7 superfamily members, and/or other members of the immunoglobulin superfamily. Further, the antibody does not activate B7-H4 signaling. In another embodiment, the antibody does not activate B7-H4 signaling but, in some embodiments, may also bind to one or more other members of the B7 superfamily, including B7.1, B7.2, ICOS Ligand, PD-L1, PD-L2, B7-H3, B7-H5, B7-H6 and/or B7-H7. In an exemplary embodiment, a functional assay detects that an agent blocks the binding of B7-H4 to its receptor, for example, by measuring cell cycle progression, release of IL-2, IL-4, IFN-gamma, TNF-alpha, or other cytokines, expression of CD25 and CD69, or the production/emission of a reporter expressed in a cell line engineered to change the production/emission of the reporter when B7-H4 does not bind its receptor, etc.

One skilled in the art may measure changes in cell surface marker expression of B7-H4 or cellular changes following B7-H4 activation/inhibition (including, for example, cell cycle progression, and/or cytokine release) using assays that are well known in the art. These assays include, but are not limited to, flow cytometry (including, for example, fluorescent activating cell sorting (FACS)), indirect immune-fluorescence, solid phase enzyme-linked immunosorbent assay (ELISA), ELISpot assays, western blotting (including in cell western), immunofluorescent staining, microengraving (see Han Q et al. Lab Chip. 2010; 10(11):1391-1400), Quant-iT and Qubit protein assay kits, NanoOrange protein quantitation kit, CBQCA protein quantitation kits, EZQ protein quantitation kit, Click-iT reagents, Pro-Q Diamond phosphoprotein stain, Pro-Q glycoprotein stain kits, peptide and protein sequencing, N-terminal amino acid analysis (Life-Science Technologies, Grand Island, N.Y.), chemiluminescence or colorimetric based ELISA cytokine Arrays (Signosis) Intracellular Cytokine Staining (ICS), BD Phosflow™ and BD™ Cytometric Bead Arrays (BD Sciences, San Jose, Calif.); RT-PCR (RT2 Profiler™ Human Common Cytokine PCR Arrays (Cat # PAHS-021) ((SABiosciences/QIAGEN)); CyTOF Mass Cytometer (DVS Sciences, Sunnyvale Calif.); Mass Spectrometry, Microplate capture and detection assay (Thermo Scientific, Rockland, Ill.), Multiplex Technologies (for example Luminex, Austin, Tex.); Flow-Cellect™ T-cell Activation Kit (EMD Millipore); Surface Plasmon Resonance (SPR)-based technologies (for example Biacore, GE Healthcare Life Sciences, Uppsala, Sweden); CD4$^+$ Effector Memory T-cell Isolation Kit and CD8$^+$ CD45RA$^+$ Effector T-cell Isolation Kit (Miltenyi Biotec Inc., CA); The EasySep™ Human T-cell Enrichment Kit (StemCells, Inc., Vancouver, Canada); HumanTh1/Th2/Th17 Phenotyping Kit (BD Biosciences, CA); immunofluorescent staining of incorporated bromodeoxyuridine (BrdU) or 7-aminoactinomycin D. See also, Current Protocols in Immunology (2004) sections 3.12.1-3.12.20 by John Wiley & Sons, Inc., or Current Protocols in Immunology (2013) or by John Wiley & Sons, Inc., the contents of which are herein incorporated by reference in their entirety.

Host Cells

In some embodiments, B7-H4 heavy chains and/or B7-H4 light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO—S, DG44. Lec13 CHO cells, and FUT8 CHO cells; PER.C6® cells (Crucell); and NSO cells. In some embodiments, B7-H4 heavy chains and/or B7-H4 light chains may be expressed in yeast. See, for example, U.S. Publication No. US 2006/0270045 A1. In some embodiments, a particular eukaryotic host cell is selected based on its ability to make desired post-translational modifications to the B7-H4 heavy chains and/or B7-H4 light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

Host cells comprising any of the polynucleotides or vectors described herein are also provided. In some embodiments, a host cell comprising a B7-H4 antibody is provided. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

B7-H4 antibodies can be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A, Protein G, Protein A/G, or an antibody affinity column may be used to bind the constant region and to purify a B7-H4 antibody. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

In some embodiments, a B7-H4 antibody is produced in a cell-free system. Nonlimiting exemplary cell-free systems are described, for example, in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

In some embodiments, antibodies prepared by the methods described above are provided. In some embodiments, the antibody is prepared in a host cell. In some embodiments, the antibody is prepared in a cell-free system. In some embodiments, the antibody is purified. In some embodiments, the antibody prepared in a host cell or a cell-free system is a chimeric antibody. In some embodiments, the antibody prepared in a host cell or a cell-free system is a humanized antibody. In some embodiments, the antibody prepared in a host cell or a cell-free system is a human antibody. In some embodiments, a cell culture media comprising a B7-H4 antibody is provided. In some embodiments, a host cell culture fluid comprising a B7-H4 antibody is provided.

In some embodiments, compositions comprising antibodies prepared by the methods described above are provided. In some embodiments, the composition comprises an antibody prepared in a host cell. In some embodiments, the composition comprises an antibody prepared in a cell-free system. In some embodiments, the composition comprises a purified antibody. In some embodiments, the composition comprises a chimeric antibody prepared in a host cell or a cell-free system. In some embodiments, the composition comprises a humanized antibody prepared in a host cell or a cell-free system. In some embodiments, the composition comprises a human antibody prepared in a host cell or a cell-free system.

In some embodiments, a composition comprising a B7-H4 antibody at a concentration of more than about any one of 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 125 mg/mL, 150 mg/mL, 175 mg/mL, 200 mg/mL, 225 mg/mL, or 250 mg/mL is provided. In some embodiments, the composition comprises a chimeric antibody prepared in a host cell or a cell-free system. In some embodiments, the composition comprises a humanized antibody prepared in a host cell or a cell-free system. In some embodiments, the composition comprises a human antibody prepared in a host cell or a cell-free system.

In some embodiments, the B7-H4 antibody can be combined with a PD-1 therapy. In some embodiments, the antibody selectively binds to B7-H4. In some embodiments, the B7-H4 antibody is a monoclonal human antibody. In some embodiments, the B7-H4 monoclonal human antibody has a $K_d$ of no larger than $10^{-7}$ for B7-H4, for example, the numerical value is less than $10^{-8}$, $10^{-9}$, $10^{-11}$, $10^{-11}$, $10^{-12}$, or lower.

In some embodiments, B7-H4 activity in the subject is reduced to a level adequate for a therapeutic treatment of the cancer in the subject. In some embodiments, the B7-H4 antibody blocks B7-H4 activity by at least 10%, for example, 20, 30, 40, 50, 60, 70, 80, 90, 95, 99, or 100% blockade of B7-H4 activity.

Pharmaceutical Compositions

In some embodiments, compositions comprising B7-H4 antibodies are provided in formulations with a wide variety of pharmaceutically acceptable carriers (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, $7^{th}$ ed., Lippencott Williams and Wilkins (2004); Kibbe et al., Handbook of Pharmaceutical Excipients, $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In some embodiments, a pharmaceutical composition comprising B7-H4 antibody is provided. In some embodiments, the pharmaceutical composition comprises a chimeric B7-H4 antibody. In some embodiments, the pharmaceutical composition comprises a humanized B7-H4 antibody. In some embodiments, the pharmaceutical composition comprises a human B7-H4 antibody. In some embodiments, the pharmaceutical composition comprises a B7-H4 antibody prepared in a host cell or cell-free system as described herein. In some embodiments, the pharmaceutical composition comprises pharmaceutically acceptable carrier.

In some embodiments, B7-H4 antibodies can be present in an amount in the range of about 50 µg/kg body weight to about 5 mg/kg body weight per dose. For example, in some embodiments, a dose for a 20 kg person can be within a range of about 1 mg to about 100 mg. In some embodiments, the dose can be within a range of 2 mg to 200 mg of the B7-H4 antibody. In some embodiments, the dose can be within a range of 10 mg to 400 mg of the B7-H4 antibody.

A dose for a 50 kg person can be within a range of about 2.5 mg to about 250 mg of the B7-H4 antibody. In some embodiments, the dose can be within a range of 5 mg to 500 mg of the B7-H4 antibody. In some embodiments, the dose can be within a range of 25 mg to 1000 mg of the B7-H4 antibody.

A dose for a 80 kg person can be within a range of about 4 mg to about 400 mg B7-H4 antibody. In some embodiments, the dose can be within a range of 8 mg to 800 mg of the B7-H4 antibody. In some embodiments, the dose can be within a range of 40 mg to 1600 mg of the B7-H4 antibody.

A dose for a 100 kg person can be within a range of about 5 mg to about 500 mg B7-H4 antibody. In some embodiments, the dose can be within a range of 10 mg to 1000 mg of the B7-H4 antibody. In some embodiments, the dose can be within a range of 50 mg to 4000 mg of the B7-H4 antibody.

In some embodiments, B7-H4 antibodies can be administered in vivo by various routes, including, but not limited to, intravenous, intra-arterial, parenteral, intraperitoneal or subcutaneous. The appropriate formulation and route of administration may be selected according to the intended application.

Combination Therapy

B7-H4 antibodies can be administered alone or with other modes of treatment. They can be provided before, substantially contemporaneous with, or after other modes of treatment, for example, surgery, chemotherapy, radiation therapy, or the administration of a biologic, such as another therapeutic antibody. In some embodiments, a B7-H4 antibody is administered in conjunction with another anti-cancer agent.

In some embodiments, the B7-H4 antibody is given concurrently with a second therapeutic agent (for example, a PD-1 therapy, such as a therapeutic antibody that binds to PD-1). For example, the two or more therapeutic agents are administered with a time separation of no more than about 60 minutes, such as no more than about any of 30, 15, 10, 5, or 1 minutes. In some embodiments, the B7-H4 antibody is administered sequentially with a second therapeutic agent. For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month, or longer.

In some embodiments, the B7-H4 antibody is administered with a second therapeutic method for treatment. Thus, the administration of an antibody can be in combination with another system of treatment.

In some embodiments, histological samples of tumors are graded using the antibody described herein according to Elston & Ellis, Histopathology, 1991, 19:403-10, which is hereby incorporated by reference in its entirety. In some embodiments, the antibody described herein is useful in establishing a tumor grade for the purposes of diagnosis or prognosis of a particular cancer.

In some embodiments, the methods described herein are useful for evaluating a subject and/or a specimen from a subject (e.g. a cancer patient). In some embodiments, evaluation is one or more of diagnosis, prognosis, and/or response to treatment.

In some embodiments, the methods described herein comprise evaluating a presence, absence, or level of a protein. In some embodiments, the methods described herein comprise evaluating a presence, absence, or level of expression of a nucleic acid. The compositions described herein may be used for these measurements. For example, in some embodiments, the methods described herein comprise contacting a specimen of the tumor or cells cultured from the tumor with a therapeutic agent as described herein.

In some embodiments, the method can include the measurement of a tumor specimen, including biopsy or surgical specimen samples. In some embodiments, the biopsy is a human biopsy. In various embodiments, the biopsy is any one of a frozen tumor tissue specimen, cultured cells, circulating tumor cells, and a formalin-fixed paraffin-embedded tumor tissue specimen. In some embodiments, the tumor specimen may be a biopsy sample, such as a frozen tumor tissue (cryosection) specimen. As is known in the art, a cryosection may employ a cryostat, which comprises a microtome inside a freezer. The surgical specimen is placed on a metal tissue disc which is then secured in a chuck and frozen rapidly to about −20° C. to about −30° C. The specimen is embedded in a gel like medium consisting of, for example, poly ethylene glycol and polyvinyl alcohol.

The frozen tissue is cut frozen with the microtome portion of the cryostat, and the section is optionally picked up on a glass slide and stained. In some embodiments, the tumor specimen may be a biopsy sample, such as cultured cells. These cells may be processed using the usual cell culture techniques that are known in the art. These cells may be circulating tumor cells. In some embodiments, the tumor specimen may be a biopsy sample, such as a formalin-fixed paraffin-embedded (FFPE) tumor tissue specimen. As is known in the art, a biopsy specimen may be placed in a container with formalin (a mixture of water and formaldehyde) or some other fluid to preserve it. The tissue sample may be placed into a mold with hot paraffin wax. The wax cools to form a solid block that protects the tissue. This paraffin wax block with the embedded tissue is placed on a microtome, which cuts very thin slices of the tissue. In certain embodiments, the tumor specimen contains less than about 100 mg of tissue, or in certain embodiments, contains about 50 mg of tissue or less. The tumor specimen (or biopsy) may contain from about 20 mg to about 50 mgs of tissue, such as about 35 mg of tissue. The tissue may be obtained, for example, as one or more (e.g., 1, 2, 3, 4, or 5) needle biopsies (e.g., using a 14-gauge needle or other suitable size). In some embodiments, the biopsy is a fine-needle aspiration in which a long, thin needle is inserted into a suspicious area and a syringe is used to draw out fluid and cells for analysis. In some embodiments, the biopsy is a core needle biopsy in which a large needle with a cutting tip is used during core needle biopsy to draw a column of tissue out of a suspicious area. In some embodiments, the biopsy is a vacuum-assisted biopsy in which a suction device increases the amount of fluid and cells that is extracted through the needle. In some embodiments, the biopsy is an image-guided biopsy in which a needle biopsy is combined with an imaging procedure, such as, for example, X ray, computerized tomography (CT), magnetic resonance imaging (MRI) or ultrasound. In some embodiments, the sample may be obtained via a device such as the MAMMOTOME® biopsy system, which is a laser guided, vacuum-assisted biopsy system for breast biopsy.

In some embodiments, the evaluation may direct treatment (including treatment with the antibodies described herein). In some embodiments, the evaluation may direct the use or withholding of adjuvant therapy after resection. Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease. In some embodiments, the antibodies are used as an adjuvant therapy in the treatment of a cancer. In some embodiments, the antibodies are used as the sole adjuvant therapy in the treatment of a cancer. In some embodiments, the antibodies described herein are withheld as an adjuvant therapy in the treatment of a cancer. For example, if a patient is unlikely to respond to an antibody described herein or will have a minimal response, treatment may not be administered in the interest of quality of life and to avoid unnecessary toxicity from ineffective chemotherapies. In such cases, palliative care may be used.

In some embodiments the antibodies are administered as a neoadjuvant therapy prior to resection. In some embodiments, neoadjuvant therapy refers to therapy to shrink and/or downgrade the tumor prior to any surgery. In some embodiments, neoadjuvant therapy means chemotherapy administered to cancer patients prior to surgery. In some embodiments, neoadjuvant therapy means an antibody is administered to cancer patients prior to surgery. Types of cancers for which neoadjuvant chemotherapy is commonly considered include, for example, breast, colorectal, ovarian, cervical, bladder, and lung. In some embodiments, the antibodies are used as a neoadjuvant therapy in the treatment of a cancer. In some embodiments, the use is prior to resection.

In some embodiments, the tumor microenvironment contemplated in the methods described herein is one or more of: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells; macrophages; neutrophils; and other immune cells located proximal to a tumor.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Bioinformatics Analysis

RNA sequencing data from about 7500 individual tumors with detailed clinical annotation was compiled as part of the tumor genome atlas project (TCGA consortium). The sequence data was normalized and processed for expression and mutational analysis by using OmicSoft Corporation (Cary, N.C.). B7-H4 transcripts levels were compared across all of the available tumor samples using MatLabR2013b software (Mathworks Inc., Natick, Mass.). Tumor types were ranked based on the mean B7-H4 transcript levels (FIG. 1). In each indication the distribution of B7-H4 level is represented by the box and wicker plot. The scale on the X-axis indicates B7-H4 mRNA levels based on normalized number of sequencing reads. The Box represent the 75% range from the mean and the whisker represent the 95% range from the mean. The samples out-side of the 95% range is indicated by (+). The "+" symbol is only present outside of the whisker section, and thus, the presence of the plus indicates the end of the whisker section.

Analysis of the gene-expression data for B7-H4 expression demonstrated a clear bi-model pattern. Highest levels of B7-H4 mRNA is observed in a majority of triple-negative breast cancer as defined by the expression of hormone receptor status, ovarian cancer, endometrial cancer, Her2+ breast cancer and ER+ breast cancer. Among the ER+ breast cancer the tumors, high levels of B7-H4 was associated with tumor that have a "low proliferation" as measured by the Genomic Grade Index (GGI; Metzger-Filho et al., PloS ONE 2013). Proliferation index as measured by GGI is associated with prognosis in ER+ breast cancer for front lines of hormonal therapy (e.g., Tamoxifen, Letrozole, etc.).

Figure 2A:
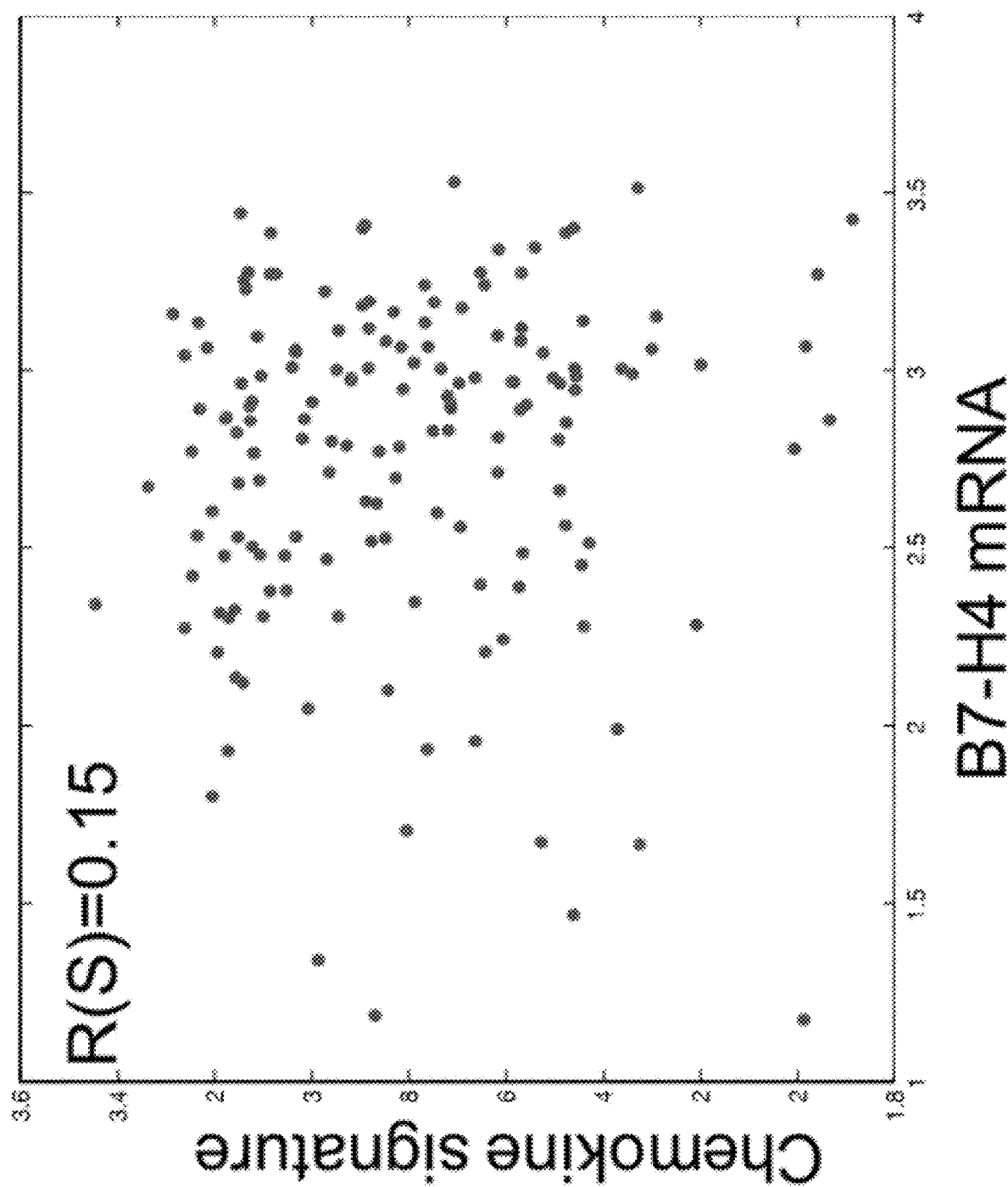
FIGS. 2A and 2B are graphs showing the levels of normalized chemokine signature for each tumor plotted on the Y-axis, mRNA levels of B7-H4 or PD-L1 are plotted on the X-axis. The Spearman correlation (R) of the association is show on the graph.
Figure 2B:
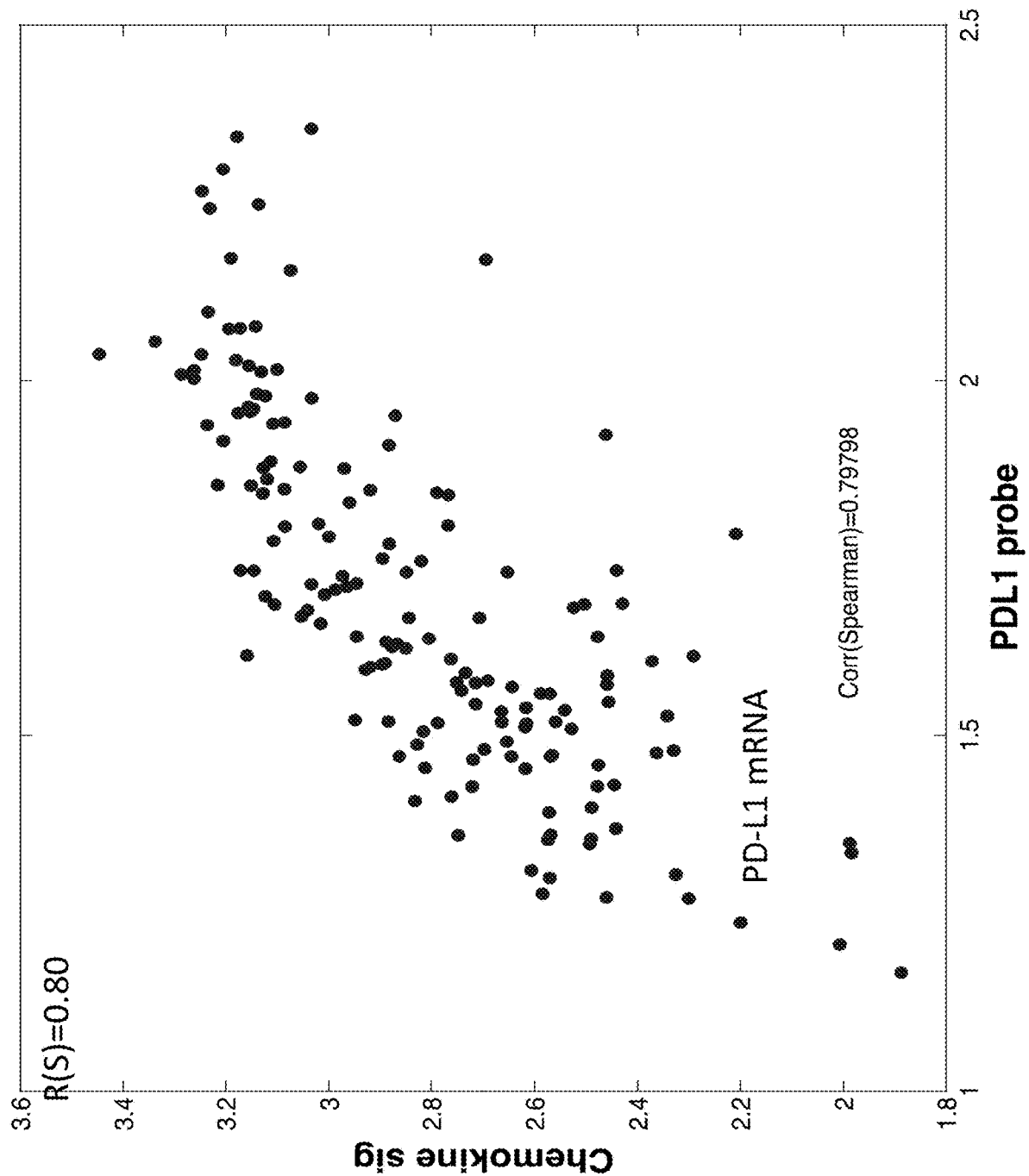

The association between T-cell infiltration and levels of B7-H4 expression were examined A set of 12 chemokine genes expression has been associated with high levels of T-cell infiltration and formation of lymphnode-like structures (Mule et al.). The chemokine signature score was computed for each sample based on the average expression of these 12 chemokine genes. This signature score was scored across all of the triple negative breast (TNBC) tumors. The levels of the chemokine signature score were correlated with PDL1 or B7-H4 levels in TNBC tumors (FIG. 2). There was a strong correlation (R=0.8; Spearman correlation) between chemokine signature score and PDL1 levels. These data demonstrate that PDL1 levels are regulated by T-cell infiltration. However, there is no correlation between B7-H4 levels and chemokine signature score in TNBC. Similar results were observed in other indications such as ovarian cancer and NSCLC (data not shown). These results show that unlike PD-L1, B7-H4 expression is independent of T-cell infiltration.

Example 2

Evaluation of B7-H4 Protein Expression in Human Tumors

To evaluate the prevalence of B7-H4 expression levels in breast cancer samples (n=148), tissue micro arrays were obtained from a commercial vendor (Pantomics Inc., Richmond Va.). The ER, PR and Her2 status of the breast cancer samples were provided by the vendor. Adjacent normal (n=7) samples and benign breast cancer samples (n=15) were analyzed.

B7-H4 expression was determined using an immune-histochemistry analysis with 8E7 antibody clone which recognizes the human B7-H4 (Cell Signaling Technology Inc., Danvers, Mass.). The specificity and sensitivity of the B7-H4 IHC assay was confirmed using breast tumor cell lines that are naturally expressing B7-H4 (breast cancer cell lines: SKBR3; ZR75-1; HCC-70) or cell lines (CHO) that over-express the extracellular domains of B7-H4 (data not shown). The staining intensity was scored by a trained pathologist using the following criteria. All positive staining was score based on membrane expression in at least two third of the cells.

0 (negative)=No or less than 5% of cells have membrane staining
1+ (mild)=5 to 10% of the cell are positive
2+ (moderate)=10 to 50% of the cells are positive
3+ (strong)=>50% of the cells are positive FIG. 3 shows representative images of the range of B7-H4 staining intensities observed in breast cancer. Prevalence of B7-H4 staining intensities in the ER+Her2−, Her2+ or TNBC are listed in Table 2. No detectable B7-H4 expression was observed in normal on cancer individuals or benign breast specimens. No detectable B7-H4 expression was observed in adjacent normal tissue from breast tumor patients (n=16). B7-H4 expression staining was observed to equal extent in all three sub-types of breast cancer. About 3-15% of the samples had strong B7-H4 staining and about 50 to 66% of the samples had detectable B7-H4 expression.

TABLE 2

Summary of the prevalence of B7-H4 staining in Breast cancer

| | Sub-type | N | Strong positive (3+) | Moderate positive (2+) | Weak (1+) | Negative (0) |
|---|---|---|---|---|---|---|
| Breast Ca | ER+ | 29 | 1 (3%) | 8 (28%) | 8 (28%) | 12 (41%) |
| | Her2+ | 35 | 5 (14%) | 10 (28%) | 8 (23%) | 12 (34%) |
| | TNBC | 84 | 8 (9%) | 10 (12%) | 24 (29%) | 42 (50%) |
| Benign | | 15 | 0 | 0 | 0 | 15 (100%) |
| Normal | | 7 | 0 | 0 | 0 | 7 (100%) |

Similarly the prevalence of B7-H4 expression in various subtypes of ovarian cancer was evaluated using 92 samples. The staining and scoring criteria used in these experiments were identical to that of the breast cancer study. The prevalence of B7-H4 expression in the major sub-types of ovarian cancer is presented in Table 3. B7-H4 expression was prevalent in all of ovarian tumor sub-types. Positive staining for B7-H4 was observed in a majority of tumors (69 to 75%) from serous ovarian or ovarian endometrioid adenocarcinoma subtype. Strong B7-H4 staining (3+) was observed in 36% of ovarian endometriod adenocarcinoma subtype and 25% of serous ovarian adenocarcinoma. Smaller subsets of tumors from mucinous or clear cell ovarian carcinoma were positive for B7-H4. No B7-H4 expression was observed in the adjacent normal ovarian tissue (N=16).

TABLE 3

Summary of the prevalence of B7-H4 staining in ovarian cancer

| Tumor sub-type | N | Strong (3+) | Moderate (2+) | Weak (1+) | Negative (0) |
|---|---|---|---|---|---|
| Clear cell carcinoma | 2 | 0 | 1 (50%) | 0 | 1 (50%) |
| Endometrioid adnocarcinoma | 28 | 10 (36%) | 3 (11%) | 8 (28%) | 7 (25%) |
| Mucinous cystadenocarcinoma | 12 | 1 (8%) | 0 | 2 (17%) | 9 (75%) |
| Serous cystadnocarcinoma | 48 | 12 (25%) | 12 (25%) | 9 (19%) | 15 (31%) |
| other | 2 | 0 | 0 | 0 | 2 (100%) |

Using the same IHC assay, the prevalence of B7-H4 expression in lung and HNSCC. B7-H4 expression was analyzed in 90 lung cancer samples representing various major clinical sub-types using the similar staining protocol and scoring strategy. Table 4 describes the summary of the IHC results from this study. Consistent with the mRNA analysis, a smaller sub-set of lung cancer samples (25%) were positive for B7-H4. A larger proportion of the squamous sub-type (40%) were positive for B7-H4 expression. Similar B7-H4 levels were observed in HNSCC cancer samples (Table 5). About 12 to 31% of the most common squamous subtype of HNSCC tumors were B7-H4 positive. The data suggest that tumors of the higher pathological stage (that is, patients with more aggressive tumors) may have a higher prevalence of B7-H4 expression.

TABLE 4

Summary of the prevalence of B7-H4 staining in lung cancer

| Tumor sub-type | Stage | N | Strong (3+) | Moderate (2+) | Weak (1+) | Negative (0) |
|---|---|---|---|---|---|---|
| SCLC | | 3 | 0 | 0 | 0 | 3 (100%) |
| Squainous | Stage I | 4 | 0 | 2 (50%) | 0 | 2 (50%) |
| | Stage II | 15 | 3 (20%) | 2 (13%) | 1 (7%) | 9 (67%) |
| | Stage III | 30 | 3 (10%) | 6 (20%) | 1 (3%) | 20 (60%) |
| Adenocarcinoma | | 16 | 0 | 1 (6%) | 0 | 15 (94%) |
| Adenosquamous | | 9 | 1 (11%) | 1 (11%) | 1 (11%) | 6 (67%) |
| Brochiolalveolar carcinoma | | 9 | 0 | 0 | 0 | 9 (100%) |
| Undifferntiated | | 4 | 0 | 0 | 0 | 4 (100%) |

TABLE 5

Summary of the prevalence of B7-H4 staining in HNSCC

| Tumor sub-type | Stage | N | Strongly positive | Moderate positive | Weak | Negative |
|---|---|---|---|---|---|---|
| Squamous | Stage I | 29 | 0 | 1 (4%) | 4 (14%) | 24 (82%) |
| | Stage II | 26 | 1 (4%) | 2 (8%) | 5 (19%) | 18 (69%) |
| | Stage III | 23 | 1 (5%) | 2 (9%) | 2 (9%) | 18 (77%) |
| Adenocarcinoma | | 3 | 1 (33%) | 0 | 1 (33%) | 1 (33%) |
| Adenoid cystic | | 6 | 0 | 0 | 4 (67%) | 2 (33%) |
| Mucoepidermoid | | 5 | 1 (20%) | 2 (40%) | 1 (20%) | 1 (20%) |

The specificity, sensitivity and surface expression of the B7-H4 was also measured using flow cytometry. Matched fresh tumor tissue and paraffin embedded tissue blocks from the same patient (n=6) were obtained. Surface expression of B7-H4 was evaluated using a flow cytometry where in B7-H4 was stained using MIH-43 antibody clone from (Biolegend, Inc.). Ovarian cancer samples that were scored positive by IHC by having IHC score of 1+ or higher also showed B7-H4 specific staining by flow cytometry. The sample that was negative for B7-H4 by IHC was also negative by flow cytometry. These results show that B7-H4 levels measured by IHC is concordant with the surface expression measured by flow cytometry. A representative image of flow cytometry analysis is presented in FIG. 4.

Figure 5:
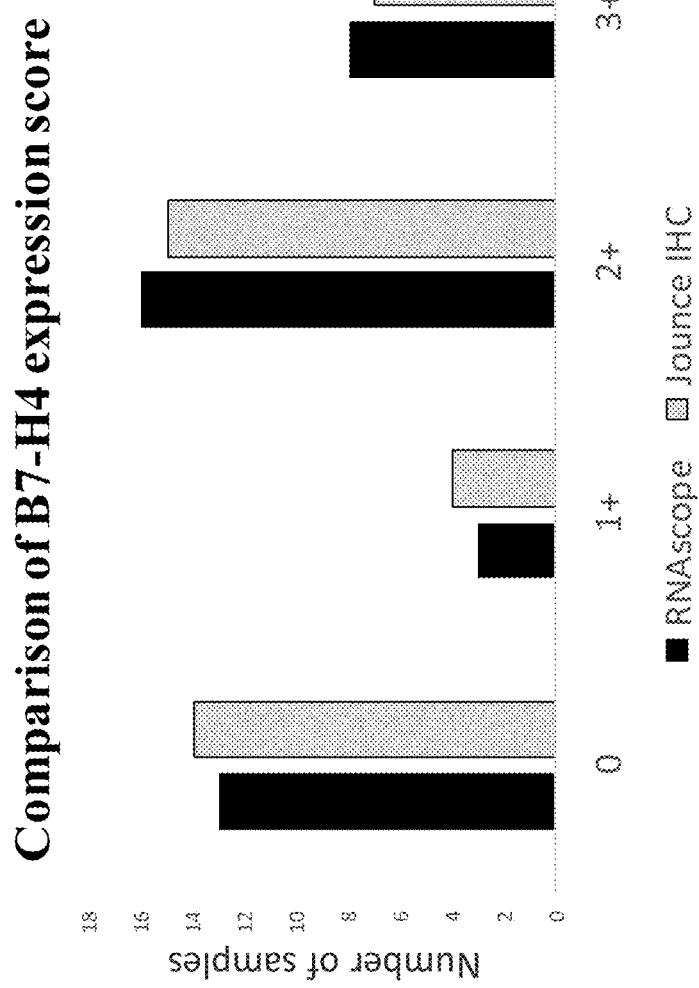
FIG. 5 is a graph showing a comparison of B7-H4 RNA detection by RNA scope and IHC in ovarian cancer. Comparison of the IHC score (0-3+) versus RNA scope score using similar criteria are shown.

The specificity B7-H4 positivity was also evaluated using an in-situ hybridization approach, herein referred as RNA scope (Wang et al., Journal of Medical Diagnostics, January 2012). Short oligo-nucleotide probes (18-25 nt) were synthesized and labelled by Advanced Cell Diagnostics Inc. (ACD, Hayward, Calif.). B7-H4 staining was compared by RNA scope and by IHC in ovarian cancer (n=50) and breast cancer specimens (n=72). A summary of the analysis is presented in FIG. 5. A subset of the samples from ovarian cancer did not have sufficient RNA for analysis (marked by x). Samples with high levels of IHC score had a similarly high levels of RNA. At the cellular levels the cells that were positive for B7-H4 mRNA also were positive for B7-H4 protein as detected by IHC.

Example 3

Comparison of B7-H4 and PD-L1 Expression

PDL1 expression in human tumors has been associated with better response to anti-PD-1 or anti-PDL1 based therapy. The association between PDL1 expression and B7-H4 expression in human tumors was evaluated. To evaluate PDL1 levels a rabbit monoclonal antibody (E1L3N) from Cell Signaling Technology Inc., (Danvers, Mass.) was used. The specificity and sensitivity were evaluated using positive control cell models and human tissue samples from placenta and tonsil.

PDL1 staining in lung cancer (n=91) was evaluated. The PDL1 membrane staining was quantified using the following criteria. Staining in both tumor cells as well as infiltrating leukocytes were included in the analysis. A representative image of PDL1 staining is presented in FIG. 6.

0 (negative)=No or less than 1% of cells have membrane staining

1+ (mild)=1 to 5% of the cell are positive

2+ (moderate)=5 to 49% of the cells are positive

3+ (strong)=>50% of the cells are positive

PDL1 positive staining was observed in ~45% of the lung cancer samples. 53% (n=49) of the squamous subtype of NSCLC was positive for PDL1 expression and 31% (n=16) of adenocarcinoma was positive for PDL1 expression. A summary of these results are presented in Table 6.

TABLE 6

Summary of the Prevalence of PD-L1 expression in NSCLC

| Tumor sub-type | Stage | N | Strong (3+) | Moderate (2+) | Weak (1+) | Negative |
|---|---|---|---|---|---|---|
| SCLC | | 3 | 0 | 0 | 0 | 3 (100%) |
| Squamous | Stage I | 4 | 0 | 0 | 2 (50%) | 2 (50%) |
| | Stage II | 15 | 0 | 5 (33%) | 4 (27%) | 6 (40%) |
| | Stage III | 30 | 3 (10%) | 5 (17%) | 7 (23%) | 15 (50%) |

TABLE 6-continued

Summary of the Prevalence of PD-L1 expression in NSCLC

| Tumor sub-type | Stage | N | Strong (3+) | Moderate (2+) | Weak (1+) | Negative |
| --- | --- | --- | --- | --- | --- | --- |
| Adenocarcinoma | | 16 | 0 | 1 (6%) | 4 (25%) | 11 (69%) |
| Adenosquamous | | 8 | 0 | 2 (24%) | 3 (38%) | 3 (38%) |
| Brochiolalveolar carcinoma | | 11 | 0 | 0 | 3 (27%) | 8 (73%) |
| Undifferntiated | | 4 | 0 | 1 (25%) | 1 (25%) | 2 (50%) |

PDL1 expression and B7-H4 expression were compared from adjacent sections in breast, ovarian, lung and HNSCC cancer samples (n=85; 92; 91; 94 samples, respectively). Samples with B7-H4 staining from the range of 1+ to 3+ were scored as positive. Similarly samples with PDL1 staining within the range of 1+ to 3+ were scored as positive for PDL1 expression. 13% of breast cancer was observed to be positive for PDL1 expression. None of the PDL1 positive tumors were positive for B7-H4 expression. These data clearly demonstrate that PDL1 and B7-H4 plays a mutually exclusive role in suppressing immune surveillance. A minority of tumors from ovarian, lung and HNSCC (9%; 11%; 9% respectively) were observed to be positive for both PDL1 and B7-H4. These results are summarized in FIG. 7. These results show that tumors that are positive for B7-H4 and negative for PDL1 expression will unlikely show any significant clinical benefit from PD-1 or PDL1 based therapy, but likely to benefit from B7-H4 targeted therapy.

Using an immuno-fluorescence based multiplex immunohistochemistry (IHC) analysis the expression of PDL1 and B7-H4 was compared at a cellular level. Tissue sections were sequentially stained using anti-PD-L1, anti-B7-H4 and anti-CD3 (a T-cell marker) and visualized with distinct fluorochromes using a tyramide based signal amplification system (Perkin Elmer, USA). An example of an ovarian tumor section with CD3, PDL1 and B7-H4 triple staining is shown in FIGS. 8A and 8B. Adjacent sections were stained with PDL1 alone or B7-H4 alone to ensure the specificity of the staining (data not shown). The data show that PDL1 expression is strictly restricted to the cells that are in close proximity to the CD3 positive cells. In contrast, B7-H4 expression is absent in these cells. Conversely, the cells that are positive for B7-H4 are negative for PDL1 staining. These data show that PDL1 and B7-H4 acts in a mutually exclusive manner Example 4

In Vivo Models

Figure 9A:
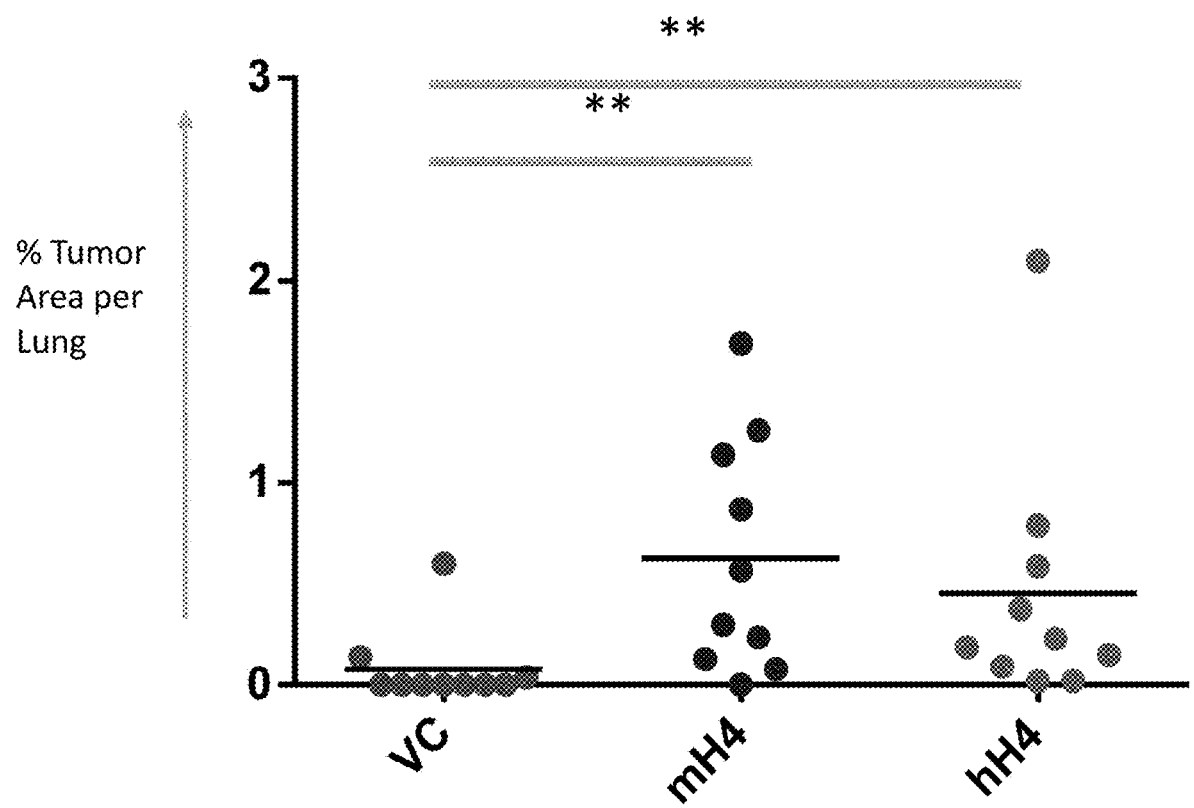
FIGS. 9A and 9B are graphs showing the quantification of percent tumor area (FIG. 9A) and number of tumors (FIG. 9B) on H&E staining of lung tissue from mice that have been injected i.v. with CT26 cells overexpressing mouse or human B7-H4. CT26 cells infected with vector control (VC) are used as controls.
Figure 9B:
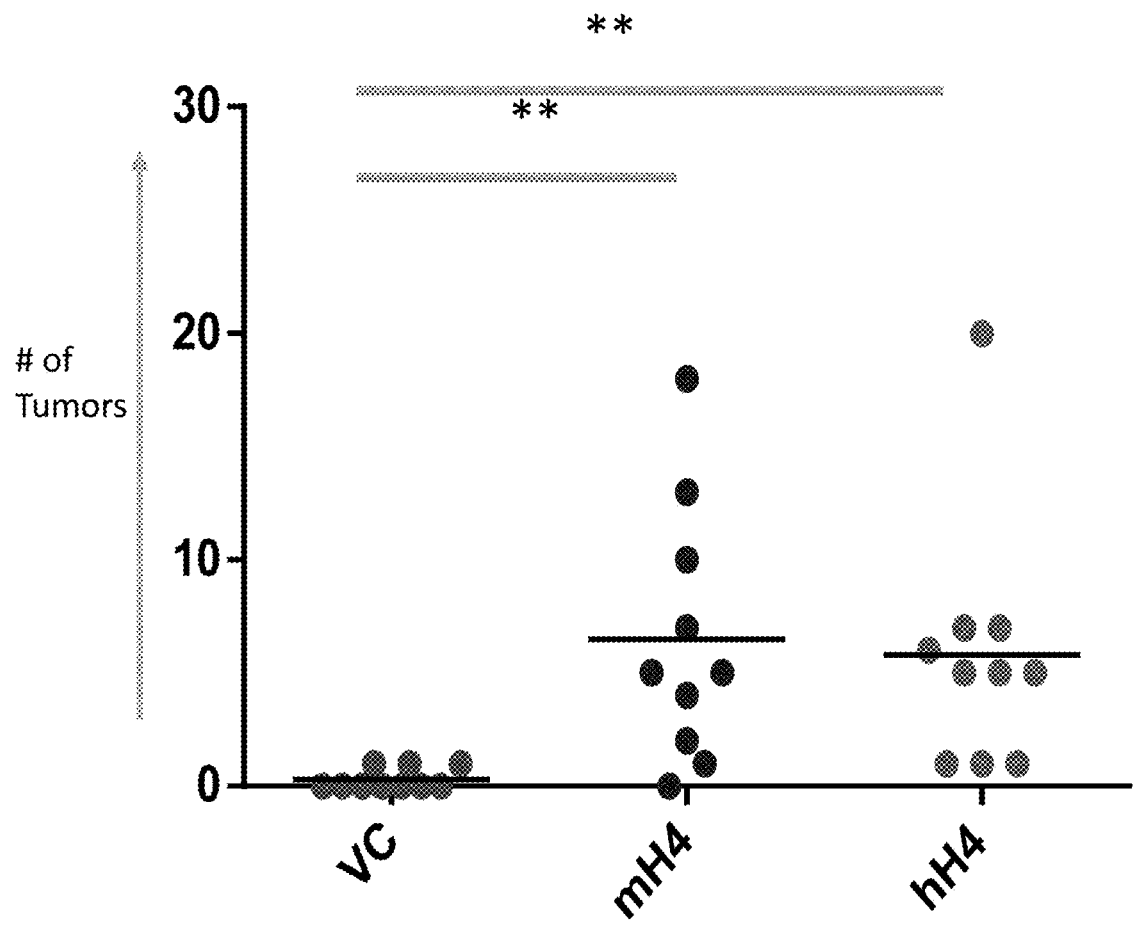

In Vivo Assay was Established to Assay B7-H4 Immunological Functionality on Developing Tumor. Development of a Tumor Model Dependent on B7-H4 for Progression An in vivo tumor model was established in lung with CT26 colon cancer cells overexpressing mouse or human B7-H4 in which overexpression of mB7-H4 induces faster tumor progression. Tumor cells were injected intravenously and tissues were harvested at days 14, 21 and 27 post cell inoculation. By day 14, it was observed that there was already higher number of tumors as well as larger percent tumor area in lungs of mice injected with CT26 cells overexpressing mouse and human B7-H4 in comparison to controls (depicted on FIGS. 9A and 9B).

Example 5

The present example outlines how one of skill in the art can use a B7-H4 antibody. One identifies a subject who will benefit from a B7-H4 antibody and then administers the B7-H4 antibody to the subject in an effective amount. The subject can be identified as having a cancer that expresses a high level of B7-H4 (at least 5% of the cells of the cancer are stainable via a B7-H4 marker). However, the cancer will also express a low level of PDL1 (less than 1% of the cells of the cancer are stainable by a PDL1 marker). The amount of the B7-H4 antibody administered will reduce B7-H4 activity in the subject.

Example 6

The present example outlines a method for treating a lung cancer, a breast cancer, a head and neck cancer, an ovarian cancer, or an endometrial cancer. One provides a subject having at least one of a lung cancer, a breast cancer, a head and neck cancer, an ovarian cancer, or an endometrial cancer and provides a B7-H4 antibody in a therapeutically effective amount to the cancer in the subject. The cancer is also at least one of: a) not responsive to PD-1 therapy, b) expresses a low level PDL1 (as determined by a negative score on a staining assay, or c) also receiving a therapeutically effective amount of PD-1 therapy. The result is that the lung cancer, breast cancer, head and neck cancer, ovarian cancer, or endometrial cancer is thereby treated.

Example 7

To test whether antibodies against B7-H4 mediate ADCC, an assay was set up using SKBR3 cells that naturally express B7-H4 as the target. SKBR3 also express HER-2, therefore allowing one to use a Herceptin antibody as a positive control in these assays since this approved therapy directed against HER-2 works in part through an ADCC mechanism. Target cells were incubated with PBMCs from two or more donors in the presence of various antibodies at 1 µg/ml at a concentration previously identified to yield good responses in this assay (the percentage of cytotoxicity was measured as an indication of the level of ADCC). Select representatives of 4 epitopic bins (identified by numbers in the x-axes) with human IgG1 ('original IgG1'), hIgG4 (IgG4) with S228P mutation, anti-Her2 antibodies in the IgG1 or IgG4 were generated (as outlined below) based on the trastuzumab sequence with the identical Fc backbones as that of anti-B7-H4 mAb versions. Anti-Her2-hIgG1 with trastuzumab sequence produced at Jounce was used as a positive control for ADCC on SKBR3 cells.

Figure 11A:
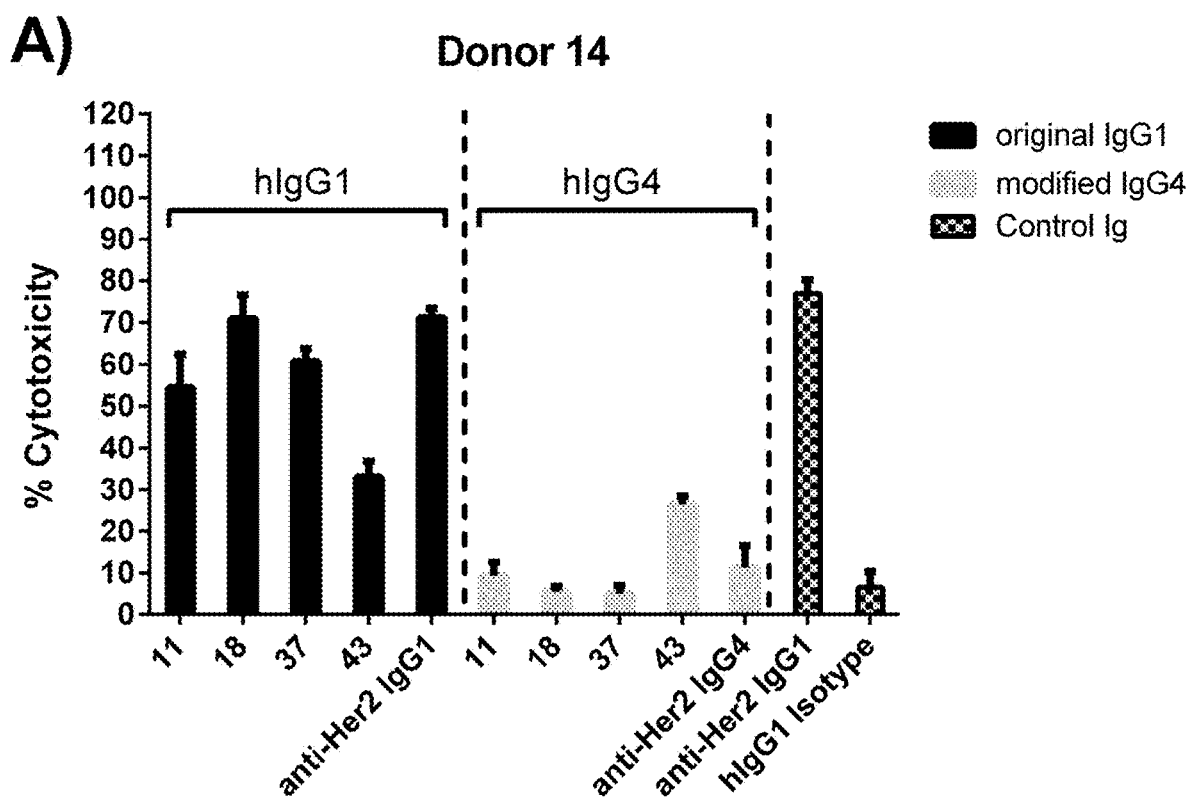
FIGS. 11A and 11B are graphs depicting the ADCC effectiveness for four different antibodies in an IgG1 arrangement (representing ADCC) vs an IgG4 arrangement.
Figure 11B:
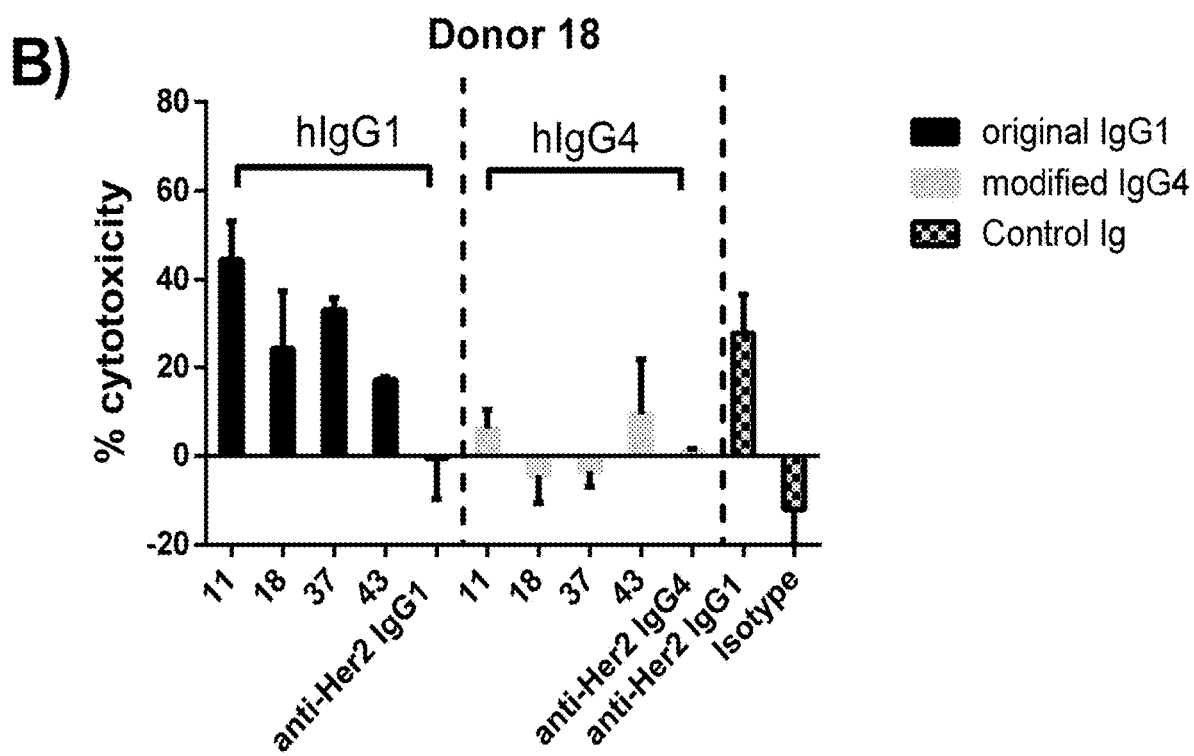

The data, shown in FIGS. 11A and 11B, indicates that antibodies (discussed below) derived from the rodent fusions, and representing each of the 4 epitope bins, have ADCC activity and this activity is dependent on the Fc backbone. When the antibodies were put in human IgG4 backbones, the ADCC activity was dramatically reduced (hIgG4 has low effector function as compared to IgG1). Similar data was also observed in MX-1 cells, a human breast cancer cell line lacking hormone receptors (ER, PR), express low levels of Her2, and representative of TNBC.

In regard to the generation of the antibodies discussed above, hybridoma supernatants from mice immunized with recombinant human (h) and mouse (m) B7-H4-Fc fusions protein (dimeric construct) and B7-H4-HIS (monomeric construct) produced in HEK-293 mammalian cells were screened for: (a) specific binding to hB7-H4 protein but not an irrelevant Fc fusion protein by ELISA, and (b) specific binding to human and mouse B7-H4 over-expressing CHOK1 cell lines by flow cytometry. Following this, hybridoma supernatants from mice immunized with hB7-H4 expressing 293 cells were screened for: (a) positive staining on hB7-H4-CHOK1 and negative staining on CHOK1 and (b) selective binding to human and mouse B7-H4-Fc but not irrelevant Fc protein, and by ELISA. A total of 51 hybridomas were selected using the above screening paradigm and underwent further characterization with regard to their binding affinity, and to their ability to cross-block resulting in assignment to 4 epitope groups (or bins). Based on this analysis, representative members from each of the classes (or bins) G1: mAb011; G2: mAb018; G3: mAb037; G4: mAb043 were selected for analysis as outlined above.

Example 8

Figure 12:
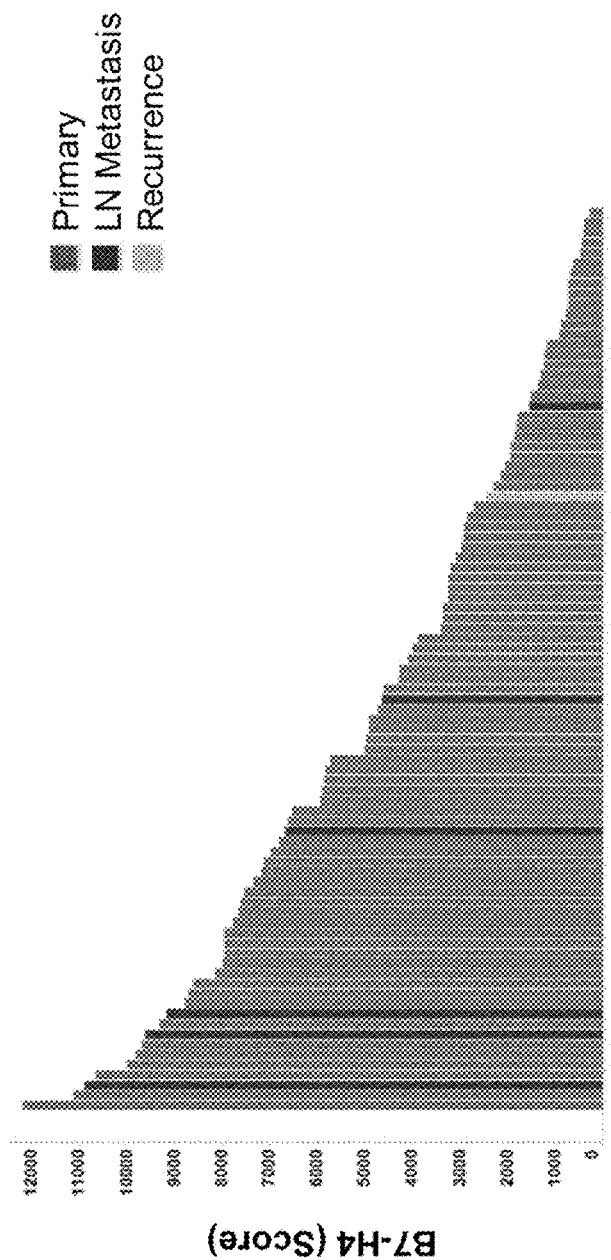
FIG. 12 depicts a graph of the distribution of B7-H4 expression in TNBC patients. B7H4 levels in primary or lymph node metastatic lesions or recurrent samples as measured by Aqua score are plotted.

Evaluation of B7-H4; PD-L1 and CD8 Infiltration in TNBC Collected by Immune-Fluorescence IHC B7-H4, PD-L1, and CD8 expression was evaluated in a set of 125 of hormone receptor (ER, PR & Her2) negative breast tumors. The hormone receptor status in these samples were evaluated by clinical assays. B7-H4 expression was analyzed using a rabbit monoclonal antibody which recognizes human B7-H4 (clone 8E7 from Cell Signaling Technology Inc., Danvers, Mass.). B7-H4 expression was quantified using an immunofluorescence (IF) based multiplex analysis. Tissue sections were sequentially stained with anti-B7-H4, anti-PDL1 (clone E1L3N). Each section was also co-stained with a tumor specific antibody against cytokeratin (CK) (Clone AE1/AE3, Dako Inc., Carpinteria, Calif.). Tyramide based signal amplification system (Perkin Elmer, USA) was used to detect and visualize different targets. The ratio of B7-H4 or PDL1 signal intensity to the CK signal intensity was used to calculate relative expression levels of B7-H4 or PDL1 based on "AQUA" Score analysis (JNCI 2005; 97: 1808-15). Sufficient tumor sample was available for B7-H4 quantification in 87 patients. The distribution of B7-H4 Aqua score in these patients is presented in FIG. 12.

A majority (79%) of the TNBC patients had a detectable (visual) level of B7-H4 staining in this cohort. B7-H4 staining was detected in both primary and metastatic lesions. B7-H4 expression was not associated with the stage of the disease. The visual threshold for detection of B7-H4 was at ~2000 AQUA score.

Figures 13A, 13B:
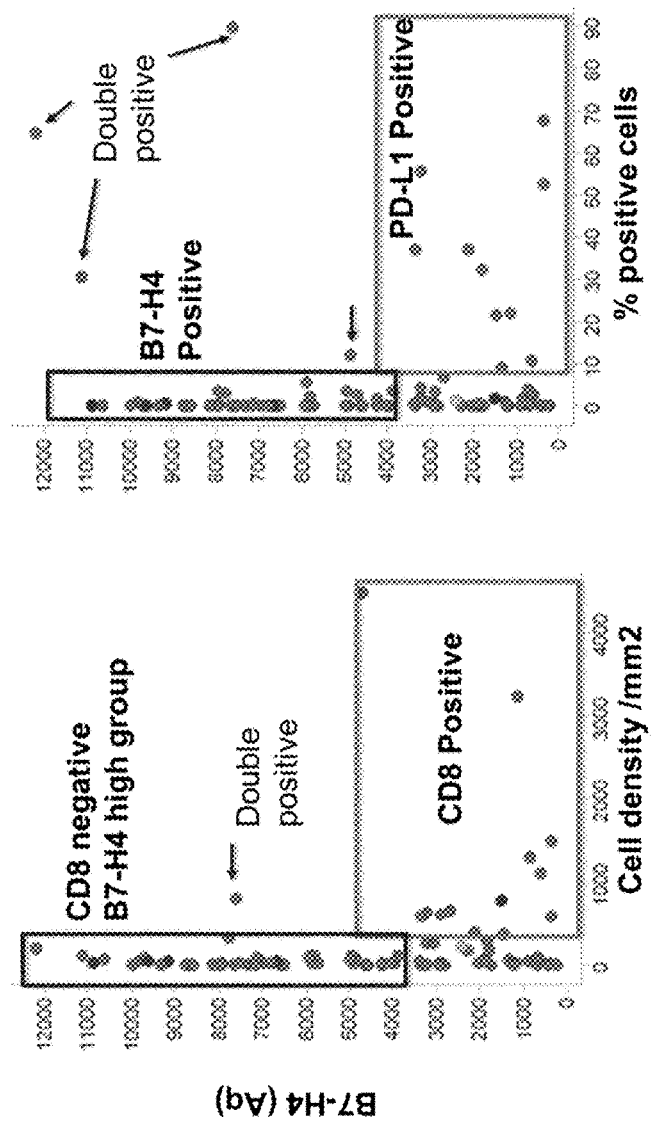
FIG. 13A and FIG. 13B are graphs showing a comparison of B7-H4 expression with CD8 infiltration (FIG. 13A) and PD-L1 infiltration (FIG. 13B). The Aqua score for B7-H4 in TNBC patients (n=87) were compared to CD8 density (number of CD8 cells/mm$^2$) or percentage of PD-L1 positive cells (both tumor and immune cells).

B7-H4 expression levels were compared with the levels of PDL1 expression (FIG. 13A) and density of CD8 infiltration (FIG. 13B). PDL1 levels and CD8 infiltration were evaluated by staining with anti-PDL1 antibody (clone E1L3N, Cell Signaling Technologies Inc., Danvers, Mass.) and anti-CD8 antibody (Clone C8/144B, Dako Inc. Carpinteria, Calif.) respectively. The PDL1 levels were quantified as % of DAPI staining nuclei that are positive for PDL1 expression. CD8 infiltration was quantified as the number of CD8 positive cells per unit area ($mm^2$) of viable tumor.

The majority of the patients expressed either B7-H4 or PDL1. A small subset of patients (4.5%) expressed both B7-H4 and PDL1. Similarly, B7-H4 positive tumors has low levels of T-cell infiltration as measured by CD8 density. A minority of the TNBC tumors (1.1%) showed high levels of B7-H4 expression and high density of CD8 infiltration.

These data show that a majority of B7-H4 positive tumors are negative for PDL1 and have low levels of T-cell infiltration.

In some embodiments, the population to be treated will be one that is PDL1 negative (as shown on the right hand side in FIG. 13B), with a high level of B7-H4, as boxed in on the right as a "positive". In some embodiments, the double positives could also be treated (e.g., those not responding to PD-1 therapy).

Example 9

The present example outlines a method for treating breast cancer. To a subject having breast cancer, one provides an ADCC capable B7-H4 antibody having the 6 CDRs as provided in at least one of FIGS. 11C-11F in a therapeutically effective amount. The cancer is also at least one of: a) not responsive to PD-1 therapy, b) expresses a low level PDL1 (as determined by a negative score on a staining assay, c) also receiving a therapeutically effective amount of PD-1 therapy, or d) no longer responsive to PD-1 therapy. The result is that the breast cancer is thereby treated through ADCC.

Example 10

PD-L1 Scoring

PDL1 IHC 22C3 pharmDx test (Dako Inc., Carpinteria, Calif.), can be used for evaluation of PDL1 expression in NSCLC.

A formalin-fixed paraffin-embedded (FFPE) Non-Small Cell Lung Cancer (NSCLC) tissue sample is collected. An Autostainer Link 48 system is used to process and visualize the sample using the EnVision FLEX system. PDL1 protein expression is qualified using Tumor Proportion Score (TPS), which is the percentage of viable tumor cells showing partial or complete membrane staining. The sample is PD-L1 positive if TPS≥50% of the viable tumor cells exhibit membrane staining at any intensity (using antibody clone 22C3).

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed is:

1. A method of treating cancer in a human subject, the method comprising administering a therapeutically effective dose of an anti-human B7-H4 antibody to said human subject, wherein the B7-H4 antibody comprises at least one of the following:
   a) three heavy chain CDRs that are the heavy chain CDRs in SEQ ID NO: 18 and three light chain CDRs that are the light chain CDRs in SEQ ID NO: 19;
   b) three heavy chain CDRs that are the heavy chain CDRs in SEQ ID NO: 26 and three light chain CDRs that are the light chain CDRs in SEQ ID NO: 27;
   c) three heavy chain CDRs that are the heavy chain CDRs in SEQ ID NO: 34 and three light chain CDRs that are the light chain CDRs in SEQ ID NO: 35; or
   d) three heavy chain CDRs that are the heavy chain CDRs in SEQ ID NO: 42 and three light chain CDRs that are the light chain CDRs in SEQ ID NO: 43.

2. The method of claim 1, wherein for:
   a) the three heavy chain CDRs comprise: an amino acid sequence of SEQ ID NO: 12, an amino acid sequence of SEQ ID NO: 13, and an amino acid sequence of SEQ ID NO: 14, and the three light chain CDRs comprise: an amino acid sequence of SEQ ID NO: 15, an amino acid sequence of SEQ ID NO: 16, and an amino acid sequence of SEQ ID NO: 16;
   b) the three heavy chain CDRs comprise: an amino acid sequence of SEQ ID NO: 20, an amino acid sequence of SEQ ID NO: 21, and an amino acid sequence of SEQ ID NO: 22, and the three light chain CDRs comprise: an amino acid sequence of SEQ ID NO: 23, an amino acid sequence of SEQ ID NO: 24, and an amino acid sequence of SEQ ID NO: 25; or
   c) the three heavy chain CDRs comprise: an amino acid sequence of SEQ ID NO: 28, an amino acid sequence of SEQ ID NO: 29, and an amino acid sequence of SEQ ID NO: 30, and the three light chain CDRs comprise: an amino acid sequence of SEQ ID NO: 31, an amino acid sequence of SEQ ID NO: 32, and an amino acid sequence of SEQ ID NO: 33; or
   d) the three heavy chain CDRs comprise: an amino acid sequence of SEQ ID NO: 36, an amino acid sequence of SEQ ID NO: 37, and an amino acid sequence of SEQ ID NO: 38, and the three light chain CDRs comprise: an amino acid sequence of SEQ ID NO: 39, an amino acid sequence of SEQ ID NO: 40, and an amino acid sequence of SEQ ID NO: 41.

* * * * *